United States Patent
Prichard et al.

(10) Patent No.: US 10,000,811 B2
(45) Date of Patent: Jun. 19, 2018

(54) MARKERS TO PREDICT MACROCYCLIC LACTONE DRUG RESISTANCE IN DIROFILARIA IMMITIS, THE CAUSATIVE AGENT OF HEARTWORM DISEASE

(71) Applicants: Elanco US Inc., Indianapolis, IN (US); McGill University, Montreal, Quebec (CA)

(72) Inventors: Roger K. Prichard, Quebec (CA); Catherine Bourguinat, Quebec (CA); Timothy G. Geary, Quebec (CA)

(73) Assignee: Elanco US Inc. and McGill University, Greenfield, IN (US)

( * ) Notice: Subject to any disclaimer, the term of this patent is extended or adjusted under 35 U.S.C. 154(b) by 107 days.

(21) Appl. No.: 14/896,736

(22) PCT Filed: Jun. 25, 2014

(86) PCT No.: PCT/US2014/044000
§ 371 (c)(1),
(2) Date: Dec. 8, 2015

(87) PCT Pub. No.: WO2014/210097
PCT Pub. Date: Dec. 31, 2014

(65) Prior Publication Data
US 2016/0153042 A1    Jun. 2, 2016

Related U.S. Application Data

(60) Provisional application No. 61/839,545, filed on Jun. 26, 2013.

(51) Int. Cl.
C07H 21/04    (2006.01)
C12Q 1/68    (2018.01)

(52) U.S. Cl.
CPC ......... *C12Q 1/6883* (2013.01); *C12Q 1/6888* (2013.01); *C12Q 2600/124* (2013.01); *C12Q 2600/136* (2013.01); *C12Q 2600/156* (2013.01)

(58) Field of Classification Search
None
See application file for complete search history.

(56) References Cited

FOREIGN PATENT DOCUMENTS

WO    WO/2011/120165 A1    10/2011

OTHER PUBLICATIONS

Godel et al. (FASEB, vol. 26, No. 11, pp. 4650-4661, Aug. 15, 2012).*
Bourguinat, Catherine, et al. "Correlation between loss of efficacy of macrocyclic lactone heartworm anthelmintics and P-glycoprotein genotype." Veterinary parasitology 176.4 (2011): 374-381.
Godel, Christelle, et al. "The genome of the heartworm, Dirofilaria immitis, reveals drug and vaccine targets." The FASEB Journal 26.11 (2012): 4650-4661.
Anonymous: "The genome of the heartworm, Dirofilaria immitis," (Aug. 6, 2012) Retrieved from the internet: http://hematodes.org/genomes/dirofilaria_immitis/ on Oct. 30, 2014.
Anonymous: "BLASTN" (Oct. 30, 2014), XP05515004, Retrieved from the internet: http://xyala.cap.ed.ac.uk/tmp/blast/102371414680881.blastn.htm on Oct. 30, 2014. Sequence alignment with nDi.2.2.scaf00021.
Anonymous: "Safety Data Sheet—Random Hexamer Primers" (Apr. 23, 2012), XP055150159, Retrieved tom the internet: https://ools.lifetechnologies.com/content/sfs/msds/2012/N8080127_MTR-EULT_BE.pdf on Oct. 31, 2014.
Database EMBL (online): "PV_GBa0077F16.r V_GBa Phaseolus vulgaris genomic clone PV_GBa0077F16 3', genomic survey sequence.", XP002731895, retrieved from EBI accession No. EM_GSS:EI469912, Database accession No. EI469912 sequence, Mar. 29, 2007.
Database GenBank (online): "Dirofilaria immitis WGS project CAWD000000000 data, contig 000021_632,-Nucleotide—NCBI", XP002731896, retrieved from NCBI accession No. CAWD010000632.1, nucleotides 2461 to 2162, Aug. 20, 2013.

* cited by examiner

*Primary Examiner* — Jeanine A Goldberg
(74) *Attorney, Agent, or Firm* — David L. Pflugh

(57) ABSTRACT

Disclosed are nucleic acid molecules from the genome of *Dirofilaria* spp. nematodes that contain single nucleotide polymorphisms related to reduced responsiveness of the nematodes to macrocyclic lactones. In one example, the species of *Dirofilaria* is *Dirofilaria immitis* (the agent of heartworm in animals). Also disclosed are methods for determining the responsiveness of *Dirofilaria* spp. nematodes to macrocyclic lactones, methods for selecting a treatment to treat an animal infected with a *Dirofilaria* spp. nematode, and kits for determining the responsiveness of *Dirofilaria* spp. nematodes to macrocyclic lactones.

5 Claims, 29 Drawing Sheets

Table 1. Genotype frequencies for markers representing SEQ ID NOs: 110-127

| SNP Loci | % Genotype Frequency Susceptible | | | % Genotype Frequency Confirmed Resistant | | | Comparison Susceptible/Confirmed Resistant p-value | % Genotype Frequency Confirmed Resistant + LOE | | | Comparison Susceptible/Confirmed Resistant + LOE p-value |
|---|---|---|---|---|---|---|---|---|---|---|---|
| | CC | CT | TT | CC | CT | TT | | CC | CT | TT | |
| MARKER_31307* | | | 100.0% | 2.9% | 11.7% | 85.4% | 6.3E-05 | 8.7% | 8.7% | 82.6% | 5.7E-06 |
| MARKER_26225* | | 0.7% | 99.3% | 1.3% | 48.3% | 50.3% | 3.7E-21 | 1.9% | 47.2% | 50.9% | 1.2E-23 |
| MARKER_47722_B* | 6.5% | 1.3% | 92.3% | 22.7% | 33.7% | 43.6% | 5.0E-20 | 18.9% | 23.5% | 57.6% | 2.9E-14 |
| MARKER_52162_B | 0.7% | 1.5% | 97.8% | 26.7% | 18.6% | 54.7% | 1.8E-16 | 30.7% | 14.7% | 54.6% | 1.0E-18 |
| | AA | AG | GG | AA | AG | GG | | AA | AG | GG | |
| MARKER_17709* | 100.0% | | | 74.1% | 19.0% | 6.8% | 4.3E-02 | 67.3% | 17.5% | 15.1% | NS |
| MARKER_47141* | 100.0% | | | 56.7% | 43.3% | | 4.7E-23 | 68.8% | 27.7% | 3.5% | 3.5E-16 |
| MARKER_48750_A | 100.0% | | | 54.9% | 28.7% | 16.5% | 1.3E-15 | 54.1% | 24.8% | 21.0% | 1.9E-17 |
| MARKER_63962 | 100.0% | | | 87.7% | 11.7% | 0.6% | 1.0E-03 | 81.9% | 11.8% | 6.2% | 1.7E-05 |
| MARKER_6272 | 90.2% | 2.3% | 7.5% | 20.2% | 49.7% | 30.1% | 1.8E-32 | 35.8% | 32.9% | 31.3% | 2.0E-26 |
| MARKER_15611* | 90.5% | | 9.5% | 53.3% | 26.7% | 20.0% | 9.3E-14 | 47.7% | 15.9% | 36.4% | 6.9E-19 |
| | AA | AT | TT | AA | AT | TT | | AA | AT | TT | |
| MARKER_46432 | | | 100.0% | 0.8% | 15.0% | 84.2% | 8.2E-05 | 3.2% | 10.3% | 86.5% | 3.0E-04 |
| MARKER_29594 | 1.2% | 8.7% | 90.1% | 12.7% | 32.9% | 54.4% | 1.5E-12 | 12.4% | 20.8% | 66.8% | 1.4E-08 |
| | CC | CG | GG | CC | CG | GG | | CC | CG | GG | |
| MARKER_26793 | | | 100.0% | 16.8% | 7.2% | 76.0% | 1.4E-07 | 10.1% | 4.4% | 85.4% | 1.0E-04 |
| MARKER_51661 | 100.0% | | | 45.5% | 39.4% | 15.2% | 2.7E-23 | 48.9% | 29.0% | 22.1% | 2.7E-24 |
| MARKER_7819* | 94.9% | 1.9% | 3.2% | 45.2% | 39.2% | 15.7% | 3.1E-21 | 52.6% | 23.5% | 23.0% | 3.1E-19 |
| MARKER_26704* | 90.4% | 4.5% | 5.1% | 70.2% | 27.4% | 2.4% | 2.5E-08 | 85.8% | 22.7% | 11.5% | 2.2E-09 |
| | AA | AC | CC | AA | AC | CC | | AA | AC | CC | |
| MARKER_14329 | 1.1% | 6.1% | 92.8% | 6.4% | 14.0% | 79.7% | 9.9E-04 | 17.4% | 20.4% | 62.2% | 1.0E-13 |
| | GG | GT | TT | GG | GT | TT | | GG | GT | TT | |
| MARKER_58169 | | | 100.0% | 16.0% | 1.3% | 82.7% | 5.0E-03 | 21.8% | 1.1% | 77.1% | 4.8E-04 |

*For markers designated with an asterisk (*), the genotype indicated shows analysis of the reverse complement of the sequences shown as SEQ ID NOs: 110-127.

Figure 29

SEQUENCE LISTING

```
<160> NUMBER OF SEQ ID NOS: 127

<210> SEQ ID NO 1
<211> LENGTH: 300
<212> TYPE: DNA
<213> ORGANISM: Dirofilaria immitis

<400> SEQUENCE: 1
aacataaaca tattgaactg aatcctgcaa acagttctct tataacgtga accataacta        60
aatttagaga aaatatgaaa aagaaaaata agttgctttt gctcgtgcac caactctaat       120
acccaggaaa tcaagaagtg ataatgagta atgtcatcat tagattcagt aattggtgac       180
actatcaata ttattattat tatacttaaa aatacgacga ccacttatcg taacttaaag       240
catgcataat acgactgtca tcatattaca tttcttcaag ttcgtattgg acaagtgatt       300

<210> SEQ ID NO 2
<211> LENGTH: 300
<212> TYPE: DNA
<213> ORGANISM: Dirofilaria immitis

<400> SEQUENCE: 2
gacaagcgtt gacgggagag acgatataat aataaagaag gcattgggta tcagaaggca        60
caatccaatt ataaatgcca aggcaaaatg aataaaattt atgctgacga tttgatcaat       120
tacgaagaat ttccgatcgg ctcgaatctt tgtttgtatg tgcactactg ttaacttaat       180 cttgtttta tatacttttg cgtgtcatat ataatatatt catgtcaact gatacgttat       240
gatgtttttt tgtaaattaa gttgatcgga aacctgaagt ctatttcaaa tttaagaaat       300

<210> SEQ ID NO 3
<211> LENGTH: 300
<212> TYPE: DNA
<213> ORGANISM: Dirofilaria immitis

<400> SEQUENCE: 3
```

```
ttttaggaaa atggtgactg tagagagata ttatcggaac gacaaggtcc acttcgaacg    60
ggtcttttat tgtcgacgga ttgtgaacca agttttggca ttcataatga caggtagcta   120
tttttccatc atcccatttt tgtattagtg caagcaagtc atgagtcgaa agaaaatctc   180
aaaagaaaaa aatgaaattt caggttcaaa ggactgcgtc cattattcgc actggttgat   240
gagaacgtac agattccaga gcggcaatgc tgcacagtat cttttgtttc acttctgaat   300

<210> SEQ ID NO 4
<211> LENGTH: 300
<212> TYPE: DNA
<213> ORGANISM: Dirofilaria immitis

<400> SEQUENCE: 4
tcgattaaaa attatcatcg ataaaattct aaaatttatt ttagtaaaat tattattatt    60
ttgatgaata agttaacaaa aaaattttaa taacttttttg attcgccaaa aatctaattc   120
gttaaaaagt cgttccaaac agatatcgct tgttcgatga aatgtccgg ttgttagaaa    180 atcataaatt ggttcaaata attttccaga acgttcgaaa aaatattccc ttgtatcgga   240
taaataacca ttacaatttt ccactcgtgt tgcatgtgtt tctcgacaaa aatcagctaa   300

<210> SEQ ID NO 5
<211> LENGTH: 300
<212> TYPE: DNA
<213> ORGANISM: Dirofilaria immitis

<400> SEQUENCE: 5
tcaacagaaa tcgagattcc aaaaagtttc ctacaaatac ttaattatca atggatattt    60
agttttgtta tctgttatca taagttctgc ttcttacacg attaaaaatg tccaagaatt   120
ttttactatt caaatgaggg aaataaaaaa ccaatgccaa taatatccag aaactacata   180
catctttctt ttttcgaagc tcatctattc cggccgaaaa caatgaagaa cattaaaatt   240
cttaaaagat agtcttagcc ttttccttga ccactatctt aactgtcagc gctaaaatgt   300

<210> SEQ ID NO 6
<211> LENGTH: 300
<212> TYPE: DNA
<213> ORGANISM: Dirofilaria immitis

<400> SEQUENCE: 6
aatagtcgtc tcattacttt ttgacttta taattcgaga atcttatgta gtccttcact    60
ttacccttct tctgtcgaac taagaattac agcattattt tcgaatttaa tgtgtaaaag   120
acaatagcag attttgtaat tttgtgttaa cctcacttta tatttcgctt catatcgtga   180
cagagaatta ctatttcaga gagtattact tgtcaccaga gaatctccag aaagattttt   240
atttacgtcg gaaaatggac aaaaatggtt tcttatcatt agcactgata gctagtttcc   300

<210> SEQ ID NO 7
<211> LENGTH: 300
<212> TYPE: DNA
<213> ORGANISM: Dirofilaria immitis

<400> SEQUENCE: 7
tatctcttgt tgtgtgttct gcattgtatc aaagtgggta aattttgctt tagacgttga    60
cttattgtct ttttaagtt atattctagt ccatgttttt ctctttgcaa atatttttt    120 ccgccgccta tgattcattg ttttgttgt aactctctat taagttgctt ttagtttgaa   180
ttgtatcaaa atttcaaaca tttaaaatac gcactagcac tattttttct tatctcaatt   240
```
aagcgaatcc cggaacaaga tttaatcgat ttccgaatca caattaaatc actggaaaac    300

<210> SEQ ID NO 8
<211> LENGTH: 300
<212> TYPE: DNA
<213> ORGANISM: Dirofilaria immitis

<400> SEQUENCE: 8
attttcctta acaaatcatt ttcaaacgaa aaaacattaa aaagtgttaa aataaaatgg     60
tgatattgat aagaaattaa ttcaacctgc atatcaattc ttgtagcggc catttttctta  120
gcaagttcta tagcagctcg atccatatca ccttcttgct ctaatgtcaa ttccggttcc   180
ggaatttttt ttattttgcc attcttcatc tttttttttat tttttactga tatagctata  240
gacccttcct cccgtgcatg cctgtaggcc tgttctgata tacaggcttg tgaaccactg    300

<210> SEQ ID NO 9
<211> LENGTH: 300
<212> TYPE: DNA
<213> ORGANISM: Dirofilaria immitis

<400> SEQUENCE: 9
ttctggggta gttatacgga aaattagaca atgaagagaa tcaaaaaaca tgcgattttc     60
aaacagagga actttggtac ttttgcctcg acttacttta ttttaaaacc catacaaaat   120
aaatgtttca tttgattgat attgtcgtac taataattag agcttcaaca ttaggatttt   180
aataaccttc aatttatttc agaatttaag aaacttacgt atggatggag aaaatataaa  240
gaatggcgat gacaaataag atttgctatg aaaaaactaa tgccacaaga tccgaatgca    300

<210> SEQ ID NO 10
<211> LENGTH: 300
<212> TYPE: DNA
<213> ORGANISM: Dirofilaria immitis

<400> SEQUENCE: 10
tttatgaaca aaaataataa aaattaggat aacagatatc aatttctttt agctataaat     60
atacgcttcg attgaaaaaa gctttcaaat tataattaag gcatacgtta cgatatagac   120
aattaagtcg acattaatta tttgaaatat tttaaatttt tttctctttc tttttttcta  180
ttctcttcca aagtgtcaaa tagttatgaa attgtcagaa gctaaaatga taatattatt   240
caagtttatt acctaatctt ttatcacctc atttcttatc atttatctga aaatctaatc    300

<210> SEQ ID NO 11
<211> LENGTH: 300
<212> TYPE: DNA
<213> ORGANISM: Dirofilaria immitis

<400> SEQUENCE: 11
atgttgaatt tttaatgaaa cttttcggt gcataagcat tacagatctg taagctgtgc      60
aaaccctgtt tctttgtaaa ttgaaacaaa gatcatttat tgtttccagc gtcgatttga   120
cctggataaa tgtggtacca aaagtagatg acgagaggta agtgcaaaca aaatgcacaa   180
aaatgatttt gatgcactca aatcattttt aagttttgtg caattttcca ttttatagtt    240
tcgtgatcgg ttgttattca tcaacttgat tttgtttgtt ttttgtgact tatattcat     300

<210> SEQ ID NO 12
<211> LENGTH: 300
<212> TYPE: DNA

<213> ORGANISM: Dirofilaria immitis

<400> SEQUENCE: 12

| tttgacactt | tcagatacct | tacaaactca | tctccagcac | ccaatttaca | atatcgctgc | 60 |
| ctaaataaag | aatttattcg | gatatgagac | tgtagttttc | attccgtacc | aatcatagta | 120 |
| gaacagatct | atagcatggt | gtcctactaa | agttgtgact | ggctattaag | tatgtgggtg | 180 |
| ttttacgtg | tgcgtgggtg | tttgtgcgtg | tgtgcgtgtg | cgtttctgca | catattttcg | 240 |
| tgcgcggtgt | ctgtgtgtgt | ccgtttgtat | atgccgagtg | tagctgtgtg | tatgttcttg | 300 |

<210> SEQ ID NO 13
<211> LENGTH: 300
<212> TYPE: DNA
<213> ORGANISM: Dirofilaria immitis

<400> SEQUENCE: 13

| cactcataat | atacctgtca | acaaactcag | aaatctgaat | aaaatgacgc | aaaaatgaca | 60 |
| aaaacatttt | atcaaccttt | tcttcatcac | tcccccgcat | ttccaatttt | cttccaaact | 120 |
| gttttttgtcg | tgctacaaag | tcatcagcca | cttcattttc | ttcaagatgg | ttcgagacgc | 180 |
| cattcttgga | ttcaccccctt | atttcaactg | tttccgaagt | cccagcagtt | gaagctgaac | 240 |
| ctagcattta | tatcaccacc | cgatgtcaaa | aaatgacagc | ggtcagagaa | tacgacttcc | 300 |

<210> SEQ ID NO 14
<211> LENGTH: 300
<212> TYPE: DNA
<213> ORGANISM: Dirofilaria immitis

<400> SEQUENCE: 14

| gctaggtcaa | cagttggttt | atttggactt | atacgatatt | aaacataata | tcgcctcata | 60 |
| tacacagaaa | tatcaaaaaa | acgaacacag | ctaaatcgaa | gaatacgaac | aaatgtttta | 120 |
| aaaattatat | taaatctttt | aatgctctct | acaatgtcgt | atcttcccctt | ttgtctgtat | 180 |
| ttctcctttc | gttccaccac | tgctatttct | catgcctttg | aactatggtt | ctcgttgcgt | 240 |
| cgaattgtcc | tcgaaactgt | tgtttctgtc | gaattacgtc | gaactgctgg | actttgtcgg | 300 |

<210> SEQ ID NO 15
<211> LENGTH: 300
<212> TYPE: DNA
<213> ORGANISM: Dirofilaria immitis

<400> SEQUENCE: 15

| atatctcact | tctgacataa | attgaagtgg | cactgatttg | aatgaaatga | taaataaaat | 60 |
| aaagacgaca | aggtagtgga | aaaaaaaaga | ggagaaaaca | ccgtttagtt | ttggatgcaa | 120 |
| gctcgaatct | gagttttctt | gcaaaccgta | cactgatcaa | ttttcttaca | caaacataag | 180 |
| aaaaaaagaa | gtgattttac | tgtagctgta | tcgtataatt | caaatcatat | atatatatgt | 240 |
| ttcaataatc | tatacacttta | tgtatatttt | tttttgaatg | gaacagtgaa | tgattttaaa | 300 |

<210> SEQ ID NO 16
<211> LENGTH: 300
<212> TYPE: DNA
<213> ORGANISM: Dirofilaria immitis

<400> SEQUENCE: 16

| acaaatgcca | tcgggagaga | aatatcgttg | gcgtactgat | cacattggcg | gtatcacttc | 60 |
| tttgaaaact | ccagctggta | ttgtgtatca | tttcatgcaa | tacgctattt | ttgatcgaat | 120 |

```
atgtcgacgg cgtagtgttt cattttccaa cgcatcttac gttgcgtgta tggatgatga    180
cggacaatta ttggaatatc aaacaccgga tcgattgcat ccgtaaccct tgaaacgtga    240
catatatggg agagtagtgc aaataacttc agatggcgaa atattttct tcgaatatgg    300
```

```
<210> SEQ ID NO 17
<211> LENGTH: 300
<212> TYPE: DNA
<213> ORGANISM: Dirofilaria immitis

<400> SEQUENCE: 17
ataatatata tttccattga taatattttt catattatgt gatgtttgaa attttctgca     60
attgctacat tccgattaaa aacttttatt atccgtactg gagaattttg cttttttttg    120
acggtttgtt caataagttg tcaatatatt gtctgcctta gtaaaaccct tctaatctat    180
ccgttcgaat tggaagttga agttcagca tcattctttt agtgaggtgt ttaagttgtt    240
caatagatat tatttagaac gatctcaatt aaaatcttct gaatgatttt atgttttttat    300
```

```
<210> SEQ ID NO 18
<211> LENGTH: 300
<212> TYPE: DNA
<213> ORGANISM: Dirofilaria immitis

<400> SEQUENCE: 18
gcagcacatt gcacacagta aactgcaaac tgaattaaga gatattgggt tgaattattt     60
ctaatttaaa aggatataat aaatgacttt gatgattgtt gatttaagg tatctcggaa    120 gactccatca gtctcagtgc tctagcaatc gctataggta ctaaaagaaa agaaaagatg    180
tctcgttatt cactttgaaa tgtacatatc aaatcatttt gtcgtatgaa attaagtata    240
ttatgtctaa tcgtatcatt cgaaatgaat ttactgtcac tgttagaact atttaggcag    300
```

```
<210> SEQ ID NO 19
<211> LENGTH: 300
<212> TYPE: DNA
<213> ORGANISM: Dirofilaria immitis

<400> SEQUENCE: 19
agagttcaat cgccaagttg ttctttttct cgctcgcaga gatcaaaacg gtgttggcta     60
tacactcatt catcaggctg tgatagacat ctcttagaat ttcagtgctt ttctggatga    120
aaacattatt tctcaaacat gacacttaag gacaatagtg cgtgacttct ttgttaacgt    180
acacgagaaa acaaaacaga tgatgcttgt tatcttggtg ataaatgtgt attcagaata    240
atgttatata tctttgcgtg acaaatatca tttcgttata cttcggatac gccttttttat    300
```

```
<210> SEQ ID NO 20
<211> LENGTH: 300
<212> TYPE: DNA
<213> ORGANISM: Dirofilaria immitis

<400> SEQUENCE: 20
aactttactt gaactttttt ggtgttcaat tttgaatatt ataccaacca ttcagaagac     60
tgtatataga aatgaacctt caagaattaa tcgaaatttt tattaaaatc ttttatttga    120
atatttcatt atttaaactc attactattt gcagtatatt attagatcta atgtagaaaa    180 aaaaaatcaga tggcaaaaat aatatcatag gtttgttttt aaaattcatt gcaaaattca    240
gtgcgccgtt ccagtcgctc gtaattaccc tatccctgag ctttacaaaa agaatgcttt    300
```

<210> SEQ ID NO 21
<211> LENGTH: 300
<212> TYPE: DNA
<213> ORGANISM: Dirofilaria immitis

<400> SEQUENCE: 21

| | | | | | | |
|---|---|---|---|---|---|---|
| aggtatctag | atagcataat | aaattactac | acaaaccgat | ggaaacgcaa | gtttggcgtt | 60 |
| gcgtgttgat | acaaaatatt | agagccaagg | atggtatcac | atgtaaaact | gcaattttgc | 120 |
| tatttgttta | aagcaaataa | gaaataaata | tttcgttctt | attctttaat | ttatttcatc | 180 |
| agatggcttt | gttataccat | aattgtaaat | ctgtcatatc | ttaattgcgc | aatagcccaa | 240 |
| gattcttgta | tattcttaca | tttcacaatt | tattttctta | tttctagttt | tagaattata | 300 |

<210> SEQ ID NO 22
<211> LENGTH: 300
<212> TYPE: DNA
<213> ORGANISM: Dirofilaria immitis

<400> SEQUENCE: 22

| | | | | | | |
|---|---|---|---|---|---|---|
| aatagctact | cacagcttaa | gttaactaat | ggattcttga | atttatttaa | gcgtgtagtt | 60 |
| aagcgattaa | tatgatggat | gcccagaatc | gctttgtctt | atagtttgt | ctcgacagaa | 120 |
| aggatgcatt | gttgtcttga | atttgttcaa | gggaaaatta | aataggtttc | tttcaatgac | 180 |
| tcctattaaa | ttttttgaa | tttaggcttg | cattgcgtgt | tctgatccac | tattagcacg | 240 |
| tacgggtatc | gcagtgccat | gtgatgcagc | actatgcaaa | aaccacctcc | atgtcacttg | 300 |

<210> SEQ ID NO 23
<211> LENGTH: 300
<212> TYPE: DNA
<213> ORGANISM: Dirofilaria immitis

<400> SEQUENCE: 23

| | | | | | | |
|---|---|---|---|---|---|---|
| tctgttgtaa | gtttcacaat | ccagttaatt | taagctcagc | ttatttgaaa | ttttcaacaa | 60 |
| aattacgaaa | attactttct | cggttcattt | ttttcaacca | ccaaatattt | agcataattg | 120 |
| gcctgaaatc | gtcaaagttt | acaaactttt | gttcagcaat | cttctcttac | tcttacaata | 180 |
| aacatgatta | acttgtcgtc | ataccaatct | cgtttatagc | aaattctttt | caaaaaaaca | 240 |
| ttgctacaaa | ttttatatcg | catcatttca | acacgcataa | ttattttca | tatatgaaaa | 300 |

<210> SEQ ID NO 24
<211> LENGTH: 300
<212> TYPE: DNA
<213> ORGANISM: Dirofilaria immitis

<400> SEQUENCE: 24

| | | | | | | |
|---|---|---|---|---|---|---|
| ttcacaatcc | agttaattta | agctcagctt | atttgaaatt | ttcaacaaaa | ttacgaaaat | 60 |
| tactttctcg | gttcattttt | ttcaaccacc | aaatatttag | cataattggc | ctgaaatcgt | 120 |
| caaagtttac | aaactttat | tcagcaatct | cctcttactc | ttacaataaa | catgattaac | 180 |
| ttgtcgtcat | accaatctcg | tttatagcaa | attcttttca | aaaaaacatt | gctacaaatt | 240 |
| ttatatcgca | tcatttcaac | acgcataatt | attttcata | tatgaaaaac | catattataa | 300 |

<210> SEQ ID NO 25
<211> LENGTH: 300
<212> TYPE: DNA
<213> ORGANISM: Dirofilaria immitis

<400> SEQUENCE: 25

| attaactctg | aacccaaaga | ctgttggtta | aaataaagat | ctattttagt | tatacatcta | 60 |
| acattaaagg | ttttcgtacg | gaaacaagta | ggtttgataa | ttttcatgta | actgtaaaga | 120 |
| acacctgtga | aagggatcag | taaaatttgg | gggatgtagc | acggaaatat | gaagctgagt | 180 |
| gttttgtacc | caaaagtttt | tcaaatctgc | gaaataacga | gaggtgtaat | gatcgttttt | 240 |
| aaccaaattt | tttgattcta | atccttccca | cagttttgaa | attcagtaag | catttctttt | 300 |

<210> SEQ ID NO 26
<211> LENGTH: 300
<212> TYPE: DNA
<213> ORGANISM: Dirofilaria immitis

<400> SEQUENCE: 26

| ttgcaacaaa | tcaataataa | aagacttgcg | gctaacaata | tatttgattc | ttttttaccg | 60 |
| ttattattat | gacaggtaat | aatagtatta | caagcatatt | tgtaggtgtc | aattttttca | 120 |
| attcaaattt | tcttaattca | ttatttcttc | ctttccttaa | taaatagtct | ttccatttaa | 180 |
| gaattaactt | tttgaaatct | ttaatgagaa | gacacaaaag | attccggata | attttgcatc | 240 |
| atcttttcta | tttcgcgtta | gtattttatg | ttttcaacag | attttttatga | tttaactata | 300 |

<210> SEQ ID NO 27
<211> LENGTH: 300
<212> TYPE: DNA
<213> ORGANISM: Dirofilaria immitis

<400> SEQUENCE: 27

| gataaaatgg | gttcttgtca | agctcatttg | gcatatcttc | gtcttctata | tttatatcct | 60 |
| ttaatatctt | ctctttttc | aaattttcct | tcccgacgtt | ttccatatcg | acctcttttct | 120 |
| tcataaattt | atcttcctca | tttgcctcat | ttttgactt | ttcatccgtt | tcatccttat | 180 |
| ttttctttt | ttcatctcct | attttacctt | ttcctttatc | aacttctatc | ttaactttct | 240 |
| caatgttttt | tttattttct | ttcatctttt | tgttttcttc | tattgacata | ctataacaaa | 300 |

<210> SEQ ID NO 28
<211> LENGTH: 300
<212> TYPE: DNA
<213> ORGANISM: Dirofilaria immitis

<400> SEQUENCE: 28

| ttttacgaac | aattatttca | taaaagattc | gtattttga | ttagttttta | agaattttt | 60 |
| tttattattt | ttagccaaca | aatatatttt | tcaaaattgt | taaatttgaa | attataaatt | 120 |
| tcaactaaaa | aaaagcaaaa | agctaagcca | atagaaataa | catacatgtg | taatataaaa | 180 |
| tataaagtat | tcgaaatgaa | aatcaaagtt | tcataacaaa | aaacaaaaaa | tattctaacc | 240 |
| ttttagattt | catcaaaact | tcactaaaaa | gttaaattta | aattttcaaa | ttgttataca | 300 |

<210> SEQ ID NO 29
<211> LENGTH: 300
<212> TYPE: DNA
<213> ORGANISM: Dirofilaria immitis

<400> SEQUENCE: 29

| cgaacaatta | tttcataaaa | gattcgtatt | tttgattagt | ttttaagaat | ttttttttat | 60 |
| tattttagc | caacaaatat | attttcaaa | attgttaaat | ttgaaattat | aaatttcaac | 120 |
| taaaaaaaag | caaaaagcta | agccattaga | gataacatac | atgtgtaata | taaaatataa | 180 | agtattcgaa atgaaaatca aagtttcata acaaaaaaca aaaatattc taaccttta      240 gatttcatca aaacttcact aaaaagttaa atttaaattt tcaaattgtt atacaatgat    300

<210> SEQ ID NO 30
<211> LENGTH: 300
<212> TYPE: DNA
<213> ORGANISM: Dirofilaria immitis

<400> SEQUENCE: 30
tcaaagacaa aatgaagaac ttaacaaaaa aaaggccaat aaataaaggc tatttcgtga    60
aaaatctaaa aaaaaaaaga tctgttcctt tcgaatcaag tgattcttcc tactacattc   120
gtgttgtaat tcttacttgt atacagtccc cagttttcg acgataaaaa acatttcgat    180
aagtgagttt gaattaattg aattttaaaa gatcataaaa ataaaatcaa ataaaaaga    240 ccaaaattaa gtctgataat tccagaaaac acaataataa atatacaaat aataaaaact   300

<210> SEQ ID NO 31
<211> LENGTH: 300
<212> TYPE: DNA
<213> ORGANISM: Dirofilaria immitis

<400> SEQUENCE: 31
aaataattca ctaatttctc atcatcaaat tatttcgtac aatcgataaa tcaacgatta    60
taatagcgaa gagaatgaaa attaatgtgg tgcacacgtat acggacccca tatacaatgt   120
tcaacagaga tgaacatttt ttttctatta agttttctg ttcggcgaaa gaaagacact    180
ttctaacgat gctttcctcc caactcccct tgcaatgata gaggatgcag ccaagattcg   240
tcgactcaag cagcatcact caaccggcca tcacttcggg accttttcc ctgccttta    300

<210> SEQ ID NO 32
<211> LENGTH: 300
<212> TYPE: DNA
<213> ORGANISM: Dirofilaria immitis

<400> SEQUENCE: 32
cattgcgaat gaccgctatg gaatatcaat tagcagatat taatcgtgaa ttaagcacat    60
tggtggaatt tttacgacca aatcgaattt caaaaaatgc tacacttgca acatcagcaa   120
ccattgcaac atataacagt acttcgatgc gtaatgtaaa aagaaatgt aatgcatctg    180 aaagctgaaa attcatctga tatattgaag caaaaggtaa gattatttt aagatatcat    240 tcttgatgct ctcataattt ctacatcaaa tttaatcaaa cgattcattt atgttcattt    300

<210> SEQ ID NO 33
<211> LENGTH: 300
<212> TYPE: DNA
<213> ORGANISM: Dirofilaria immitis

<400> SEQUENCE: 33
ttcttgttgt acctatcata gatgataact taagtaccaa tagcaatagt gcaacgatgc    60
aaggattctg attaatgatt ataaaagttt aaccaatctt cttcattcct tctaatcaag   120
agaaaaaaaa atgagaacat ttttatgaca tttgaagaaa ggcaatttat cgctgaaaat   180
tctactgcga tatggaagta tcagatagag aaaataaata ttaaaatatg gatttcatac   240
gaaaaatgat aaaagataat aatttacatt ttggtgcttt actgatatga ttggagtatt   300

<210> SEQ ID NO 34
<211> LENGTH: 300

<212> TYPE: DNA
<213> ORGANISM: Dirofilaria immitis

<400> SEQUENCE: 34

| cgatatttttt | tggacgaatc | aaacctttt | gggaaatcat | ttgatgtcac | aagcatggtt | 60 |
| tgagaaattt | ttttccgaat | tagttctgct | aaaaatactc | caaatgagtc | tagtggaatt | 120 |
| aagctaagca | ccttaagtaa | gttgagaaaa | acgtttccat | ttgactaaca | aggctagtat | 180 |
| atcgacatga | gacagaaatg | gttattactt | cactcacttc | atgaagcgaa | tacgaaatat | 240 |
| ctgttcactt | tagtttcaat | ctactatttt | accaataaac | gtgttctttt | ccggataaat | 300 |

<210> SEQ ID NO 35
<211> LENGTH: 300
<212> TYPE: DNA
<213> ORGANISM: Dirofilaria immitis

<400> SEQUENCE: 35

| tcttaattga | ttttcttaac | tcgaaacact | tgtcttgatt | actgtgctgt | actttatctt | 60 |
| attaaattaa | ataatttcca | tgaccacttc | ataccattga | ccatcaaact | ttgatgaagt | 120 |
| ttatgtgtga | agtgccaaac | aatcattcat | cccttcagtt | taacttattg | ctggtcaaat | 180 |
| tcataaaaat | gcaaattatc | aagcagatag | taattcagtg | aacgtagcgt | attctcgaaa | 240 |
| tttctttcct | tgtatttacc | ttatatagaa | caacgtatat | ttgtagcata | tattcaatat | 300 |

<210> SEQ ID NO 36
<211> LENGTH: 300
<212> TYPE: DNA
<213> ORGANISM: Dirofilaria immitis

<400> SEQUENCE: 36

| tttctgagtt | tgcgttacag | cgccaaatct | tcacggagat | agataaaata | cttatcgtga | 60 |
| aattttggcg | ccatgattta | aaaaacacgg | agataaaaat | aaaatgctta | tcggtgataa | 120 |
| tttagcgcca | taatatgaat | gaattgaaaa | aacaatttga | gtagaaacat | gacatagagt | 180 |
| tttcgttttc | tggctacgaa | aatggatgaa | ttttctgga | atcgaattca | gtcaaagaaa | 240 |
| taggaacgtt | gttactaaat | gatcgaaaag | cttttctaaaa | ttaaatttat | gacgtctaag | 300 |

<210> SEQ ID NO 37
<211> LENGTH: 300
<212> TYPE: DNA
<213> ORGANISM: Dirofilaria immitis

<400> SEQUENCE: 37

| atctaaatct | tcgttttata | gtggtaagac | ttccatttgc | tgcattcttg | caaattaagc | 60 |
| tgttgaaaat | acttttttt | ttgatagatt | tccaatttaa | tcatattata | agaagaatta | 120 |
| atttcgaata | gaattttaa | atcatttaaa | ctttaagttt | taaaactaat | ataagttatg | 180 |
| cagatttcgc | gaaaaagtct | catttgttaa | ttcaattatt | ccaaaatgta | ataattttat | 240 |
| aaattcaaat | ttaaactact | actaacttct | gaagtcagga | gccagtagca | acaacgtaat | 300 |

<210> SEQ ID NO 38
<211> LENGTH: 300
<212> TYPE: DNA
<213> ORGANISM: Dirofilaria immitis

<400> SEQUENCE: 38

| aactttacat | ttatattcaa | tttttttta | ttttgtttgt | ttttagaaat | ttgaaaatgg | 60 |

```
gtactaatca gtgtcatttg cagcctctta gaccctcttt ataacgaccg attcgatgaa    120
atacgtcatc aatatgccag tttattgttc gggtggagaa tgttttcaaa agttgctgaa    180
gtgatgaagt atagtgagaa tgcaccttat tcagcaccat taagaagtaa attttttgctt   240 tggaatttga caaagacaaa gcaggaagtt gacaacgatg ttctgatgaa acggtttcga    300
```

<210> SEQ ID NO 39
<211> LENGTH: 300
<212> TYPE: DNA
<213> ORGANISM: Dirofilaria immitis

<400> SEQUENCE: 39

```
gtctattttg gctgtcttct ataattcat tttgtaacct tttgaaatat gataaatgta     60 gaaattttt cttcctggtc tataatagtt taataatgtg ttgtagtaat agttttggtg    120
ccgttgaaat atttcaatga tatgctatcg caaaattagg aattcaaatc aaggttacaa   180
gataattcaa aaacaaacaa cgtaaaaatg aaataatttc ttcttcttac ttaccaacag   240
gcatatcatc atcatcctca aattcatgac tatatttaac attgtcatat ttgaataatc   300
```

<210> SEQ ID NO 40
<211> LENGTH: 300
<212> TYPE: DNA
<213> ORGANISM: Dirofilaria immitis

<400> SEQUENCE: 40

```
cgacgcaaaa atctttcaaa ttgtcaccca gttctctaag tgattccaat gatgttggta    60
aacattctgc atgatgtacc gggtaatgaa ctaccaagtt gttttttgct tttaatacaa   120
ctcgcaaaga ttctgaaaac catgaaatta agaaagatta aaataatctg aactctttttt  180 ttcatttttc cttgaactta gcaatatact gagttggata aaatttagaa acgaaatttc   240
gcaaatttat tcagtaaatt caggaaaact cggtttcggt attctaaata taaatagata   300
```

<210> SEQ ID NO 41
<211> LENGTH: 300
<212> TYPE: DNA
<213> ORGANISM: Dirofilaria immitis

<400> SEQUENCE: 41

```
gtttctttgg tttatctcag taagatttgg gcggaaattt cagttatact tttcatttcc    60
atgtgctgtt ttaaatttct tccatattag tataattttc aaataattgt agcgtcactg   120
gtttatttaa ggataacagg ttggactgca gtggctgaga agtgtcttgc cggtcaattg   180
tttgttggtg atcaacttgt acgagttact gatatcgaca tatataatac acggcaaatt   240
ccattcgttt tcagtactgc atcaaaaacg ggattatcgg tactttgtaa atcgcagtat   300
```

<210> SEQ ID NO 42
<211> LENGTH: 300
<212> TYPE: DNA
<213> ORGANISM: Dirofilaria immitis

<400> SEQUENCE: 42

```
gacccctgct cacaaggcag ttcccacaga caatcacaca tctaatcaca cacatcaact    60
catccgacgt aggctatcaa taaggaaaat tgcattgctt tatcgtctaa ctgtaataaa   120
catctacata atgaaattat ttcgccacta tgacaactaa tatcgcccaa tgcaaatatt   180
tgtctcagag ttattccctt ttaacagctg ttgaacgaat agataggacg tcatgtggat   240
gatctacttg tttcaaaggt tgaggtaaca catgaaacac atgaaaacgg taatttaaaa   300
```

<210> SEQ ID NO 43
<211> LENGTH: 300
<212> TYPE: DNA
<213> ORGANISM: Dirofilaria immitis

<400> SEQUENCE: 43
aaagaatggt cagcaagatg tggaaaatcg attactatag ttgaagtatg aatcgaagag    60 gttttttta attctaagag aacgaataat cggcaaagag aaagttgagt aaccttattt   120
tgccttgttt tcagtcaatt tataatatgc ggttaattgt gttaaagaaa gtacaaggta   180
tgaaatctaa gccaagaaat aagagaaaac agctaatgat tatttctgca ttttttcttt   240
ttcgacacaa acttggaacc agaatcaatt gaactagtaa tcagattttg attattgctt   300

<210> SEQ ID NO 44
<211> LENGTH: 300
<212> TYPE: DNA
<213> ORGANISM: Dirofilaria immitis

<400> SEQUENCE: 44
ttagattttg ctgaagcatt gttggttaga tcgatgaaaa tataattatg agagattttg    60
ttgaaattca gcaacaaaat tattattcat gtcttcatgc tgtcagtttt gttttttattt   120 cttctttgac atcggttata ttttgtctt ccaacaatat aaaaaaaaaa ttataatcaa   180
ttggtaatca aattaaaact ctaattgtta gctccctaaa tcagctttaa aaaaataatt   240
gcttaattgg tatttgctac tattagcaaa ctgaaactat ccttttctcg aatggtgaac   300

<210> SEQ ID NO 45
<211> LENGTH: 300
<212> TYPE: DNA
<213> ORGANISM: Dirofilaria immitis

<400> SEQUENCE: 45
atgagctgat atttgatatg catattaaaa atagggtaaa ttacattaag ttagatatcg    60
ttcggataaa ttaattagaa aaaatgttta ccaattagat cgcaatgatg taaaatttca   120 cgtatttta ttcttaagat ttatttgcaa aattcaaaaa tatgtcttat gaaaaataat   180
atttctgtgt aagaacaagg gaccgattca cttgatttat tcgcaaacaa tcgaaattca   240
aaattagtaa ttttaaatat tgctttattc aaaccatacc aataataatt tgagagattt   300

<210> SEQ ID NO 46
<211> LENGTH: 300
<212> TYPE: DNA
<213> ORGANISM: Dirofilaria immitis

<400> SEQUENCE: 46
attgattgat tcaaataaga aatttaaatt atttcccctt ttttcaaaa gatttaacaa    60 atattattta tttgatctcc tcgttcgttc ttatctttt gattatcaat ccatcctcct   120
ccatcatata gctaatttat ttttgcatc gtaaatcaat tgatgtatga ttgatttctt   180
gattataaaa agttagaaga attgaattgc ttaaatttaa ttattgataa tgaaatatta   240
ttatatttca aaatgatacg aagaaatatg acgatgataa gagaaaatat gatatttatc   300

<210> SEQ ID NO 47
<211> LENGTH: 300
<212> TYPE: DNA
<213> ORGANISM: Dirofilaria immitis

<400> SEQUENCE: 47

```
tacgataagt tattttattt tacacatctc catccttgac tagtgtccgt gccgactgtc    60
ggacttgaac cgacaaccta ctaattacaa gtcagttgct ctacccaatt gagctaagcc   120
ggccatctag aatgtgcgac cccgtcgtgg tacatcttct ataatcgttt ggtattcagg   180
actctcttct ttcgtgggtg gaggatcttg atacagttga ctattaaaaa tagggccttt   240
gttagtctgt tacaactcat agacaaaggc gacaatttta gcttacatct tacgttatgc   300
```

<210> SEQ ID NO 48
<211> LENGTH: 300
<212> TYPE: DNA
<213> ORGANISM: Dirofilaria immitis

<400> SEQUENCE: 48

```
atggtagaaa attatatgaa aaatatcat actaaaaata taacagattg ttataaggta    60
tggtttaaga atttacaaca attgattatt tatgataaaa aaaaaaaaag taaatcagtg   120
aatcattaag atagttatga taagcagttt gtattcggta aagcgaatga ttagaggaat   180
tatgggacga aacgtctata acctattctc aaacttttaa tgagtatgac gtgtcttgct   240
tgcttaaaat tatttcaatg atcatttcac tttaccagta tgatcatgat tagacttgaa   300
```

<210> SEQ ID NO 49
<211> LENGTH: 300
<212> TYPE: DNA
<213> ORGANISM: Dirofilaria immitis

<400> SEQUENCE: 49

```
ttagtatcga tattatcaca aatgatatca ctttcatcaa tactggatac gattttatta    60
gtatcataat tttgtggctc gcattccgaa agttttacac gtagaagatt aacctgcaat   120
atgatttatt ttatcatttt cgaatatcca actttgaaat aattcgaaaa tgttgaaaaa   180
ttttgaaaaa ttgttaacaa atattacaa aaatatcaaa tgaaattaaa taactgtcca   240
tttcaaaaaa agaagaaaaa ttatgaaatt accaattaaa aacaggactt attaattaaa   300
```

<210> SEQ ID NO 50
<211> LENGTH: 300
<212> TYPE: DNA
<213> ORGANISM: Dirofilaria immitis

<400> SEQUENCE: 50

```
tgtggaaata aagtacaatt aattgctgtt cgcttaataa tattattttc attcttggct    60
ttttttttct ttccccgtga tattataaaa tatagttttt taattttaac aaatcgtcat   120
aattatttaa aaaatactga ggtgagtaaa tgtaattggt tgctggaaaa aaagtgggtg   180
atgagaggtg aatgaaagca gaatagttta tgattgcatc aaatttcctc cttaatctgt   240
gattaaaatc aaacaaaacc cgaaaagttt cttcttcgcc ttttcttct ctttgtttca    300
```

<210> SEQ ID NO 51
<211> LENGTH: 300
<212> TYPE: DNA
<213> ORGANISM: Dirofilaria immitis

<400> SEQUENCE: 51

```
cgaaatccgc cgcgtgcatt actttgcgct tgttgattac gacgcatttg ttcgtcgttg    60
ataaccttat caatcatcat acgtccgtta cgtatgcaat caacatcgcc agttaggctg   120
aaatcaaatg gatggcgatg atatcaaaaa caaaaataag gagtatttgc tgaatcattt   180
```

```
cttttttctgt attattatca aaattttctc ctttccattg tttccttctt aatcaagtga      240
atgctcattt cattttgaaa taatccaacg taataattcc ccatattccc aattactttc      300
```

```
<210> SEQ ID NO 52
<211> LENGTH: 300
<212> TYPE: DNA
<213> ORGANISM: Dirofilaria immitis

<400> SEQUENCE: 52
agaaatatta aactttgaaa agatgtgaca tgttctgtaa caaaagccca aaatttcgac       60
tgctgcggct tgaagtaaaa ttttggaata tgctacatca gtagtgcaac agatggttcg      120
ataaatagtg gtaagtgatg ggaatcctag gaatagatgg gaattgtatt tcagatataa      180
atttgatgca tattttcata gttgattata tctacgatca cacgttgaat attctaaaag      240
caaactgtaa ttaactaatt gaatttgaaa atttccaaga attaaaattg gtaacaaaaa      300
```

```
<210> SEQ ID NO 53
<211> LENGTH: 300
<212> TYPE: DNA
<213> ORGANISM: Dirofilaria immitis

<400> SEQUENCE: 53
attgtcagga atgagaagca agttttggat acttaaggga tgaatggaac acatacatgg       60
cagaaaatgt tagtaatcaa accatttaaa ttacttagcc actatgctaa actttctaga      120
agtatggttg aacgttaaaa accttcgca aaaattgtat tagattatct taatcttccc       180
tacatcaaaa cagagaattt ttgttctacg acgtgagtct gcatgtatta aggaagttcg      240
tatcatgacg taaatatcct gagtgattat tgaattcaga aatgagcttt tttcatttgg      300
```

```
<210> SEQ ID NO 54
<211> LENGTH: 300
<212> TYPE: DNA
<213> ORGANISM: Dirofilaria immitis

<400> SEQUENCE: 54
atatgagtgt tacatgtgta cgttacatgt aaatattata tgttatatgt aaaaatgtca       60
tgtatagcat ctattcacgt gtacgtacac gtgtatatac atatacattg atacttaata      120
cgtatacgca tgaatgaaca gatattatat atttacgtac actagactca catgtacctc      180
tgtatacgca tacatgtaca gatatatgtt tgacatacgt aaattcatat atgcttttat      240
ttatgcttat attaattgtc acatacatgc cttatatttt cgttgttata aacacataaa      300
```

```
<210> SEQ ID NO 55
<211> LENGTH: 300
<212> TYPE: DNA
<213> ORGANISM: Dirofilaria immitis

<400> SEQUENCE: 55
gaaaataaaa ttagctgaaa atatatgcga ggtaaagcac acagaagaat taacttaagg       60
taatatattg taagaatttt tatattcggc gcacctaata atttttagac cgcatatgcc      120
cagtatttga aactggtagc gctgttcgta cttgctgttg tccatgttat gtatatgata      180
ccattcctaa atacttttgc ggctgtggtt tccagtgttg atgtgactgg tatgatgcct      240
aacactggat ccttccatct gcggcatttt gttgaaattc ttattgatgt gagctgttta      300
```

```
<210> SEQ ID NO 56
```

```
<211> LENGTH: 300
<212> TYPE: DNA
<213> ORGANISM: Dirofilaria immitis

<400> SEQUENCE: 56
caactgtgaa tcataaacat tacttaaatt aatgaagcta gttaacgaca aatatatttt      60
tttatgtatc agtgctatca tataacataa aaacttactt tcattaataa atgagctcaa     120
atattgactt ttgtccaaaa tgctcaaaat gtcgtcataa tatttgaaat gaagataatt     180
tcacgctttt cgaagcctcc tctcacgtct tttaatcttc ttttcttctt cttgctctaa     240
tggttctgcg aaaaaccacg gtgcaataat cactttccat aatttataca gtacataagc     300

<210> SEQ ID NO 57
<211> LENGTH: 300
<212> TYPE: DNA
<213> ORGANISM: Dirofilaria immitis

<400> SEQUENCE: 57
ctgcttaact cttttcattt ttcagagaat cttctctaaa attgtgaatt gatccaaacc      60
aaagaatatg ataatgtga ttcgaattcc tggaatttag attttgagag ttttgaagtt     120
tttaaagaga ttgaatttct gtgaccttct ggtatatttg atgtcatttc gggatgcgta     180
tttttgccga aaattttggg cctcactgca atcttgttaa aagtcaaaaa aattcaatcg     240
tagaatttcg ggtttacctg atattactgg aaatctctga tctttgttct agattgctgt     300

<210> SEQ ID NO 58
<211> LENGTH: 300
<212> TYPE: DNA
<213> ORGANISM: Dirofilaria immitis

<400> SEQUENCE: 58
ataaagaatt tgcaactctg tatacctttt tgcagtgcaa aagcggatga attcttcact      60
gcagtgtgac agattccttt gataaaattg cttcgttctt atgtaaactt ggaaattctc     120
ggtagttatg cttttgctag ttgaaaatgt tctgctcttg taaaacatgc aaaaagagat     180
tatctttgtt ctattatgga aagattcttt tgaaattttg acgactgaga agacaaattt     240
tatcccaact tgtcatctgc aataaaaatt tttcctgacc tgtttcttaa ccttccaagt     300

<210> SEQ ID NO 59
<211> LENGTH: 300
<212> TYPE: DNA
<213> ORGANISM: Dirofilaria immitis

<400> SEQUENCE: 59
aaaatcaaat caatatgatc agataactca tacttatctt actgaaaatt cctcattcaa      60
gggaaataaa taattgcaat tcttgattcc gatcatggat gattttcaag caaattacca     120
atgatatcta tcgataacga ttacagcata cagctataac ttattattga ttgaattgat     180
gaaaataatt ttaccagaaa tttatcaatg tttatctcat tgcagtatac gatgtttagt     240
gtgacaacac ttttttcttgg aataattgtg cataaatcat tgattgcatt agtattgga     300

<210> SEQ ID NO 60
<211> LENGTH: 300
<212> TYPE: DNA
<213> ORGANISM: Dirofilaria immitis

<400> SEQUENCE: 60
tcctgcccac attctttcta ctttagataa tcaacaggag ttagttgaaa gagaagacta      60
```

```
ggaacagttg caacttctga atctttctga ctttctttcg ttttgtaaat tatttatttg    120
tataaattta aaattcgaag agaaataatc caaggtccaa cttctttttc tgttagttct    180
tgcgaatgct ccatcaaaat gcaaaaatat gattagaatt ctgatggaaa ttaacaaaat    240
cgattagata agaaaagtac aaaacagaaa ctaacttttt ctcccatttt catattatag    300
```

<210> SEQ ID NO 61
<211> LENGTH: 300
<212> TYPE: DNA
<213> ORGANISM: Dirofilaria immitis

<400> SEQUENCE: 61

```
tcattgcttt aatactttt aacgagaatt ttctcgatca aaataagatc tgcaattgat     60
atacgtcaat aagcgaacat tagctgtatt acacgctaat attcacatat gatgaacgtt    120
gtaagcgtca tacatcaaca tatatccatc cgataaataa tgaccactac acattgctac    180
caaccatcct atcccgccac tatttgaaat gaactgagaa ggagttatcg acacaggctt    240
cctagcaacc aaacaaaaga cgagacagat gaatagatag acagacagac gaacatacaa    300
```

<210> SEQ ID NO 62
<211> LENGTH: 300
<212> TYPE: DNA
<213> ORGANISM: Dirofilaria immitis

<400> SEQUENCE: 62

```
agattctggt tattattgta tttctgattt atttaatccc aacttaaaga ttcattggct     60
attgtttagc atctatatca attttataaa taaatagtaa tacctgatga aaagcaataa    120
ataattagat gcaaatttta attagataca gtttgatgga aaacattgaa gccatgtaca    180
actaatttat gcatgttgaa ttatgcatgc ataattaatt tatgcatgac agcaagtttg    240
gtataaaatt aattttgtat gaagataaaa ttttataaat aatgataata atgctggtaa    300
```

<210> SEQ ID NO 63
<211> LENGTH: 300
<212> TYPE: DNA
<213> ORGANISM: Dirofilaria immitis

<400> SEQUENCE: 63

```
attattgaaa agaataatgt agctaattag ttgaagctgt taaaagtaaa gctaaaaga      60 tgatggaaat tattcgtata acattctttt gtaaacaaac agtcattcct gtgaataaac    120
aattataatt ataaacaata cttttcaaga caataaaaaa attaggaagc attgttgtga    180
taatcaatag ttgatagact gtcaatgtat tttatcagt cgtgctgctt ttttcccctt     240
tcttgactca tttattttat tatttattga tagaatgtca atattctagt catttgttat    300
```

<210> SEQ ID NO 64
<211> LENGTH: 300
<212> TYPE: DNA
<213> ORGANISM: Dirofilaria immitis

<400> SEQUENCE: 64

```
atcttaactt gctttaaaca aataaattaa aacagcccaa tgttccaaga aaaaagata      60 agttaaaagt ggggtgtcca aaaatttatg aattgaattg acagttatt cagatcctga     120 aaatacgctt ctctgatcac tgcaaatatt cccgataaat aagtgaacat taggttaatc    180 ttaatttcc cttaactttc cttagccttt tttaaatttt tggattattc aagcattttt     240
```
attgcggtat cgtttttgta aaaaaaaaag tataattcaa cattcaggct cgacgttatg      300

<210> SEQ ID NO 65
<211> LENGTH: 300
<212> TYPE: DNA
<213> ORGANISM: Dirofilaria immitis

<400> SEQUENCE: 65
aattaataaa agaaaggaa tacgataaaa tatctatttt ttgaaactaa tcaaacatat       60
tcctcactgc tcaccggata gttgctttct aattttacat taagaaatat attttttttt      120
ttcaataagg aaagttatgc agactaggag aattctactc tgaagaagag ataagcatgt      180
tagaattatt aaaatctatg gaaatatcct taaaagaatg cctatagtag ctctgatttc      240
gaaaaaaaaa gcaaaaaaca aataacaaa ttctgctcaa ttgaaataaa aaactttcct      300

<210> SEQ ID NO 66
<211> LENGTH: 300
<212> TYPE: DNA
<213> ORGANISM: Dirofilaria immitis

<400> SEQUENCE: 66
taaaatatct attttttgaa actaatcaaa catattcctc actgctcacc ggatagttgc       60 tttctaatttt tacattaaga aatatatttt ttttttcaa taaggaaagt tatgcagact      120
aggagcattc tactctgaag aagagataag tatgttagaa ttattaaaat ctatggaaat      180
atccttaaaa gaatgcctat agtagctctg atttcgaaaa aaaaagcaaa aacaaaata       240 acaaattctg ctcaattgaa ataaaaaact tccttcaac ttccagcatc actgctgtga       300

<210> SEQ ID NO 67
<211> LENGTH: 300
<212> TYPE: DNA
<213> ORGANISM: Dirofilaria immitis

<400> SEQUENCE: 67
aactgctaaa aaattgaaac tagtgttaga ttgataagtg ggcagattaa aaccaattgt       60
gttattggcc cgttaattag tgactctgaa tagctatggc gaatcgtata gtgttgtacc      120
gacgacgtat ctatcaaatg tctgccttgt taaatttcga tgatagttta tgtgcctatt      180
atagttgtaa cgagtaacgg agaataaggt ttcgactccg gagagggagc ctgagttgcc      240
acattcaagg aaggaagcag tcgcgaagat tacccactct tagaatgagg aaagagtgac      300

<210> SEQ ID NO 68
<211> LENGTH: 300
<212> TYPE: DNA
<213> ORGANISM: Dirofilaria immitis

<400> SEQUENCE: 68
gaaaactaag aagtaagtga aatttctaag ttctttccca gaaaggttag atccaatatt       60
tgttttcatt ttagcatttt tatccaatga aaaatgtgcc caataaatac ttgtatatag      120
tattgcattt aaaaacttca gaaagcacaa tgagatctaa gctcagaaat atgacgaata      180
ccaatccttt tcctagtctt accgcttctt aactttgtg tcgctttata aaaattaaaa       240
ataaaaagtt gaacaatggg aattacatca ttttcatctg aatggtttat ttcctattct      300

<210> SEQ ID NO 69
<211> LENGTH: 300
<212> TYPE: DNA
<213> ORGANISM: Dirofilaria immitis

```
<220> FEATURE:
<221> NAME/KEY: misc_feature
<222> LOCATION: (36)..(45)
<223> OTHER INFORMATION: n is a, c, g, or t

<400> SEQUENCE: 69
cttccctagc tatgccttt  cgtcacttaa gcttcnnnnn nnnnntctag ctacgtatcg     60
ttatcattta tgcttcttta gctacgtttc tccatcattt atgcttccta agctacgtat   120
cttcatcact tacgcttccc tagctatgtc ctttcgtcac ttaagcttct ttggctgcgt   180
gtcttcatca ttaatcttct ttagctacgt atcgttatca tttacgcttc cttagctacg   240
tctttccatc atttatgctt cccaagctac gtattttcat catttatgct tccttagata   300

<210> SEQ ID NO 70
<211> LENGTH: 300
<212> TYPE: DNA
<213> ORGANISM: Dirofilaria immitis

<400> SEQUENCE: 70
gatcttaaaa ttctatgaaa cttcttctgc atggtattgt ttccaacaga atataatgac     60
aatagcaaca gtattggtta tataaaaata ttgactgcag caggattata tttcaagttc   120
ttttaatttc atttatttat tctttcattt acttttactg ttttatgtt  tttcttcttt   180
aaaaaatatg atttctctca ctgttctctt tcatctatct atatttattt gataattgct   240
tatatgataa ctagctaaag ggaaataaac tttcagtcat catagcttca ttttagtaaa   300

<210> SEQ ID NO 71
<211> LENGTH: 300
<212> TYPE: DNA
<213> ORGANISM: Dirofilaria immitis

<400> SEQUENCE: 71
ctatactaat cagtccacta tccattttta ggttgcaaaa gttgcaatga cggtttgatt     60
tcatcctcca atgcaatttt gagtctcaat ctcgagagat agatcgatcg cttttagctt   120
gatttagctt ggttaatgtt gtgagggata ttgggcagaa attctgtcaa gcgttactta   180
atgaaatagt aaatgatcac tgatatttat tgttaatgat acttgagctc tctagattat   240
gaactggaag gttttcgata gaaataatcg atacatatat tagaatcgac ttctttttc    300

<210> SEQ ID NO 72
<211> LENGTH: 300
<212> TYPE: DNA
<213> ORGANISM: Dirofilaria immitis

<400> SEQUENCE: 72 tcatctttt  cacatttcat ttaatcatca ttttatcaat tcctattttt aaacaaattc     60
ttttcaaata ttctctcttt ccttctcttt ttgttttccg cttattcatt ctaatgatga   120
acagatgtag aaaatttgca ttctattgct cactacaatt ttgagtagaa tatatttaat   180
tatttgattc gagacagatg gttatagcct ttagcttcag cttctcgttc aaattaagta   240
cttgtgacct ttccaagtac cattaaagct ttcctgcgtt tcctaattag aaaaaaaagg   300

<210> SEQ ID NO 73
<211> LENGTH: 300
<212> TYPE: DNA
<213> ORGANISM: Dirofilaria immitis

<400> SEQUENCE: 73
```

```
gcattttaag ttaaaagtat cacgctgcat gacacctcac gtttgctatc tcaaattgag      60
taggttagaa tcttttttg gctactattc aaatattaat aataaattgc tgcaaacaga     120
tttcacaccg gaaaaaaatt aaattttct agcaatgttt taactcccctt attaaatatt    180 tatagaaaat cgactactta aaagaattg actaacattt ctgaatctct gcagagattt     240
atagatggat tagcatccta caagttttta tcttttgct atatttccat tatttttta     300
```

```
<210> SEQ ID NO 74
<211> LENGTH: 300
<212> TYPE: DNA
<213> ORGANISM: Dirofilaria immitis

<400> SEQUENCE: 74
```

```
gataagacgt cttattttgt aataattcaa aaattaatta atatagaagt aagatcttga      60
taataattaa tatgctcaaa tttcttaatg agaatatgtt caggatgaag atgaagtgaa     120
agaaattgat agattgagga agcaattgct aattgaaaca gaacagctcg tttccaattc     180
tcttaaagat ttactgaaga aaattattat tccacttgaa gaagctattg atctcaaaat     240
tcatcagaaa ttaattcaac aaattgctgc cttgttgaag tgtattagta cttggataa      300
```

```
<210> SEQ ID NO 75
<211> LENGTH: 300
<212> TYPE: DNA
<213> ORGANISM: Dirofilaria immitis

<400> SEQUENCE: 75
```

```
accgcaaaat acctaaaaat ttctataaca acgattaaca cggcctcgaa ctggaagcat      60
attaatccat gcgtggctca aacttcaatc ataaagacaa gatctagaga tcaacacaaa     120
atggtgaatt gttaccctat cgttgctaaa gtttgagaga aaaagtgct aaatcaagta     180 gtacaccaaa tttagttaat attaagaaat caatttagta ctgaatttaa acaaatgaaa     240
ttttacgata aaataaaaaa gtacctgatc aaacagcgtc ctcccgttat tcccattgct     300
```

```
<210> SEQ ID NO 76
<211> LENGTH: 300
<212> TYPE: DNA
<213> ORGANISM: Dirofilaria immitis

<400> SEQUENCE: 76
```

```
tataagacta gtaaacagat cgtaatataa taaatatcga ttttatttta aattttcgaa      60
aacttccaaa tctatcgata tgaaattaaa gatcaatttt taatttccat aatatattta     120
gattctatcc caacatcact catctttatg tcaacttatt taattctctt attaacatta     180
tatttcttgt ttacaatgat aaattttatc aattttctaa tatgatagaa catcttcatc     240
atctgaagat atgcttttct catctttgta acaattcgta tcgcttctga ttttactttc     300
```

```
<210> SEQ ID NO 77
<211> LENGTH: 300
<212> TYPE: DNA
<213> ORGANISM: Dirofilaria immitis

<400> SEQUENCE: 77
```

```
gttttattat tgcttattga atagtgataa taacactttg atatgatatt gttttgttgc      60
gatcattgta ttgattataa ccttaattaa acgaggatat tatgggaaat gtatttatta     120
caaaattaaa tatgaaaggt tgaagtcttg acgaaacttt caaacacatt tctcgaattt     180
tctctgcaaa aatatcgtta cgatttttgg aaattatgaa gtccaagaat tcaatcgaga     240
```
gttcgccatg tcactttggc tagtttcgtt tgttttaat atttcaatca aaagtcaatt    300

<210> SEQ ID NO 78
<211> LENGTH: 300
<212> TYPE: DNA
<213> ORGANISM: Dirofilaria immitis

<400> SEQUENCE: 78
ccttggatat tgttcttgac atcgttgatc agaaggtcac cgtagtgttc ggtgagcgag    60
atggaattgg actcaggttt attctccgtt tttttcatgt ttttgaattt tagagagaaa    120
ataatgtttg tctgaatggt tagcaaacta attagttttt aagttatcag gaactcgaag    180
tatcttcttt tgcacttctt taaccttttt catcaaattt tttaacagta acaagatttt    240
tttgagaatt ttcaaaatat ttttgacttc tgatgatatt tgatgagaaa accatcactg    300

<210> SEQ ID NO 79
<211> LENGTH: 300
<212> TYPE: DNA
<213> ORGANISM: Dirofilaria immitis

<400> SEQUENCE: 79
agagtattat tatacatgat gatgatgatg atgatgatga tgatgatgat gatgatatga    60
tgatgatgat gatgatgatg atatgatgat gatgatgata atgataatga tgatgatgat    120
gattaattgc ttatttttaa tgattgataa ctttaaaaga aatcattgaa atttgatcga    180
ataaaaattt tcttaaaaaa agcatttgct atttatatag taaacctata aaaaattact    240
tatttttatt actaatattc atttgattgt atgaaagaga agagaaaaaa aacctttgca    300

<210> SEQ ID NO 80
<211> LENGTH: 300
<212> TYPE: DNA
<213> ORGANISM: Dirofilaria immitis

<400> SEQUENCE: 80
tggtatcaca gcactgggtt taatttcaac aatcggttga cgatcttttc gggatatgcc    60
tatacccaga aatgaacgta tgccaaacga tggtatgttt gatgcaacag acgacgtcaa    120
cttaaaatgt gtttttttt caaaaattca atatttttag tttaaaattg cacgtcagta    180
aaaattaatt cataataaat ctctttgatt tcttcgttct cctttttttt cagaaaaaat    240 tgaaattta catacctgat ttccaagagc atataaagca tcacttaaag cattctgcga    300

<210> SEQ ID NO 81
<211> LENGTH: 300
<212> TYPE: DNA
<213> ORGANISM: Dirofilaria immitis
<220> FEATURE:
<221> NAME/KEY: misc_feature
<222> LOCATION: (263)..(272)
<223> OTHER INFORMATION: n is a, c, g, or t

<400> SEQUENCE: 81
tccttttcat gatttgtagc taaccaataa gatgtgtata tgttcatata tttactctcc    60
cctgactctt ttacactctc attctctcat ttgttcattt agataagtaa tatgcgcctt    120
tctcttcctg attctctcaa tctttcatcc cttcatctcc tcaatctttc tcccattctc    180
tcaatctttc ctgcattgca ttcattgatg aaacacgata gtattaataa gcataatttg    240
ataaattgaa ataattttt ttnnnnnnnn nntcattctc tcaatctttc ctgcattgca    300

<210> SEQ ID NO 82
<211> LENGTH: 300
<212> TYPE: DNA
<213> ORGANISM: Dirofilaria immitis

<400> SEQUENCE: 82
tttgaattaa caaaatatta acaattacaa ctatttcgga atttaattta agaataattt      60
aattaatcaa tttcctattt tgtatttaa aaattaccac ataattatg taattttgg       120 gatatttgaa actttgaaaa agtggtatt gtatttgaga ataaattaat taatgtaatt     180
cttgctgctc atcgttccat aacttacaaa tatttctcgg tatttttattt gagataattc   240 ttatcatttc ttccatagct ttcaatatat ttataactta tttgtaatca ctcttatcac    300

<210> SEQ ID NO 83
<211> LENGTH: 300
<212> TYPE: DNA
<213> ORGANISM: Dirofilaria immitis

<400> SEQUENCE: 83
ttgagatatc aaatcaagcg ttgcatattt atagtacact ggtgtagctg aaatcgcgaa     60
gagaacacga aaatcagaga agtcaatggt tcctttgtgt tggatttcac atgaaagcat   120
ccttatgttg tacatgcgtg attacaatat gatacaagat gtaagctaaa aattgtttta   180
tctttgtcta tgagatgtag ttcatactct ataataaagt cccaaccctt aattctcata   240
ttcacaaccg tatcagaatc caacaccaaa ccattataaa gaatgttctt cgtcgaggcg   300

<210> SEQ ID NO 84
<211> LENGTH: 300
<212> TYPE: DNA
<213> ORGANISM: Dirofilaria immitis

<400> SEQUENCE: 84
ccactatcgc ttacactttc tttatcctgt tcttcttcat ctttcgtttt ggactttatt     60
ttactgtcag gtgacaagca aagtaacgat gttggacttt gcgaagatgt ggatggtacg   120
ctagaaaaaa aatgaggatt ggttaatatg tctaattatt acatcgcttt ttttaaatc    180 ttttctaaaa ttaaactgaa taatcaactt atttgctatt cagtttatct tatttttat    240 caacaaaatt cgaggaaaca aatcgcttat cagaataatt gttttgatca acaaataaag   300

<210> SEQ ID NO 85
<211> LENGTH: 300
<212> TYPE: DNA
<213> ORGANISM: Dirofilaria immitis

<400> SEQUENCE: 85
caatcccaca aattcagtgt gtcggcgggt cagcgaaggg aaagtttgaa ccgagggtat     60
gtacaaattg tgataatttt tgtgatgacgt agtaaattc atagttttgc atgctttaat   120
gttgatagtc gcacaatcct acgttgatta aatttagcta ttagatatcc tactaaatta   180
tgttgttcat aatttttgtt tttaaaatgc tccacttata ttttcaggtt gtgcagtgct   240 acaataggg ttatgacggc aatgatgtcc aatgggagtg taaagcggaa atgagcaatc    300

<210> SEQ ID NO 86
<211> LENGTH: 300
<212> TYPE: DNA
<213> ORGANISM: Dirofilaria immitis

<400> SEQUENCE: 86

```
tcagataaat tgtatttgat gttaattcaa agaagaaaaa aataatcagt agaatatgaa      60
tcgaataata ttcatacaac cagtttattc attattattc acttttaacg tctaaatgac     120
gtagctacgc ttttttctc gctttcaagc ctttactgac caagattaat gtacattctg     180
ttgaacaaga ttaatcgaca ttctatcgat caagatcaag cttttactga tcaagattaa     240
taatgacatt cttctgttga tcaagattaa tcgacattcc attgatcaag attaatcgac     300

<210> SEQ ID NO 87
<211> LENGTH: 300
<212> TYPE: DNA
<213> ORGANISM: Dirofilaria immitis

<400> SEQUENCE: 87
ctctctaaaa cctattggtc actaaacttg cactgactaa aaactattgg tcatcagact      60
tgtgattcat tgaaaagacc gttagccgct aaaattatga ttcactaaaa aaaatctatt     120
gatcattaaa tctgtaatca ttgagaaact acaatcattg gtcattaagt ttgtgctctc     180
taaaacctat tggtcattaa actgactaaa aactattggt cactgaacct agagtctatt     240
aaaaaaaaaa tcattgtatc aataaattta ttgtttacta tcaaatccat tgattactga     300

<210> SEQ ID NO 88
<211> LENGTH: 300
<212> TYPE: DNA
<213> ORGANISM: Dirofilaria immitis

<400> SEQUENCE: 88
tctaaaacct attggtcact aaacttgcac tgactaaaaa ctattggtca tcagacttgt      60
gattcattga aaagaccgtt agccgctaaa attatgattc actaaaaaaa atctattgat     120
cattaaatct gtaatcattg agaaactgca ttcattggtc attaagtttg tgctctctaa     180
aacctattgg tcattaaact gactaaaaac tattggtcac tgaacctaga gtctattaaa     240
aaaaaaatca ttgtatcaat aaatttattg tttactatca atccattga ttactgaata     300

<210> SEQ ID NO 89
<211> LENGTH: 300
<212> TYPE: DNA
<213> ORGANISM: Dirofilaria immitis

<400> SEQUENCE: 89
aaaatgtatc aaattcttcg atgccataaa ttatacagac ttgattggca tttttctaa       60 ctttcatcat gaaccattct atttctaaat tgatccatta caaaatcaac tttgtgatat     120
catcaatctc agtcataacg agaaataatg ataatataaa gcgactatca tttgaatttc     180
ctgaatattc aagatgtaat tacatctttt ttttaatgta atcaaaattt cttgccatca     240 ataattttc aacatatgct ttcatcgact gccttatgca gatcgtaatg atgacagcca     300

<210> SEQ ID NO 90
<211> LENGTH: 300
<212> TYPE: DNA
<213> ORGANISM: Dirofilaria immitis

<400> SEQUENCE: 90
attgattaaa aagaatcaac attaaatttt tgatatagtc gagaaatcct tcgtgataat      60
tcttttagaa caattcttta cactaaactt gtatttactt gcttattatt tgtctaaaga     120
tactaactat ttgtcagtgg aatttatgat cttggcatta ttgcatataa cgctttccta     180
```
aaatctgaaa tttttcagta ttttaaaaac taagacgatt attaaatatt actcaaagct     240
tagaactttg attatactaa tcaaatcaaa aatttcatca gcgattttg ttgtgtcatt      300

<210> SEQ ID NO 91
<211> LENGTH: 300
<212> TYPE: DNA
<213> ORGANISM: Dirofilaria immitis

<400> SEQUENCE: 91
atttttccca gcagaattgt catcaaaaat cccattttg atatcctctt catcgaaact      60
tgctcctgaa tccagagaac aacgaagaat gtgtaaatct atttcagtag cctgctcatt    120
gtgcaattca gcgactttat ttctgtgctt caagctaact tcttcattat gccactcctc    180
ttctctcgct attttttcgc tatctaattc aaaatcttcg tctgaaacgg aatcaactcc    240
tgacgatgta ctcgacactg ataatatttt catgccgatt tttctctcaa cgaatcttt    300

<210> SEQ ID NO 92
<211> LENGTH: 300
<212> TYPE: DNA
<213> ORGANISM: Dirofilaria immitis

<400> SEQUENCE: 92
gaatgaagag caaaaaaata gtcacgacca cctgcaataa aaacagcatc tccgtaaaaa      60
tgattgaatt gattcccgaa atacgagttt atcaaattga gaattatgca aattaattat    120
cagcatgcag atttactgat tttatatctc tcataccgaa attaaggtga tgttttccat    180
ttctttgttt ccacaatgtc ttctttgtga atcgttttgg atcaactatt aatccgatcg    240
aatcaatcct ccaaatatga gtttattcaa cgtaacaaaa cattgtccga gataatcaaa    300

<210> SEQ ID NO 93
<211> LENGTH: 300
<212> TYPE: DNA
<213> ORGANISM: Dirofilaria immitis

<400> SEQUENCE: 93
tggaaatttc gaaatcgaaa ggatgaagaa aaaggatcct tgatctatac attaaatatc      60
accatatcaa ctagcatggc aagtcaaagt aatgttatca tttaaataaa aaagatgaat    120
agtaggacta caggttatat tgttaaaagt cgacaaattt ggagtaattg acagagatca    180
acgattaaat gtaatggatg atcttatctt ctttttttcaa ctacgccaaa atgaaaataa    240
caattgaatt tgtcgaataa gaaactaaca ttttgaaaat aagattgaac atttataaat    300

<210> SEQ ID NO 94
<211> LENGTH: 300
<212> TYPE: DNA
<213> ORGANISM: Dirofilaria immitis

<400> SEQUENCE: 94
ggttggatca ttatcgacag aactttagaa gtttcttgat aaggacgaaa agaagcagca      60
ccattgctga tctaaacaag gaaaaaagac cttttttgga atattgaagt ttttactgat    120
aggtgcgtgc tgtgtactgt gggcataagt acaagcttca tgctccgcag cgtgaatacg    180
tgctgcatgc atactatgca gtaaaggtgc gtgtcgtatt gctcaataag tgtataaatt    240
gctgcttttc ttgcatagtt aaatattttg ttttcatttt ttccgctatt caaaataaat    300

<210> SEQ ID NO 95
<211> LENGTH: 300

<212> TYPE: DNA
<213> ORGANISM: Dirofilaria immitis

<400> SEQUENCE: 95

```
gttgggattt cagactctca ctcggtgtcg tttcacagtg atatctgaat cgaagtcaca    60
agcaggtatg aatgcataac aactaatatc cattgcagaa acaaggcaaa actgagaagc   120
tcgagcaata tagctataga agctggtacc acagatgaca ttacatggta tttccatttc   180
agcttcacaa acattgtaaa tagcttgctt cgatgattca atatctcgtt ctacgatatt   240
cttaaagtaa ttttattta tttgaagtat agattacatc catgttctat ctatcatttc    300
```

<210> SEQ ID NO 96
<211> LENGTH: 300
<212> TYPE: DNA
<213> ORGANISM: Dirofilaria immitis

<400> SEQUENCE: 96

```
tgttctgaac atctcttttt gattatcttt tttaattcct ccattatttt cgttttttc    60
gttgtgaatt aatattgttt gtctttgatt cagatgatat tttcggatcg taaatagatg   120
gcatcggcat aagcgtattg agaagcattc aatggtgcac tcttgcttct ttttttttg    180
aaatctttct cgataatcaa ataagtgcag gatgccaatc attaacaatt cgttccact    240
ttttcagttc ttattcttat aacaccacat ctcatttgca attttgtcgc caatgatttt   300
```

<210> SEQ ID NO 97
<211> LENGTH: 300
<212> TYPE: DNA
<213> ORGANISM: Dirofilaria immitis

<400> SEQUENCE: 97

```
tttttcgag gtcactctgg aaaataaat catattttaa aaagacataa aataaaaat      60
atgtatatat aagaaaattt ttactctgaa tttcttaaga aaattctcga ttctgttttc   120
cataaattcc ggaatatgtt gtccctgaat taagaattcg attccttgca caccattatt   180
tcgtctagtt cctgtgtgaa caatgtaacc tggaaatgaa cacataaact gtaatatttt   240
gagcttaaaa taattatgag gatgcgaaac tgaagatatt cataaatgtt taaaaaaaaa   300
```

<210> SEQ ID NO 98
<211> LENGTH: 300
<212> TYPE: DNA
<213> ORGANISM: Dirofilaria immitis

<400> SEQUENCE: 98

```
gtccatgcat tgcttttcgg aagttagtgt agattcagtg aatatttaat accagtctct    60
ttctaattca aaagagcctc ccatttcttt tttcagtttc agtctctgaa tcagagcgtg   120
taatctacca ctccattgcc gaaaacagct cgatgtattt cctgctacgt agtgtttaga   180
attggcgtat gccacttgct cattattcgc gcatgaagtg taactgtgaa tagaatgata   240
ctactgttag aagagaatgc gttcacttta tttaacatta tactgattca tttcttcttt   300
```

<210> SEQ ID NO 99
<211> LENGTH: 300
<212> TYPE: DNA
<213> ORGANISM: Dirofilaria immitis

<400> SEQUENCE: 99

```
agtgaacgag aaaaaacaga agaagagata gcacatcaag atcgtgagaa attaattaga    60
```

```
caagaaaaag ctcgtcttac acaaatatat caggttttct ttttcttgct ttcgaaagtt    120
atttgaatta tctcatttct ttgaatttta taagaaataa tttaatttt ttttgaaatt     180 ttgcctattg agctctaaat tttgtaaaaa gttttctagg atgatgttag caaagcaaaa    240
aagaaatcca aaagtgatgg taacaaacag gaagatttta tagtgaggta cgataatacg    300
```

<210> SEQ ID NO 100
<211> LENGTH: 300
<212> TYPE: DNA
<213> ORGANISM: Dirofilaria immitis

<400> SEQUENCE: 100

```
tagacaatat catccttcct ttttttttgc tcaatttctc tgctcattgc tttgatgata    60
atggtaggtg gtataatgaa acgaatagat aattgatgtt cgcaaacatt tgctgttaaa    120
tttcagtaaa gaaattgacc ttttgctttt gtgttggatg tttagcttca ttttcttctt    180
gttcattgtc atattcattc tctcaaaact tcttgcttag cgatgctaat ataaatactg    240
gaagaatgcc tttgctttgt tttagttgta atcatcacc aaggtatttt tttgcaaaat     300
```

<210> SEQ ID NO 101
<211> LENGTH: 300
<212> TYPE: DNA
<213> ORGANISM: Dirofilaria immitis

<400> SEQUENCE: 101

```
aagatgaaac taaaaaaaat tatttcgaaa aaagaaaat aaaattaatg aaataaaagc      60
aaaaatgaac aaaccgtatt aattttaaac aataaacaat atcgaaatcg aaaaatggac   120
tattattgat gaactatatt ttcaaaatgt gaaaggtcaa agtttgtttc aattatgata    180
aatacaattt aaaataagat taagctaaca aataagttga gcaaattgat gaaacaaaca    240
aatcagaata tattacagaa aatgatataa catgaaaata tattagacca attattttta    300
```

<210> SEQ ID NO 102
<211> LENGTH: 300
<212> TYPE: DNA
<213> ORGANISM: Dirofilaria immitis

<400> SEQUENCE: 102

```
ttgaagtttt cagataaact ttgataaaaa attgttctat gaattctcaa atttcaatta    60
gtgatactta tttcgaaggt aattatgcct gattgaatct tcaatatcaa caaaatgaaa    120
attttagtat gattgttaac tcatacacct ctaattaaag gtattttctt tatcccatga    180
aatgaaaatt tattaagaac ttagaaagct acggtatgcc tttgatgcaa agaaagatt     240 cattttcatt aaatcatgtt taaaaaaaag agcaaagagc aaaaggtgat gaaagttttt    300
```

<210> SEQ ID NO 103
<211> LENGTH: 300
<212> TYPE: DNA
<213> ORGANISM: Dirofilaria immitis

<400> SEQUENCE: 103

```
ttctatacga aatatttgtc tgccataaat ctactcagga actcgataca tcaaaacata    60
agtacgcttg ctctttattt ttcgtttgaa aaataaatag atcattttcg cacttacatt    120
tcaatttcaa ttgctttatt catatctttc tgttttact tactggtatt taacagtcgt     180
tgttcacaat ttaatgatct atgaaacacc atttaattgt atttggacta acttttcgac    240
aagcaaaaga ttaaaattgt cttcagatac agttataaat ttacattgaa gataaatgaa    300
```

<210> SEQ ID NO 104
<211> LENGTH: 300
<212> TYPE: DNA
<213> ORGANISM: Dirofilaria immitis

<400> SEQUENCE: 104

```
taacgatctg tatatcaatg gaataatatt cagttcatgt tgtactcgat atgagataga      60
attacaattt tggaacaaga taatctcaac agctattttc aagaatagtt aaattaggat     120
accattcaaa gaaactttaa aaatgatttt ccatacatta atgcttttg tgttttcgct      180 ctcgaccaga atccaggaat tgtccattat catcaatttg attaactttt atctttattc     240
taattcttca acatttctct aattgatatt agtttcaata ttttaataag taaaaattta     300
```

<210> SEQ ID NO 105
<211> LENGTH: 300
<212> TYPE: DNA
<213> ORGANISM: Dirofilaria immitis

<400> SEQUENCE: 105

```
ataatgtgtt attgatcaaa ggattttag ttacctacca gatggaaaaa aagcaagttt       60
acgaaaacag aagttagcat caactttcat ccatggttac accgtatata atccaatcga     120
ctcatacttt atgttgatct gattttatag cagataacta gttaccttgc tcagcagcag     180
ctaaatcctt tctatttgct taataacaga atattttc attaacaaag aaattatact       240
ccgtgtttga catttcattt taatttcgtt ccaaaaatga aaaaagcttc gtccggaaat     300
```

<210> SEQ ID NO 106
<211> LENGTH: 300
<212> TYPE: DNA
<213> ORGANISM: Dirofilaria immitis

<400> SEQUENCE: 106

```
attattttgt agttttcat ttttagttc aattttcctt tgcttatttt aaatatgcca       60
ttctttattc agactcatag cgaatgcata tgttcattaa tttttttagt tacagttaca     120
aattctcaat ttctctttaa tcatttttt ttccaaaaat agtctgagca ctcaaccatt      180
cattcaacaa ttgcagcttt ttttattgga gccttgtcaa attatcaatt cgtttccatg    240
tttattattg aaataataaa cggtatttag gataacgaag ttcgcttagc ttctttgact     300
```

<210> SEQ ID NO 107
<211> LENGTH: 300
<212> TYPE: DNA
<213> ORGANISM: Dirofilaria immitis

<400> SEQUENCE: 107

```
aaaaattcag gtaatgagat cagtaatttt ttttggtcac tttgctgttt cttatcagct      60
cattgttatc catatcaaat gagcgaaagt gtgtatcaca tattggcaga gtgtaatcta     120
tgaagatttt gcgtatcaaa gtaattatga gagaactgat aattttatt taaagtagta      180 gaaaactcga attaagctaa taaataatcg gttgatatcc atgaaatgaa ttactaatga     240
aatggataat tgagtaataa caaatgatat tcatgaagaa aggcaggttt ttttaatag      300
```

<210> SEQ ID NO 108
<211> LENGTH: 300
<212> TYPE: DNA
<213> ORGANISM: Dirofilaria immitis

<400> SEQUENCE: 108

```
tatacttaaa acaagaaata caattaatgc caatagcaga gtgaaacttc tgaaaaataa    60
tgagttgaaa ctggtaaaat taacatttta ttagaaattt cagaaactta tgactcctca   120
tggcactatc acaaaatgtt tgaaaaaaat tgacagctcg cgtcgattgc aaaaatcatg   180
attcctgata tttagtatcg aacatgtgac aaataatata aagacctaac cataaagcac   240
tgaaacaact cgcggaaaca aaaaattaat ttgcataaac acggaatacg atcagaaaat   300
```

<210> SEQ ID NO 109
<211> LENGTH: 300
<212> TYPE: DNA
<213> ORGANISM: Dirofilaria immitis

<400> SEQUENCE: 109

```
gaattttttt agaaggcttg aagtcgagaa tattagagac tatatcgaag acttaaataa    60
tcctggtaat cttctgtatg aatcaaaatt acctcgaaca gaaccattca gcacatcacg   120
agataattca tggaatgaaa ctagccaatc agagcgttgt aaagaagaa agttatgaaa    180
tgaccttaaa atcaatttaa agcatgtcct cgccatataa gcgttgaaaa gttaggatag   240
aatcaattat caaaaaaata tgttaactag atcttatcaa tcaaacatc agaaggaaaa    300
```

<210> SEQ ID NO 110
<211> LENGTH: 300
<212> TYPE: DNA
<213> ORGANISM: Dirofilaria immitis

<400> SEQUENCE: 110

```
atatgataat agtgaaacaa ttccatcaca ataaatatta tcgattagga gataaattaa    60
cattgatgcc tcaattttgg tcaacaatat atatttgcta ttagcatttt tattaaatcg   120
tttttatctg acttgacata aattgaaata gaaaaattg aatctgttcc ttgttagatt    180
ttcttctaaa aattcttgaa atacaaataa tttcttaaat ttcatatttt ctacataatg   240
tattgcgaca aaaatgctaa tgattggctt attattattt cgaataattt tttaatcaaa   300
```

<210> SEQ ID NO 111
<211> LENGTH: 300
<212> TYPE: DNA
<213> ORGANISM: Dirofilaria immitis

<400> SEQUENCE: 111

```
agctcgaaga tcggacaaaa tttgttcagc ttgttgcctt gaggctttag tctgaaaaga    60
cacttaaaag tataaacaaa ttatattcaa aaaatcttat tttgcatttg cgtcttaatt   120
tttgcttttt gcaaagtttt ttccgagcaa gttttctat cttcgaaaag attatatcaa    180
ttaaaatttc aatttaagca atcattgcct cttcgagttt ctgtttcagc aaataaatat   240
caccaccacg acgctgtcgg aagaaagaaa cgcctttccc aatttctcgt ctcaactttt   300
```

<210> SEQ ID NO 112
<211> LENGTH: 300
<212> TYPE: DNA
<213> ORGANISM: Dirofilaria immitis

<400> SEQUENCE: 112

```
taagaaagct gggagatttt ccaaaaacac tatttcccac gatttgttgt tttctatgat    60
caattcttaa tcaaactctg aaattctcaa attttcgatt tctatccaac ttctacatat   120
ttttttagaa aattcatatt tagcaaagct gagtgtagaa ataattcata cttgcaattc   180
```

```
atttttctta aatttttcgaa tttcttaaaa aagtatttca aattacctac caattttgat    240
tggaaaattc gtggatgcta aaaattcaaa tcaaaatagt aaacagtat tcctaattgt    300
```

<210> SEQ ID NO 113
<211> LENGTH: 300
<212> TYPE: DNA
<213> ORGANISM: Dirofilaria immitis

<400> SEQUENCE: 113

```
aatttaaaaa acacatcgac attttgcggt acggtaatga ttgtttacag taactaaatg     60
tgtcctacgg tagtaatact cgtgtacgta atgaatgagt atagtgaccg gatatttcct    120
tcactagtag gcaatattaa gaagtattt cattttcata ttctatctaa aataaaccga    180
taaaatggtt tttgaattat tacttttca ttgttatttt ttgatcctaa attgtaaaat    240
actgtaataa tttagctaat ttctatgatt ctattcaata tgcttaaatt aaaattctaa    300
```

<210> SEQ ID NO 114
<211> LENGTH: 300
<212> TYPE: DNA
<213> ORGANISM: Dirofilaria immitis
<220> FEATURE:
<221> NAME/KEY: misc_feature
<222> LOCATION: (63)..(72)
<223> OTHER INFORMATION: n is a, c, g, or t

<400> SEQUENCE: 114

```
tcgtatttgt tgtatgtaat atagaaatat tgtttaaatt caatatgtag aaaaaatttc     60
tannnnnnnn nnaattaatt acatattaac tcgtatttgt tgtatgtaat atagaaatat    120
tgtttaaatt caatatgtag aaaaaatttc cataataaag acgaacagca tttataatta    180
tcaatgataa gttgaaatta attcatcaat gataagttga aattaatta tttgaaataa    240 tttctttgaa attcgaatat agacgagaat tttttttttt ttgctaatcg tttatcaaat    300
```

<210> SEQ ID NO 115
<211> LENGTH: 300
<212> TYPE: DNA
<213> ORGANISM: Dirofilaria immitis

<400> SEQUENCE: 115

```
tctagcaata taaattacaa gaatatgccg tccaagtatt tcagaattta ttattaattt     60
ggataataat acattgtaaa tactgcgtat tctggattat tatgcactgc ataataacat    120
gcaatttcgt ctacatatcg cgaataaacg ccaaaagatt tctcgataaa agaaaatata    180
agaattcgta atgaatgtt gtgtcagaga tatgtgttaa ttcataagtc aagatgttgt    240
aaatcgatcc atattagtaa tcatatttac gtgctcgtaa ataaaagcgg tgattcttgt    300
```

<210> SEQ ID NO 116
<211> LENGTH: 300
<212> TYPE: DNA
<213> ORGANISM: Dirofilaria immitis

<400> SEQUENCE: 116

```
atcgaaaaaa gatgatctga tgacggaagg cgaaatgtct gcagaagcta agtgacgga     60 agaaaaaagt gaagaaatga aagaagaagc tggtaaaact cagaaggaat gtaaaactgg    120
agaatcgaaa aaagatgatc tgatgacgga gggcgaaatg tctaaagaag ctaagatgtc    180
ggaagaaaaa agtgaagaaa tgaaagaaga agctgataaa actcagaagg aatgtaaaac    240
```
ggaagaatcg aaaaaagacg atctgacgac agaaggcgaa aaatctgaag tagatgagcc    300

<210> SEQ ID NO 117
<211> LENGTH: 300
<212> TYPE: DNA
<213> ORGANISM: Dirofilaria immitis

<400> SEQUENCE: 117
actaatgata agaaacggag ccgacgattt taggaaatga ataataacga cattgacaac     60
cattgttaga aaattgatag tactgataat aaaagctagt tatagaaaat tgataataat    120
aataaaattg ctggtagcaa atgtctagaa gtgataataa aattaatgat agcaaatgga    180
ttagcaatga taattaaact gatgatagcg aatggattag taatgataat aaaattgatg    240
atagcaaatg actaataatg gtaataaaag ttaatgctag tgataacttg tattttaagt    300

<210> SEQ ID NO 118
<211> LENGTH: 300
<212> TYPE: DNA
<213> ORGANISM: Dirofilaria immitis

<400> SEQUENCE: 118
acagtttata gttacaatat tctccggtga ctaactgtat tttacaactt ataattatag     60
attacaaaat atattatagt agttttataa ttacagtatt cttaagtgaa taactatact    120
ttacagctta cagttacagt agttttctat gttttttgaat attaatttta catggttttt    180
cctagtttca gtttcaaaat tttcagatat tttatgtgtt aaagcaaatt atattcgaga    240
tataaaaagt actggtcata tcttacaatt ctcatccttc tatattggaa agaattgagt    300

<210> SEQ ID NO 119
<211> LENGTH: 300
<212> TYPE: DNA
<213> ORGANISM: Dirofilaria immitis

<400> SEQUENCE: 119
gtattgggac cgcgtatcgg gaaatctgaa agaagtcttt aacagtattt taaatgaata     60
attcaaatcg ttacttctta atatattaat ttatgcgtat atatgcagta catagcattg    120
cttaaattct tattttttccg cggttaaaac cctatgtaag ataagggagg tgattgtatc    180
tgcgccgtac tccttgtttt aatctacctg cttgttgtat atcctccaca tattgtaact    240
gcagcttcac atttgcatat atagtaaggg catcgttgtc tccagaagag atatattatc    300

<210> SEQ ID NO 120
<211> LENGTH: 300
<212> TYPE: DNA
<213> ORGANISM: Dirofilaria immitis

<400> SEQUENCE: 120
gctgcccgaa tgttacaatt aggacgaaag taaaagtagt tgactgtagg tatgacgata     60
aaggaaaaat ttgtatctta agactttaca atttctaaat attacgtgtt ttatcgtgct    120
aacatcacga attccatatt cacaaaaaaa attttgtaga actccatctg gtttggatga    180
atttgctaca gttgaactgg atgatggaac gaaattgcaa acatctctta ttgttagtat    240
tttctaaatt ctgtgaaatt ttgcaacggc attcatgttt aattattaat ttggagaaag    300

<210> SEQ ID NO 121
<211> LENGTH: 300
<212> TYPE: DNA
<213> ORGANISM: Dirofilaria immitis

<400> SEQUENCE: 121

```
aaataagcaa atccgaaagt attacatata cggactaaat attgccattc attcgggagt        60
ataccattgc aaccattggt atttcatttg atcgagaaaa ctagttttg tagtttggga        120
taaagagaaa tggagagagg aactttcatg atcaatttct ttacgtactg aaattcattt       180
ctatggatgt tcttttttcta tttcattctc ctcagcaaat acagtccgaa cagtcatcaa      240
ataagtctaa aaggcatgaa taatataaac atcagcaact ttttaaatga atgcttatta       300
```

<210> SEQ ID NO 122
<211> LENGTH: 300
<212> TYPE: DNA
<213> ORGANISM: Dirofilaria immitis

<400> SEQUENCE: 122

```
atttctataa acatctcttg cattgattaa tttaacatgt tgcaataaat atttcttact        60
tttgaatgta tcattacta gaaaaaactt caatcgagga aataagtttt aaaataaatt        120
catatttgaa ttcatgtcag ttcaaaaatt ctattactat aatacatgtc tcttggttgt       180
atcttttttt cttttgaaat aatacaatca aacggtttcc taaattttca tagacatcat       240
attttaaaaa aaaatgcatt tgaaaatttt cgaaaatcaa tgaacttaat tgatgaaaaa        300
```

<210> SEQ ID NO 123
<211> LENGTH: 300
<212> TYPE: DNA
<213> ORGANISM: Dirofilaria immitis

<400> SEQUENCE: 123

```
gcatgtgtat gtagtatttc tttgtaaaca acatatctaa tctgtctgtc cctttaacat        60
tatagaatag tcagttagtc cgctatttat tttaataaca aaatatctca cttaacttcc       120
atttctttcc taaataattt tgtttcgcta gatctttcct ataatttca aattttcaaa        180
aatgaattaa tcttttattt atatatgtgt atgtatgtgt atgtatgtat gtgtacgttg       240
catatatgta tatgtatgtg tgtatgtgtg tatatgtata tgtatatgtg tgtatgtgtg        300
```

<210> SEQ ID NO 124
<211> LENGTH: 300
<212> TYPE: DNA
<213> ORGANISM: Dirofilaria immitis

<400> SEQUENCE: 124

```
tatgcataat gtgcgaccag ccaataatgt cttcaaacca taattatgca gaaataaatt        60
ttttccagaa ataatttttt ttttttaca tatacttccg atctgtgaga aaatacattt        120
gaagtgaagt gtgaagcaat gctacttttt caaacaacat tgtgaaaatg gattaaaacg       180
caccaatgga gcaagagatc gtaagtttcg ttccgcatgt cctgtggcaa cgtgtaaacc       240
atccgttaac gatatatgat gtaaaagccg acacacccaa attaaaatcc attataaaca       300
```

<210> SEQ ID NO 125
<211> LENGTH: 300
<212> TYPE: DNA
<213> ORGANISM: Dirofilaria immitis

<400> SEQUENCE: 125

```
aaatggatcg tattcacttc gtaagaactt agtgaacgaa aaatcaaacc atcacaataa        60
ctttactttt tttcttttttt tactaaacac actatcctat gaaacaaaaa tgtccaaata       120
```

-continued

```
gattcatatg ataatgaact gtgaagttat ccaatctatc agttctcgaa gagggaataa      180
ataaaaacat taagcaaccc accgatcttc gctgaccatc tccttcttca ttagcaagaa      240
gcaaatcttg tggtgatatt tctgcaacca tctgcaaaat aaagcacgaa aaattaagga      300

<210> SEQ ID NO 126
<211> LENGTH: 300
<212> TYPE: DNA
<213> ORGANISM: Dirofilaria immitis

<400> SEQUENCE: 126
tttgatatgc aatcaactaa ccaaatcaga attcaatgca ttctgataaa tttcttcaat       60
atcgtgcatc aattcgacat catattttga cagtgatgct acctttttag ccgtatttcg      120
gaaaaatatg aattcaacca gctgcgtccc aaaatttaag gctgtagcaa gtccagcaac      180
aaccagccct acaactgaaa attctaaaaa ctggttcacg tgcttatcat taataatttc      240
aacactatca ctatctccac atgaacttga tcgattataa tttagtagaa ctgaaaaaaa      300

<210> SEQ ID NO 127
<211> LENGTH: 300
<212> TYPE: DNA
<213> ORGANISM: Dirofilaria immitis

<400> SEQUENCE: 127
acaaattcgt tttaatattg gattacattg aaattgctga aataaagtgg aaatattgaa       60
aagcatttta caatatttgt taacaacatt atatttaaag aatatacacc ttggtttaaa      120
tggtaaaata atctcaagaa ttttcattag gttaattttt ttttatttat ttatattcac      180
aaaaaattgt aaaagaaaac aaaaacaaca ataataacgg tgacaacaac aacaataata      240
ataacaaaac tatttgttgt gattttgcag cattgatgta gtggggatct tttggagcga      300
```

MARKERS TO PREDICT MACROCYCLIC LACTONE DRUG RESISTANCE IN DIROFILARIA IMMITIS, THE CAUSATIVE AGENT OF HEARTWORM DISEASE

The present application is a national phase entry under 35 U.S.C. § 371 of International Patent Application PCT/US2014/044000, filed on Jun. 25, 2014 and published in English as International Patent. Publication WO2014/210097 A2 on Dec. 31, 2014, which claims benefit of priority to U.S. Pat. App. Ser. No. 61/839,545, filed Jun. 26, 2013; all of which are incorporated by reference in their entirety.

FIELD

Disclosed are genetics related to macrocyclic lactone (ML) endectocide resistance in nematode parasites (e.g., *Dirofilaria immitis*). Single nucleotide polymorphisms within the genome of *D. immitis* are disclosed that, singly or in combination, correlate with reduced responsiveness of the parasites to MLs. Also disclosed are methods for detection of these parasites, methods for treatment of these parasites, and methods and kits for determination of responsiveness of these parasites to MLs.

BACKGROUND

Dirofilariasis is a parasitic disease of animals and occasionally in humans, which may result from infection by a species of *Dirofilaria* such as *D. immitis, D. repens, D. tenuis, D. ursi, D. subdermata, D. lutrae, D. striata* and *D. spectans*.

*Dirofilaria immitis* (heartworm) is a parasitic nematode that commonly infects dogs, foxes, wolves, coyotes, and cats. Heartworms may cause serious vascular damage and may be fatal, especially in highly active animals.

The life cycle of *D. immitis* is well known (reviewed in McCall et al., Adv. Parasitol. 66:193-285, 2008). In brief, a mosquito may become infected when it draws blood from an infected host (e.g. a dog). In the mosquito, microfilariae (mf) develop to the infective larval stage. When the infected mosquito feeds, it may transmit larvae to a new host (e.g. another dog). In the new host, the larvae continue to mature for eight to ten weeks, after which time they move to the right side of the lungs and the pulmonary artery, where they become adult. Adult worms mate and females produce eggs, which develop in utero into the long thin embryos (microfilariae) that are released into the bloodstream. A mosquito that takes in the circulating mf when it draws blood from the infected host starts the cycle again.

*D. immitis* may be found wherever its vector, the mosquito, is found. Generally, *D. immitis* may be found on a world-wide basis, but are very common in areas with mild and warm climates.

Macrocyclic lactones (MLs) are often prescribed as therapeutics or prophylactics in the management of *D. immitis* in veterinary applications. Example MLs include ivermectin (IVM), milbemycin oxime (MO), moxidectin (MOX) and selamectin (SLM). However, resistance to MLs is common in a variety of parasitic nematodes and appears to be developing in *D. immitis*. A number of tests have been described for the detection of anthelmintic resistance in nematodes of livestock and horses, including, faecal egg count reduction test, the egg hatch test, microagar larval development test and molecular tests based on benzimidazole resistance (reviewed in Coles et al., Veterinary Parasitology 136:167-185, 2006). Prichard et al. (European patent EP 0979278) describes a P-glycoprotein sequence in *Haemonchus contortus* which may be useful for the diagnosis of ML resistance in parasitic nematodes. However, there remains a need for methods to detect *D. immitis* (heartworms) that are resistant to a ML.

SUMMARY

Genetic variations (e.g., SNPs) have been discovered in the genomes of *Dirofilaria* spp. nematodes that relate to reduced responsiveness of the nematodes to macrocyclic lactones. In one example, the nematode is *Dirofilaria immitis* (the agent of heartworm in animals). In one example, the macrocyclic lactones are ivermectin, selamectin, milbemycin oxime or moxidectin.

Methods for determining the responsiveness of a *Dirofilaria* spp. nematode to a macrocyclic lactone are disclosed. In one example, the method involves determining the genotype of the nematode at a polymorphic site in a nucleic acid molecule that includes one or more of SEQ ID NOs: 1-127 from the nematode. In one example, the nucleic acid molecule possesses at least 80% sequence identity to one or more of SEQ ID NOs: 1-127. In other examples, the nucleic acid molecule possesses at least 90% or at least 95% sequence identity to one or more of SEQ ID NOs: 1-127. In one example, the nucleic acid molecule includes a a fragment having a length of at least 100 nucleotides of one or more of SEQ ID NOs: 1-127 and includes the polymorphic site. In another example, the nucleic acid molecule includes a fragment having a length of at least 50 nucleotides of one or more of SEQ ID NOs: 1-127 and includes the polymorphic site. In one example, the nucleic acid molecule includes a fragment having a length of at least 100 nucleotides and that possesses at least 95% sequence identity to one or more of SEQ ID NOs: 1-127 and includes the polymorphic site.

In one embodiment of the method, the presence of an alternative nucleotide at the polymorphic site in the nucleic acid molecules indicates that the nematode is likely to be resistant to the macrocyclic lactone. In one embodiment, the method may include isolating the nucleic acid molecule from the nematode, and optionally purifying the nucleic acids prior to determining the genotype of the nematode. In one embodiment of the method, the genotype of the nematode is determined by DNA sequencing, hybridization-based methods including with allele specific oligonucleotides, microarray analysis, enzyme-based methods, single strand conformational polymorphism (SSCP), high resolution melt (HRM) or approaches based on PCR, RT-PCR, or qRT-PCR.

Isolated nucleic acid molecules comprising one or more of SEQ ID NOs: 1-127 are disclosed. In one example, the nucleic acid molecule possesses at least 80% sequence identity to one or more of SEQ ID NOs: 1-127. In other examples, the nucleic acid molecule possesses at least 90% or at least 95% sequence identity to one or more of SEQ ID NOs: 1-127. In one example, the nucleic acid molecule includes a fragment having a length of at least 100 nucleotides of one or more of SEQ ID NOs: 1-127 and includes the polymorphic site. In another example, the nucleic acid molecule includes a fragment having a length of at least 50 nucleotides of one or more of SEQ ID NOs: 1-127 and includes the polymorphic site. In one example, the nucleic acid molecule includes a fragment having a length of at least 100 nucleotides and that possesses at least 95% sequence identity to one or more of SEQ ID NOs: 1-127 and includes the polymorphic site.

Kits for determining the responsiveness of a *Dirofilaria* spp. nematode to a macrocyclic lactone are disclosed. In one example, the kit contains a probe capable of determining the genotype of the nematode at a polymorphic site of one or more of SEQ ID NOs: 1-127. The probe may be an oligonucleotide, a primer or an aptamer. Using the kit, the genotype of the nematode may be determined, for example, by DNA sequencing, hybridization-based methods including using allele specific oligonucleotides, microarray analysis, enzyme-based methods, single strand conformational polymorphism (SSCP), high resolution melt (HRM) or approaches based on PCR, RT-PCR, or qRT-PCR.

Methods for selecting a treatment to treat an animal infected with a *Dirofilaria* spp. nematode are disclosed. In one example, the method involves determining the genotype of the nematode at a polymorphic site in a nucleic acid molecule that includes one or more of SEQ ID NOs: 1-127 and selecting the treatment based on the genotype of the nematode. In one example, the nucleic acid molecule possesses at least 80% sequence identity to one or more of SEQ ID NOs: 1-127. In other examples, the nucleic acid molecule possesses at least 90% or at least 95% sequence identity to one or more of SEQ ID NOs: 1-127. In one example, the nucleic acid molecule includes a fragment having a length of at least 100 nucleotides of one or more of SEQ ID NOs: 1-127 and includes the polymorphic site. In another example, the nucleic acid molecule includes a fragment having a length of at least 50 nucleotides of one or more of SEQ ID NOs: 1-127 and includes the polymorphic site. In one example, the nucleic acid molecule includes a fragment having a length of at least 100 nucleotides and that possesses at least 95% sequence identity to one or more of SEQ ID NOs: 1-127 and includes the polymorphic site.

In one embodiment, the method involves treating the animal with one or more alternative agents when an alternative nucleotide is found at the polymorphic site. Alternative agents may include one or more of an arsenic-based therapy, diethylcarbamazine, and antibiotics. In one embodiment, the method may include isolating the nucleic acid molecule from the nematode, and optionally purifying the nucleic acids prior to determining the genotype of the nematode. In one embodiment of the method, the genotype of the nematode is determined by DNA sequencing, hybridization-based methods including with allele specific oligonucleotides, microarray analysis, enzyme-based methods, single strand conformational polymorphism (SSCP), high resolution melt (HRM) or approaches based on PCR, RT-PCR, or qRT-PCR.

BRIEF DESCRIPTION OF THE DRAWINGS

FIG. 1 illustrates the genotype frequencies for the SNP within Marker 617 (SEQ ID NO: 1), Marker 714 (SEQ ID NO: 2), Marker 814 (SEQ ID NO: 3), and Marker 887 (SEQ ID NO: 4).

FIG. 2 illustrates the genotype frequencies for the SNP within Marker 1514 (SEQ ID NO: 5), Marker 2557 (SEQ ID NO: 6), Marker 3367 (SEQ ID NO: 7), and Marker 3488 (SEQ ID NO: 8).

FIG. 3 illustrates the genotype frequencies for the SNP within Marker 4553 (SEQ ID NO: 9), Marker 5266 (SEQ ID NO: 10), Marker 5365 (SEQ ID NO: 11) and Marker 5667 (SEQ ID NO: 12).

FIG. 4 illustrates the genotype frequencies for the SNP within Marker 6568 A (SEQ ID NO: 13), Marker 6568 B (SEQ ID NO: 14), Marker 7633 (SEQ ID NO: 15), and Marker 9400 (SEQ ID NO: 16).

FIG. 5 illustrates the genotype frequencies for the SNP within Marker 9473 (SEQ ID NO: 17), Marker 9858 (SEQ ID NO: 18), Marker 10349 (SEQ ID NO: 19), and Marker 10520 (SEQ ID NO: 20).

FIG. 6 illustrates the genotype frequencies for the SNP within Marker 10678 (SEQ ID NO: 21), Marker 11676 (SEQ ID NO: 22), Marker 11933 A (SEQ ID NO: 23), and Marker 11933 B (SEQ ID NO: 24).

FIG. 7 illustrates the genotype frequencies for the SNP within Marker 12716 (SEQ ID NO: 25), Marker 12925 (SEQ ID NO: 26), Marker 13063 (SEQ ID NO: 27), and Marker 15000 A (SEQ ID NO: 28).

FIG. 8 illustrates the genotype frequencies for the SNP within Marker 15000 B (SEQ ID NO: 29), Marker 15709 A (SEQ ID NO: 30), Marker 15709 B (SEQ ID NO: 31), Marker 17333 (SEQ ID NO: 32).

FIG. 9 illustrates the genotype frequencies for the SNP within Marker 18110 (SEQ ID NO: 33), Marker 19999 (SEQ ID NO: 34), Marker 20570 (SEQ ID NO: 35), and Marker 20587 (SEQ ID NO: 36).

FIG. 10 illustrates the genotype frequencies for the SNP within Marker 20698 (SEQ ID NO: 37), Marker 21554 (SEQ ID NO: 38), Marker 22174 (SEQ ID NO: 39), and Marker 22254 (SEQ ID NO: 40).

FIG. 11 illustrates the genotype frequencies for the SNP within Marker 22259 (SEQ ID NO: 41), Marker 24708 (SEQ ID NO: 42), Marker 25276 A (SEQ ID NO: 43), and Marker 25443 (SEQ ID NO: 44).

FIG. 12 illustrates the genotype frequencies for the SNP within Marker 26447 (SEQ ID NO: 45), Marker 26730 (SEQ ID NO: 46), Marker 26974 (SEQ ID NO: 47), and Marker 27080 A (SEQ ID NO: 48).

FIG. 13 illustrates the genotype frequencies for the SNP within Marker 27349 (SEQ ID NO: 49), Marker 27461 (SEQ ID NO: 50), Marker 29128 (SEQ ID NO: 51), and Marker 29168 (SEQ ID NO: 52).

FIG. 14 illustrates the genotype frequencies for the SNP within Marker 29455 (SEQ ID NO: 53), Marker 29816 (SEQ ID NO: 54), Marker 30575 (SEQ ID NO: 55), and Marker 30991 (SEQ ID NO: 56).

FIG. 15 illustrates the genotype frequencies for the SNP within Marker 31796 (SEQ ID NO: 57), Marker 32164 (SEQ ID NO: 58), Marker 32223 (SEQ ID NO: 59), and Marker 34439 (SEQ ID NO: 60).

FIG. 16 illustrates the genotype frequencies for the SNP within Marker 34903 (SEQ ID NO: 61), Marker 35336 (SEQ ID NO: 62), Marker 36040 (SEQ ID NO: 63), and Marker 37881 (SEQ ID NO: 64).

FIG. 17 illustrates the genotype frequencies for the SNP within Marker 38662 A (SEQ ID NO: 65), Marker 38662 B (SEQ ID NO: 66), Marker 38622 C (SEQ ID NO: 67), and Marker 38622 D (SEQ ID NO: 68).

FIG. 18 illustrates the genotype frequencies for the SNP within Marker 39492 (SEQ ID NO: 69), Marker 42291 (SEQ ID NO: 70), Marker 42411 (SEQ ID NO: 71), and Marker 45689 (SEQ ID NO: 72).

FIG. 19 illustrates the genotype frequencies for the SNP within Marker 45719 (SEQ ID NO: 73), Marker 46063

(SEQ ID NO: 74), Marker 47481 (SEQ ID NO: 75), and Marker 47722 A (SEQ ID NO: 76).

Figure 20:
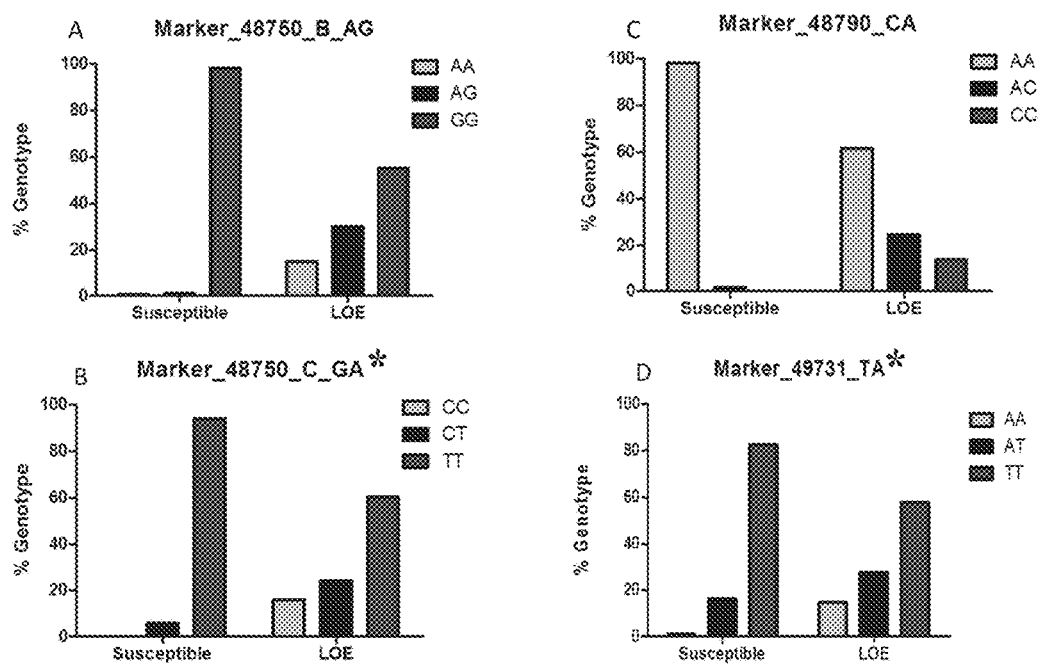

FIG. 20 illustrates the genotype frequencies for the SNP within Marker 48750B (SEQ ID NO: 77), Marker 48750 C (SEQ ID NO: 78), Marker 48790 (SEQ ID NO: 79), and Marker 49731 (SEQ ID NO: 80).

Figure 21:
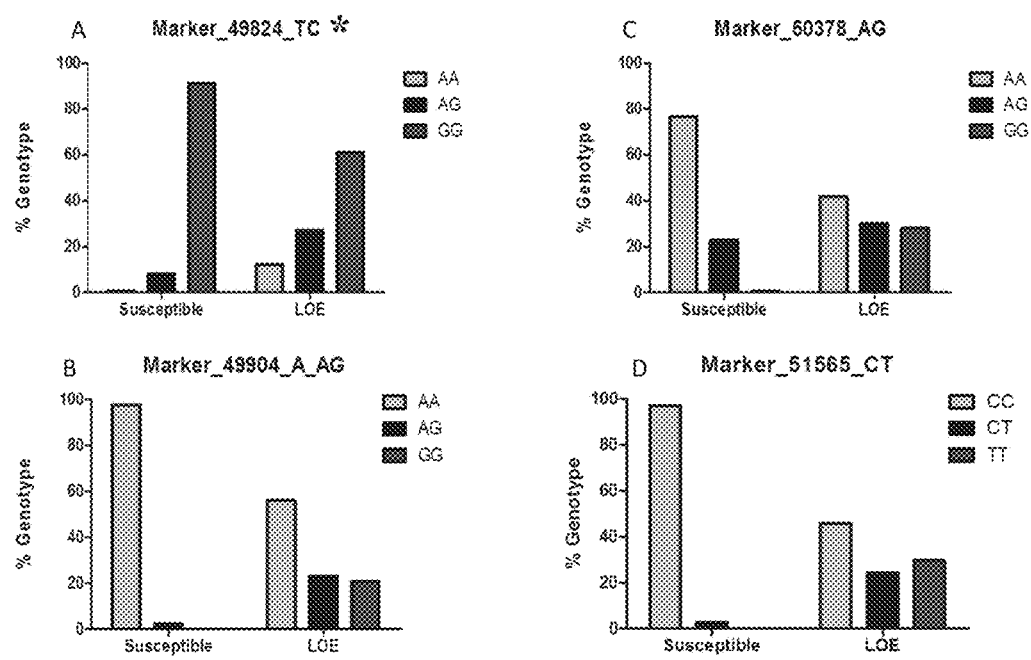

FIG. 21 illustrates the genotype frequencies for the SNP within Marker 49824 (SEQ ID NO: 81), Marker 49904 A (SEQ ID NO: 82), Marker 50378 (SEQ ID NO: 83), and Marker 51565 (SEQ ID NO: 84).

Figure 22:
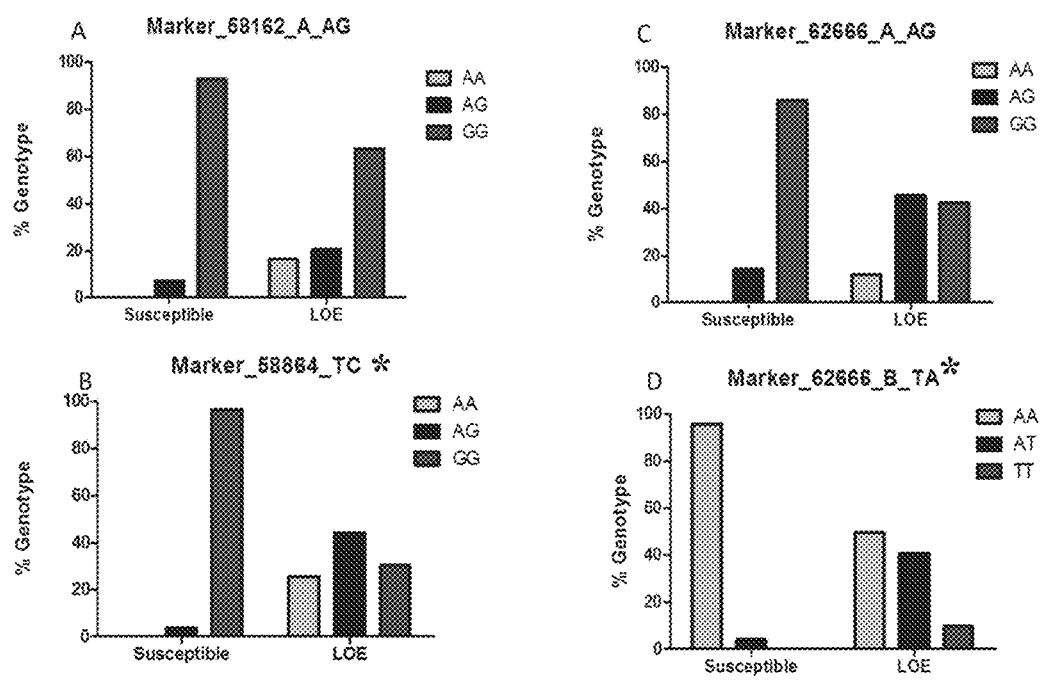

FIG. 22 illustrates the genotype frequencies for the SNP within Marker 58162 A (SEQ ID NO: 85), Marker 58864 (SEQ ID NO: 86), Marker 62666 A (SEQ ID NO: 87), and Marker 62666 B (SEQ ID NO: 88).

Figure 23:
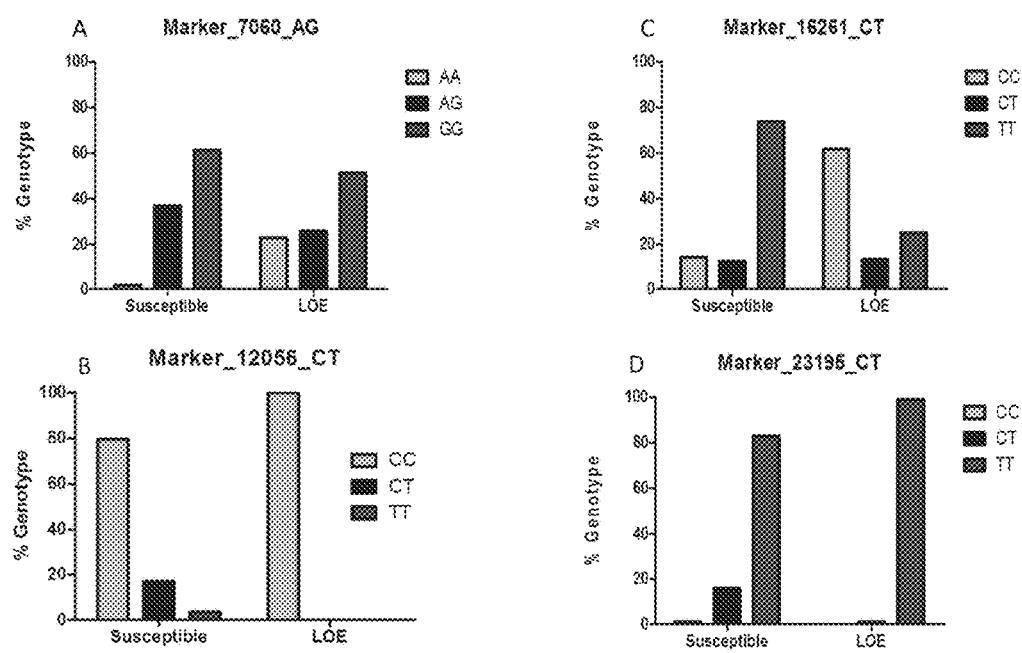

FIG. 23 illustrates the genotype frequencies for the SNP within Marker 7060 (SEQ ID NO: 89), Marker 12056 (SEQ ID NO: 90), Marker 16261 (SEQ ID NO: 91), and Marker 23195 (SEQ ID NO: 92).

Figure 24:
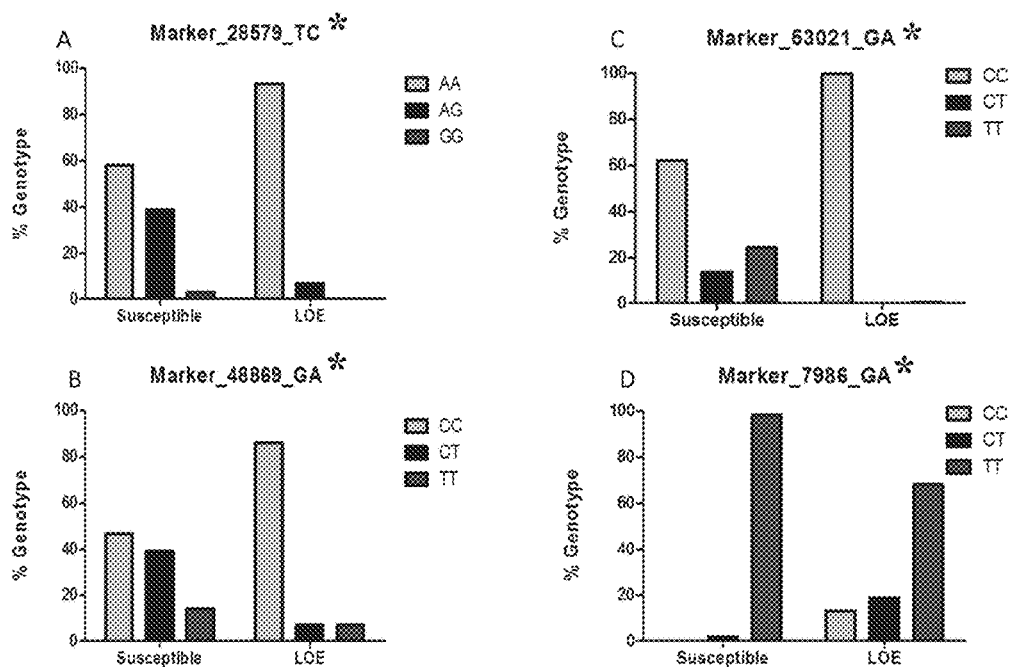

FIG. 24 illustrates the genotype frequencies for the SNP within Marker 28579 (SEQ ID NO: 93), Marker 48869 (SEQ ID NO: 94), Marker 53021 (SEQ ID NO: 95), and Marker 7986 (SEQ ID NO: 96).

Figure 25:
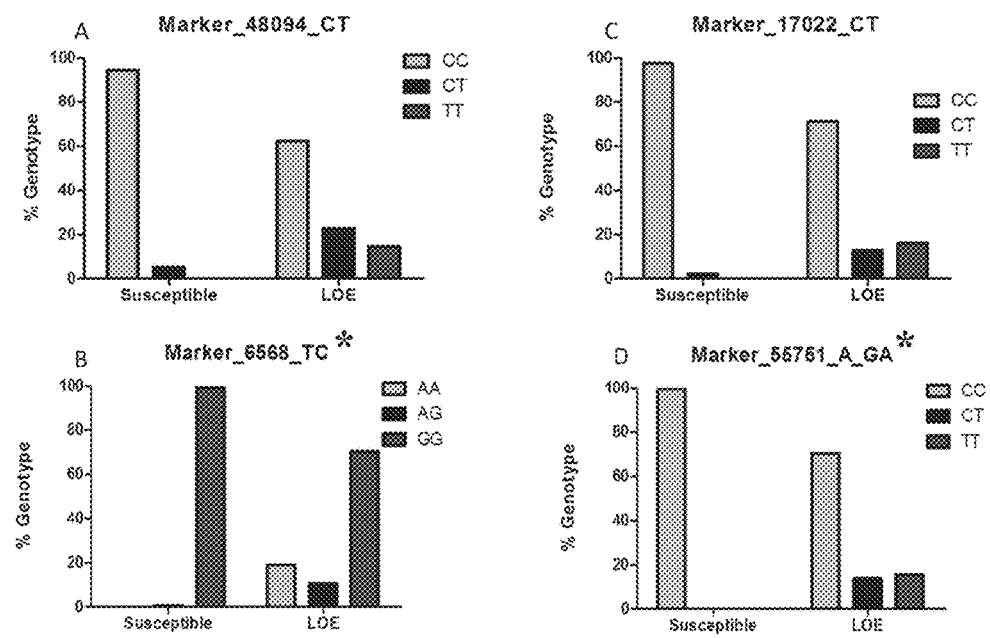

FIG. 25 illustrates the genotype frequencies for the SNP within Marker 48094 (SEQ ID NO: 97), Marker 6568 (SEQ ID NO: 98), Marker 17022 (SEQ ID NO: 99), and Marker 55751 A (SEQ ID NO: 100).

Figure 26:
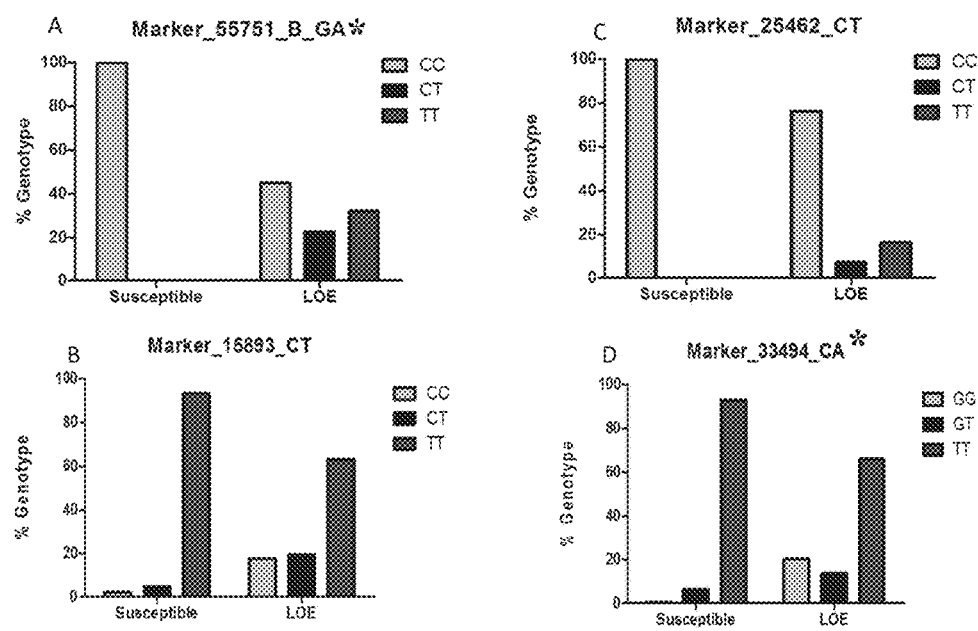

FIG. 26 illustrates the genotype frequencies for the SNP within Marker 55751B (SEQ ID NO: 101), Marker 15893 (SEQ ID NO: 102), Marker 25462 (SEQ ID NO: 103), and Marker 33494 (SEQ ID NO: 104).

Figure 27:
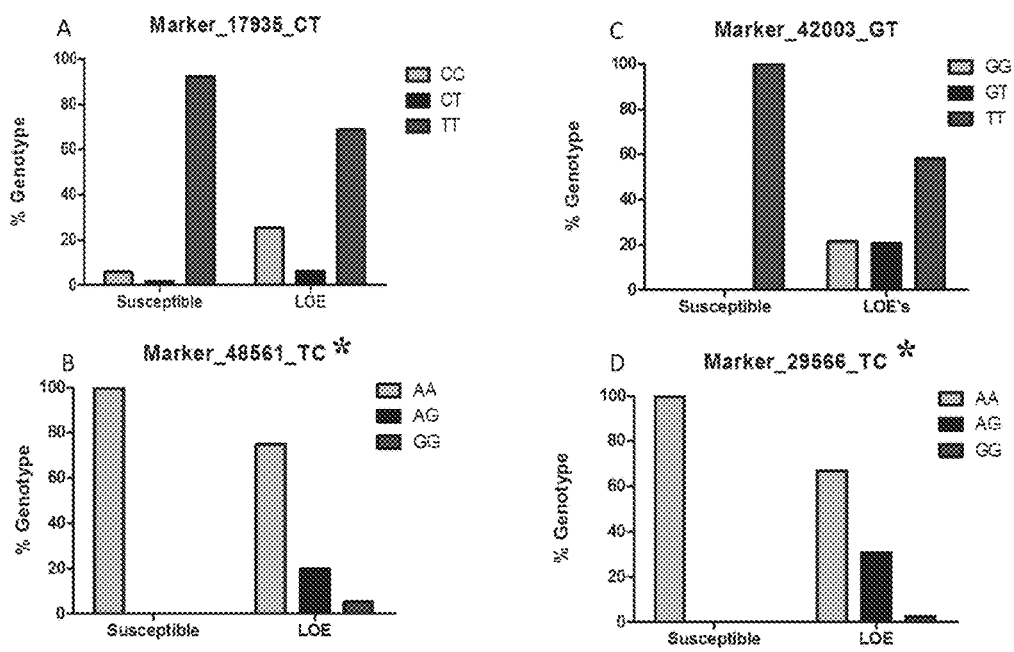

FIG. 27 illustrates the genotype frequencies for the SNP within Marker 17935 (SEQ ID NO: 105), Marker 48561 (SEQ ID NO: 106), Marker 42003 (SEQ ID NO: 107), and Marker 29566 (SEQ ID NO: 108).

Figure 28:
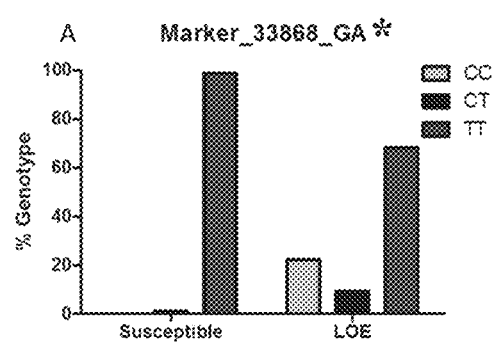

FIG. 28 illustrates the genotype frequencies for the SNP within Marker 33868 (SEQ ID NO: 109).

FIG. 29 presents Table 1 which displays genotype frequencies for markers representing SEQ ID NOs: 110-127.

DETAILED DESCRIPTION

Definitions

Herein, "macrocyclic lactones" or "MLs" means products, or chemical derivatives thereof, of soil microorganisms that belong to the genus *Streptomyces* including, but not necessarily limited to, avermectins and milbemycins. These molecules are used to treat species of endo- and ectoparasites in a wide range of hosts. Avermectins in use include, without limitation, ivermectin, abamectin, doramectin, eprinomectin and selamectin. Available milbemycins include, without limitation, milbemycin oxime and moxidectin. Macrocyclic lactones have a potent, broad antiparasitic spectrum at low dose levels. They are active against many immature nematodes (including hypobiotic larvae) and arthropods. A single therapeutic dose may persist in concentrations sufficient to be effective against incumbent nematode infections for prolonged periods after treatment.

Macrocyclic lactone (ML) heartworm preventatives were developed for the treatment of dogs and cats, which were not already infected, to prevent establishment of adult infections by targeting the developing L3/L4 stages. Macrocyclic lactones also have effects on the microfilarial stage (L1). Macrocyclic lactone endectocides such as ivermectin (IVM), milbemycin oxime (MO), moxidectin (MOX) and selamectin (SLM) are used during the transmission season for chemoprophylaxis for heartworm in dogs and cats.

Herein, "responsiveness" means that a nematode responds following exposure to a macrocyclic lactone (ML). In embodiments of the invention, a nematode may respond by being sensitive or resistant to a ML. Sensitivity or sensitive to a ML means that the macrocyclic lactone adversely affects the exposed *D. immitis* nematode. For example, a ML may be lethal or sub-lethal to the *D. immitis* nematode, shorten its life-span or inhibit its ability to reproduce. Resistance is the reduction in effectiveness of a drug, herein MLs, in curing a disease or improving symptoms (e.g., eradicating heartworm organisms from a dog). A *D. immitis* nematode may be ML resistant if the drug meant to neutralize it is ineffective, less effective or has reduced effectiveness. A *D. immitis* nematode may also be ML resistant if the drug, at a specific dose that is meant to neutralize it, has reduced effect. In embodiments of the invention, responsiveness of a nematode to a macrocyclic lactone may be determined in vivo or in vitro.

Herein, "loss of efficacy" or "LOE" means that there is at least a perceived decrease in responsiveness of nematodes to MLs. The perceived decrease in responsiveness may be perceived or may be actual. In one example, the decrease in responsiveness of nematodes to MLs may be real, in which case the nematodes may be said to be resistant to MLs. In another example, the decrease in responsiveness of nematodes to MLs may be perceived and not real. For example, in the case where a dog infected with heartworm is treated with MLs, for the purpose of eliminating heartworm from the dog, the dog owner may not be compliant in properly administering the MLs to the dog. In such a case, the heartworm infection may not be eliminated from the dog because sufficient doses of MLs were not administered, for example. The dog owner, or other observer, may mistakenly believe that MLs were compliantly administered to the dog (e.g., the owner believes s/he administered MLs as directed but, in reality, missed administrations, administered inadequate dosages, etc.) and, because the heartworms were not eliminated from the dog, the heartworm parasites are resistant to MLs. In at least some of these cases, heartworms are not eliminated from the dog because of the lack of compliance. In these cases, continued presence of heartworm may not be due to ML resistance of the heartworm organisms (i.e., the decrease in responsiveness of the heartworm parasites is perceived and not real). In cases of LOE, generally there is no confirmation that the heartworm infection is actually resistant to MLs.

Herein, "resistant" or "confirmed resistant" generally means that the heartworm organisms were shown to have at least reduced responsiveness to MLs. In one example, dogs infected with heartworm are treated with MLs, using a regime known to normally rid dogs of heartworm infection (i.e., compliance of the ML treatment is not in question), but the treatment does not rid the dog of heartworm organisms. Such heartworm organisms, which would normally be eliminated from the dogs by the compliant treatment, are not eliminated because of their reduced responsiveness to ML. Such heartworm organisms are said to be resistant to the MLs.

In one example, a *D. immitis* nematode may be said to be resistant to a ML if less than about 93%, less than about 91%, less than about 89%, less than about 87%, less than about 85%, less than about 83%, less than about 81%, less than about 79%, less than about 77%, less than about 75%, less than about 73%, less than about 71%, less than about 69%, less than about 67%, less than about 65%, less than about, 63%, less than about 61%, less than about 59%, less than about 57%, less than about 55%, less than about 53%, less than about 51%, less than about 49%, less than about 47%, less than about 45%, less than about 43%, less than about 41%, less than about 39%, less than about 37%, less than about 35%, less than about 33%, less than about 31%, less than about 29%, less than about 27%, less than about 25%, less than about 23%, less than about 21%, less than about 19%, less than about 17%, less than about 15%, less than about 13%, less than about 11%, less than about 9%, less than about 7%, less than about 5%, less than about 3%, less than about 1% or if 0% of nematodes died following exposure to a $LD_{95}$ (a lethal dose or concentration of a drug that should have killed 95% of D. immitis nematodes) dose or concentration of a macrocyclic lactone.

In another embodiment, a D. immitis nematode may be said to be sensitive to a macrocyclic lactone if at most about 5%, at most about 4%, at most about 3%, at most about 2%, at most about 1% or if 0% of nematodes survived following exposure to a $LD_{95}$ (a lethal dose or concentration of a drug that should have killed 95% of D. immitis nematodes) dose or concentration of a macrocyclic lactone.

Herein, "nucleic acid", "nucleotide sequence" or "nucleic acid molecule" may refer to a polymer of DNA and/or RNA which may be single or double stranded and optionally containing synthetic, non-natural or altered nucleotide bases capable of incorporation into DNA or RNA polymers. "Nucleic acids", "nucleic acid sequences" or "nucleic acid molecules" may encompass genes, cDNA, DNA (e.g. genomic DNA) and RNA encoded by a gene. Nucleic acids or nucleic acid sequences may comprise at least 3, at least 10, at least 100, at least 1000, at least 5000, or at least 10000 nucleotides or base pairs.

"Nucleic acids", "nucleic acid sequences" or "nucleic acid molecules" may be modified by any chemical and/or biological means known in the art including, but not limited to, reaction with any known chemicals such as alkylating agents, browning sugars, etc.; conjugation to a linking group (e.g. PEG); methylation; oxidation; ionizing radiation; or the action of chemical carcinogens. Such nucleic acid modifications may occur during synthesis or processing or following treatment with chemical reagents known in the art.

Herein, an "isolated nucleic acid molecule" may refer to a nucleic acid molecule that does not occur in nature as part of a larger polynucleotide sequence; and/or may be substantially free from any other nucleic acid molecules or other contaminants that are found in its natural environment. As used herein, an "isolated nucleic acid molecule" may also encompass recombinantly or synthetically produced nucleic acid molecules.

Herein, the term "identity" or "identical" refers to sequence similarity between two or more polynucleotide molecules, at one position in within molecules, or at more than one position within the molecules. Identity can be determined by comparing each position in the aligned sequences. A degree of identity between nucleic acid sequences is a function of the number of identical or matching nucleic acids at positions shared by the sequences, for example, over a specified region. Optimal alignment of sequences for comparisons of identity may be conducted using a variety of algorithms, as are known in the art. In one example, sequence identity may be determined using the well-known and publicly available BLAST algorithm (e.g. BLASTn and BLASTp). In another embodiment, the person skilled in the art can readily and properly align any given sequence and deduce sequence identity/homology by mere visual inspection.

Herein, "single nucleotide polymorphisms" or "SNPs" refer to genetic variations (or non-identity) at specific locations in a genome (i.e., polymorphic site). Generally, at a specific position in a genome, the identity of a nucleotide may be invariant or constant. At some positions in a genome, however, the identity of a nucleotide may not be invariant. At such positions, there may be a nucleotide present at the position at a relative higher frequency than other nucleotides, when the genomes of different individuals within a population are analyzed. The nucleotide most commonly found at such a position may be referred to as the wild-type nucleotide at this position. However, there may be one or more other nucleotides found at this position at relatively lower frequencies. These nucleotides may be referred to as alternative nucleotides. The frequencies by which the alternative nucleotides are found may vary. In one example, the SNPs described herein may play a role in responsiveness of nematodes to MLs. In one example, the SNPs may identify or tag a region of a genome that may play a role in responsiveness of nematodes to MLs (i.e., the SNP itself is not directly involved in the altered responsiveness to MLs but may be genetically linked to genetic changes that are involved in altered responsiveness). In one example, presence of one or more of the disclosed SNPs may indicate that the parasite whose genome contains the one or more SNPs is less responsive to MLs compared to parasites that do not have the SNPs.

As used herein, the term "polymorphic site" may refer to a region/specific location in a nucleic acid at which two or more alternative nucleotide sequences are observed in a significant number of nucleic acid samples from a population of individuals. A polymorphic site that is one nucleotide in length may be referred to herein as a "single nucleotide polymorphism" or a "SNP."

Herein, "marker" or "markers" generally refer to nucleic acid sequences that can contain one or more SNPs. These nucleic acid sequences can be of different lengths.

Herein, "genotype" refers to the genetic constitution of a cell, an organism, or an individual (i.e. the specific allele makeup of the individual) usually with reference to a specific character under consideration. In the context of this application, genotype generally refers to identity of nucleotides at positions of SNPs. In one example, a GG genotype may mean that at a specific position of a gene (e.g., a polymorphic site) which has two alleles, the nucleotide at the same location in each allele is G (guanine). Alleles are alternative DNA sequences at the same physical locus, which may or may not directly result in different phenotypic traits, but generally within the context of this application, correlate with decreased responsiveness of parasites to MLs. In any particular diploid organism, with two copies of each chromosome, the genotype for each gene comprises the pair of alleles present at that locus, which are the same in homozygotes and different in heterozygotes.

Suitable approaches for use in determining genotype are known in the art and may include, without limitation, PCR, RT PCR, qRT PCR, SSCP and hybridization with allele specific oligonucleotides. Other approaches may include nucleic acid hybridization to DNA microarrays or beads, restriction fragment length polymorphism (RFLP), terminal restriction fragment length polymorphism (t-RFLP), amplified fragment length polymorphism (AFLP), and multiplex ligation-dependent probe amplification (MLPA).

Herein, "consists essentially of" or "consisting essentially of" means that the nucleic acid sequence may include one or more nucleotide bases, including within the sequence or at one or both ends of the sequence, but that the additional nucleotide bases do not materially affect the function of the nucleic acid sequence.

Genomes and SNPs

Figure 1:
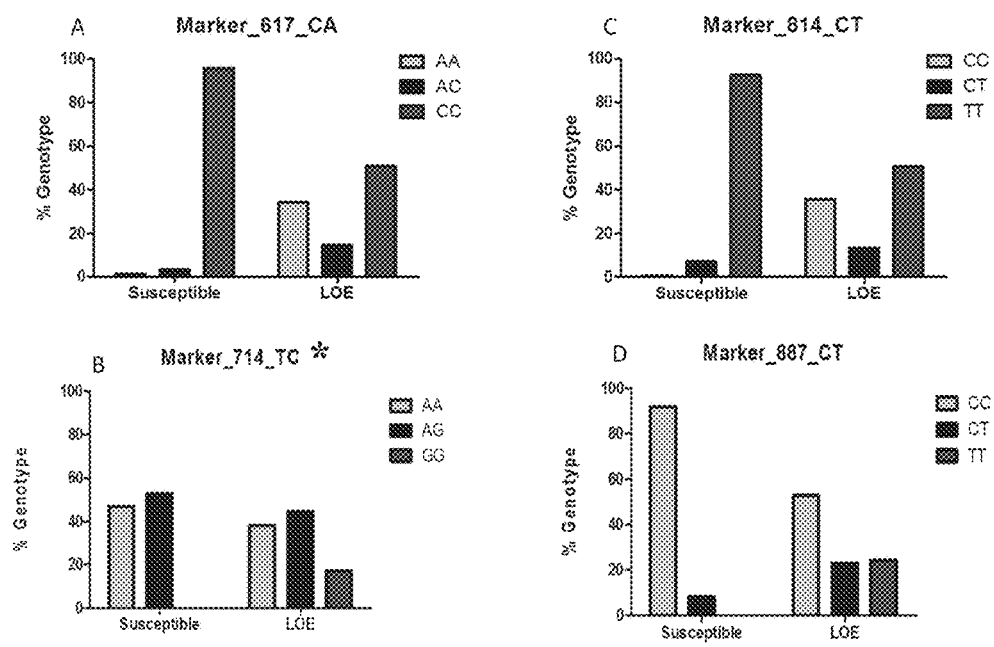
FIGS. 1-28 illustrate the genotype frequencies for the SNP within each of the indicated markers, for susceptible and LOE isolates. The graphs are representative of markers that are also designated as SEQ ID NOs: 1-109 within the application. For markers designated with an asterisk (*), the genotype indicated shows analysis of the reverse complement of the sequences shown as SEQ ID NOs: 1-109 within the application.
Figure 2:
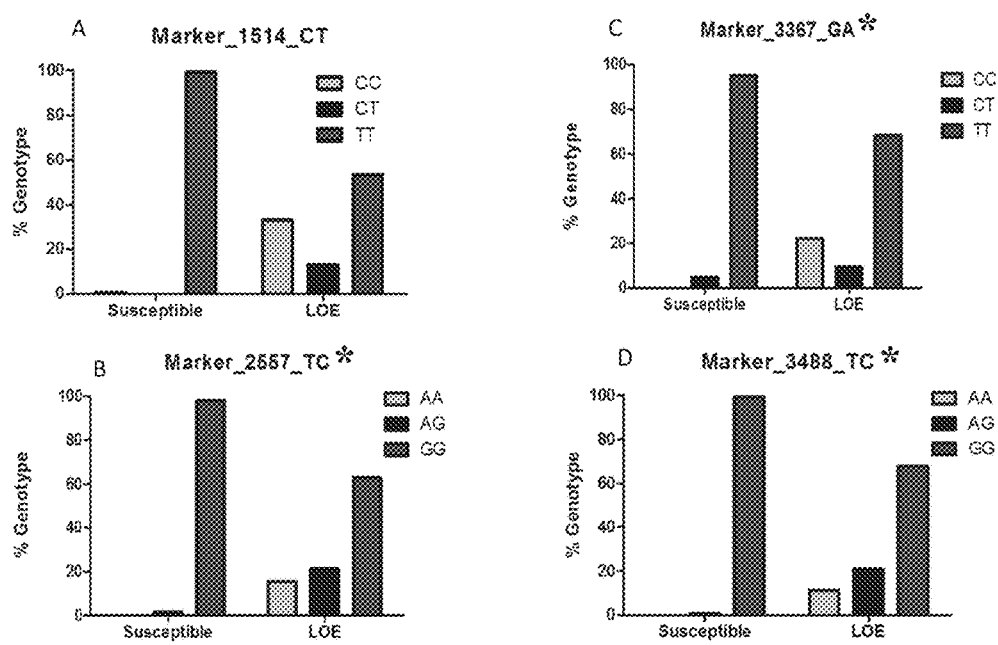
Figure 3:
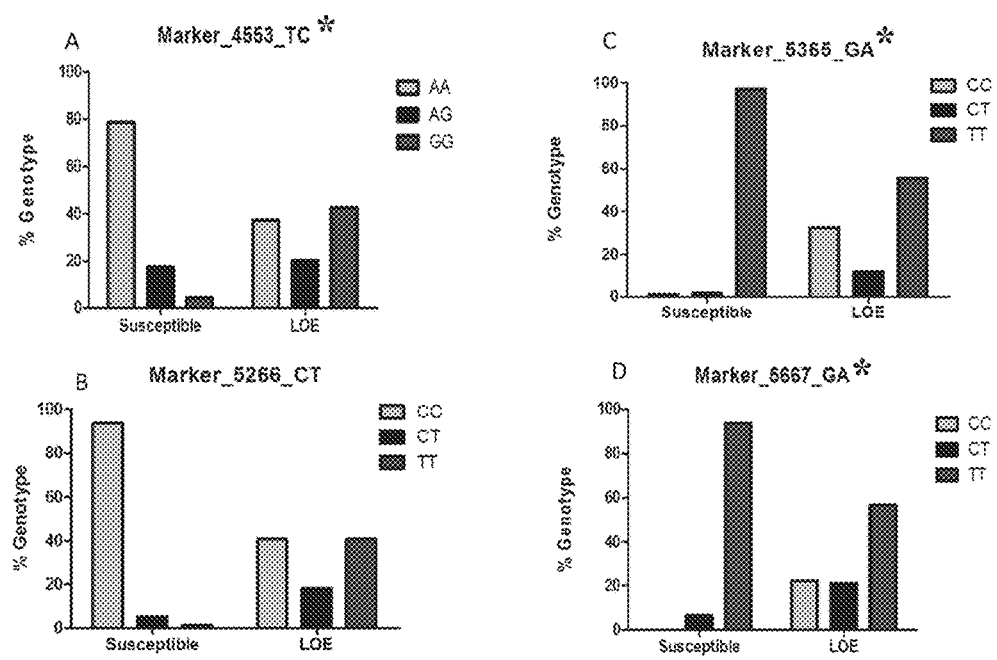
Figure 4:
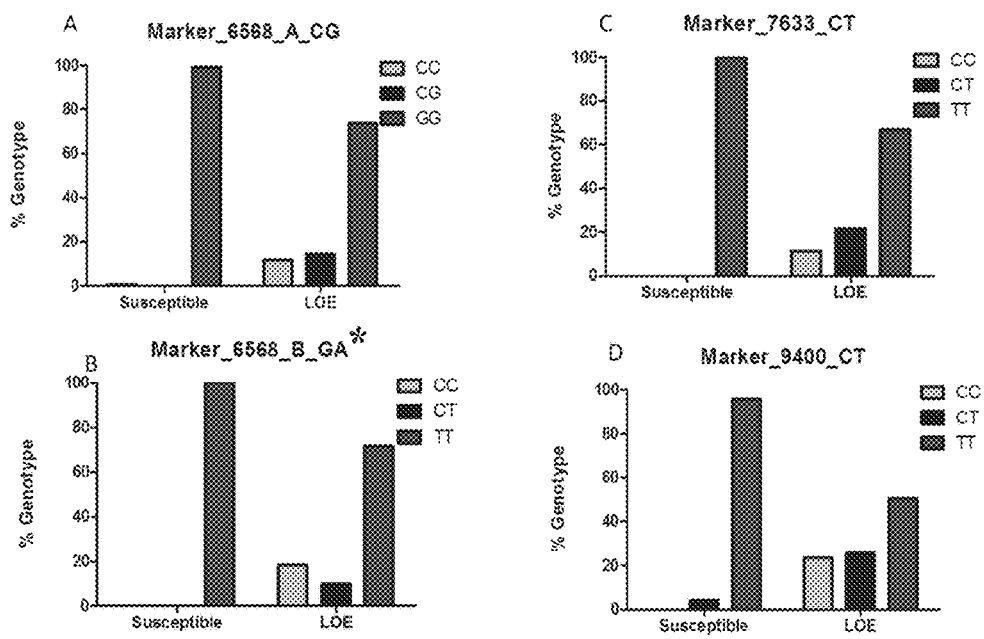
Figure 5:
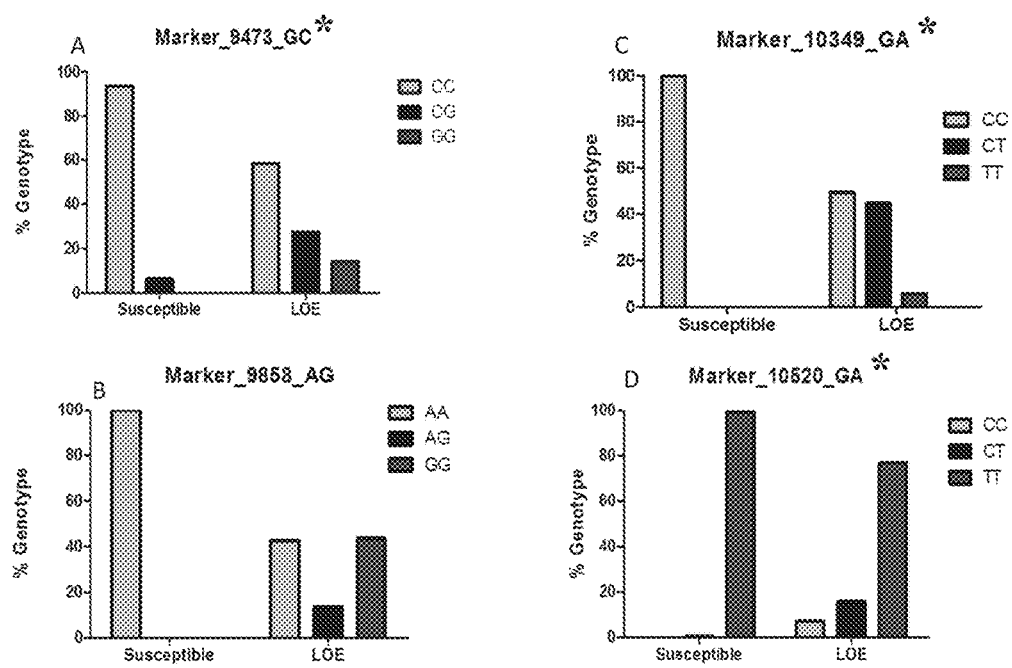
Figure 6:
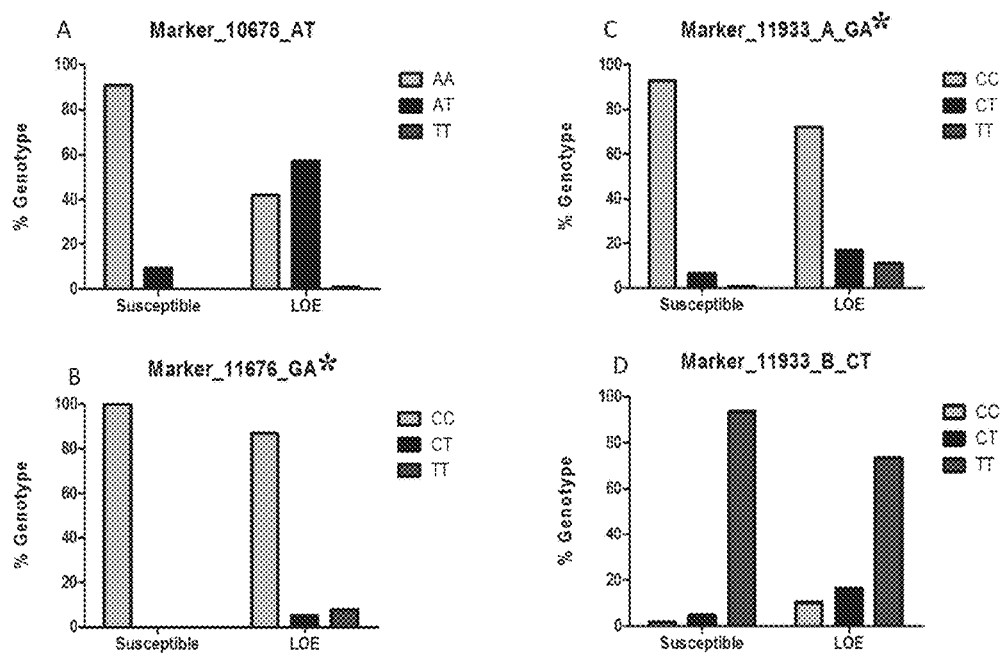
Figure 7:
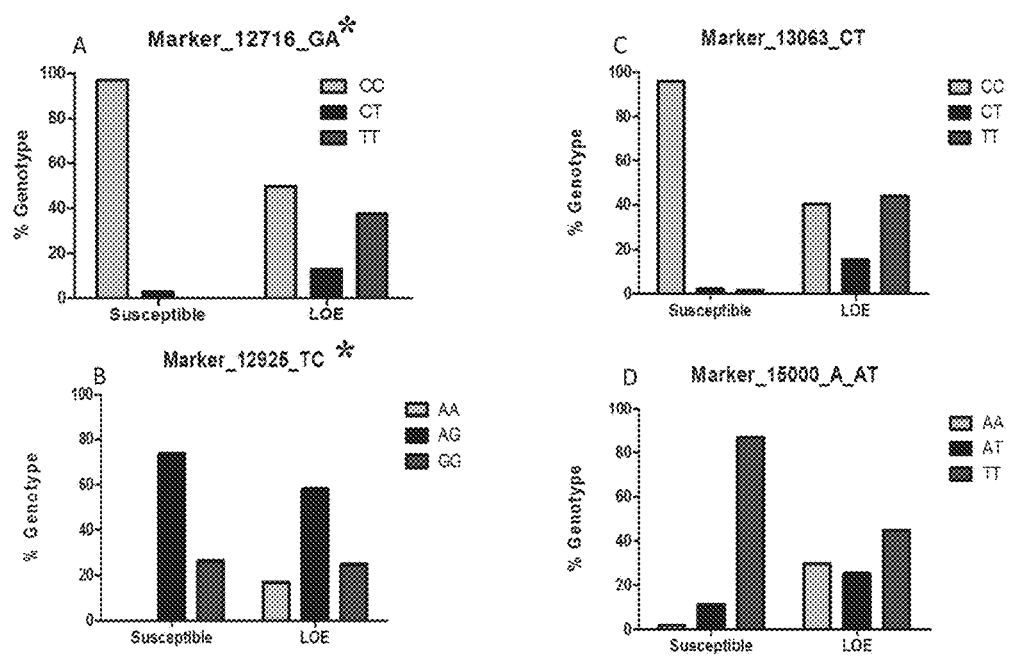
Figure 8:
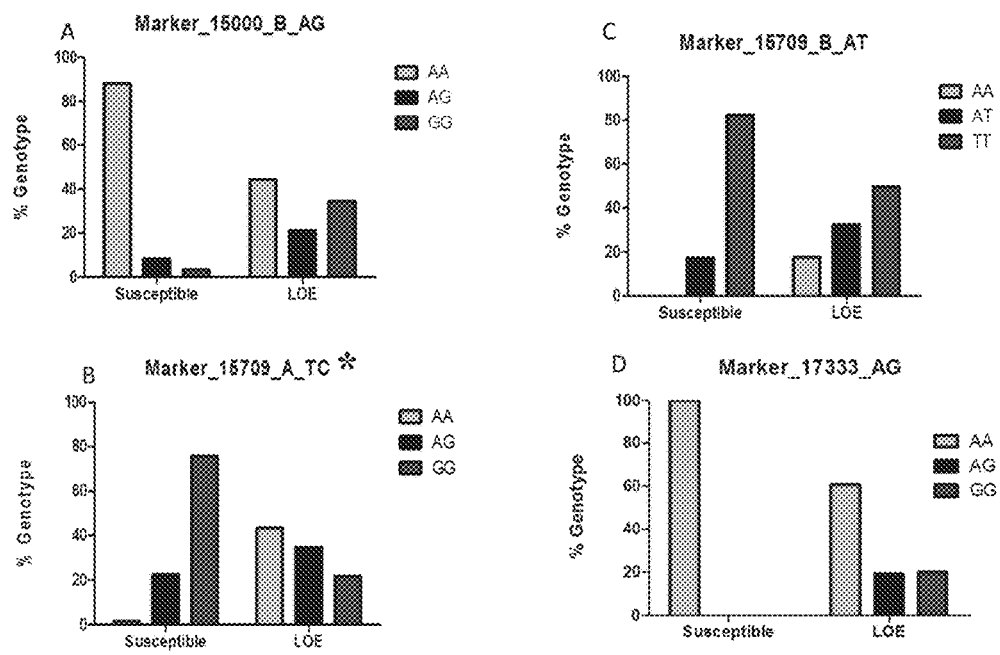
Figure 9:
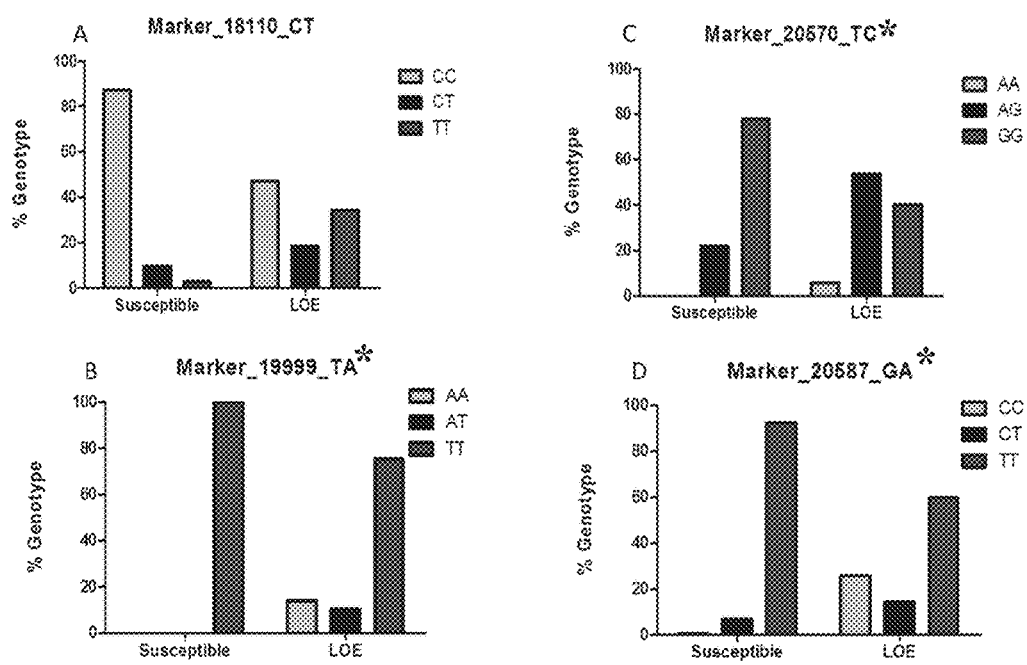
Figure 10:
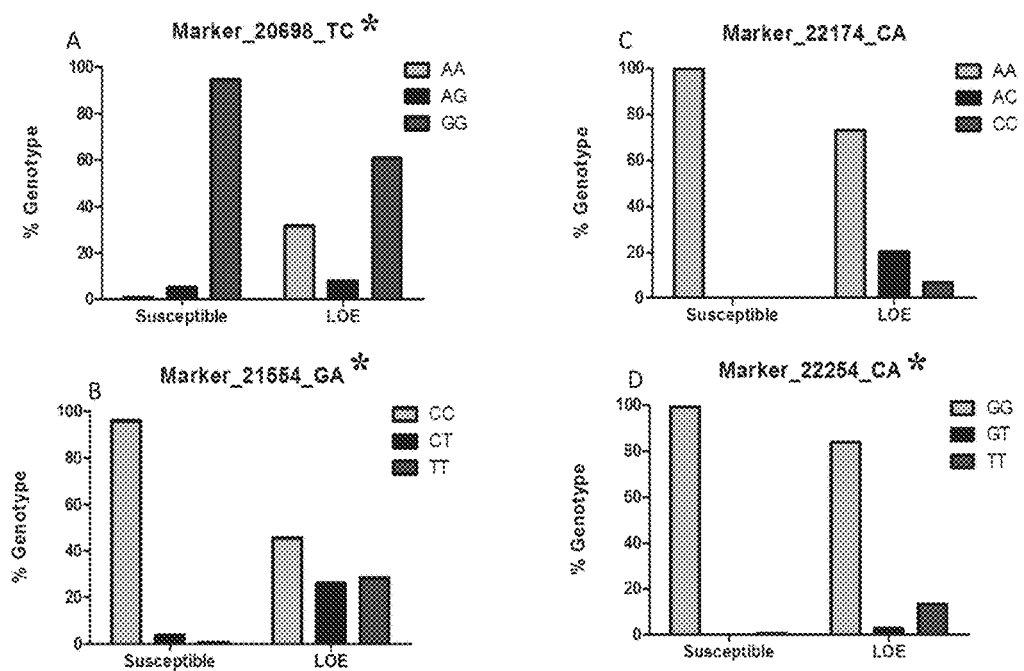
Figure 11:
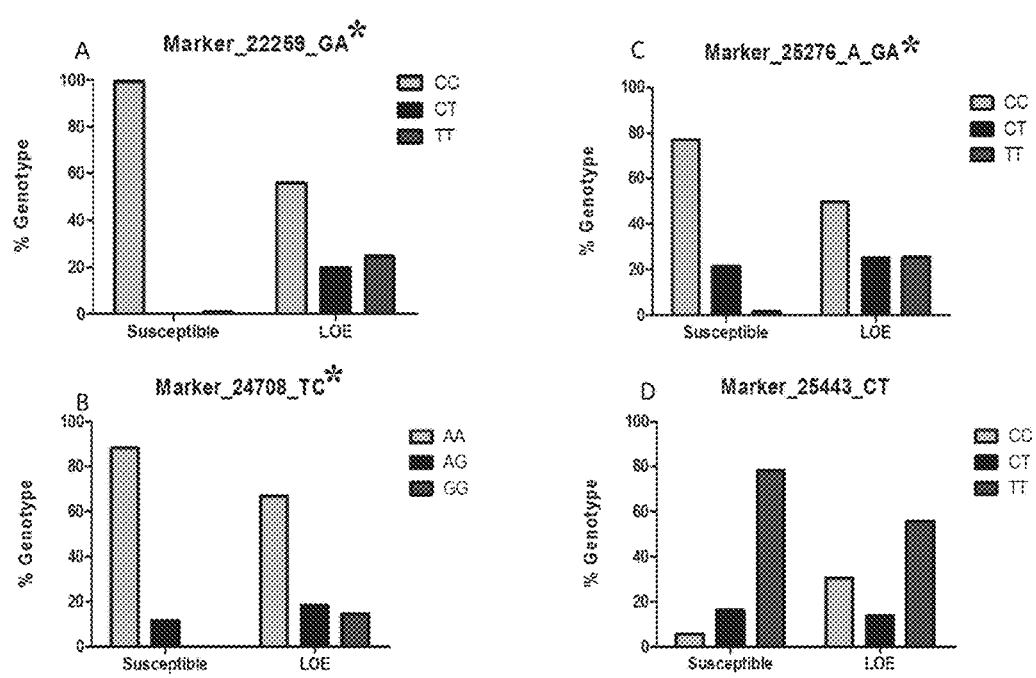
Figure 12:
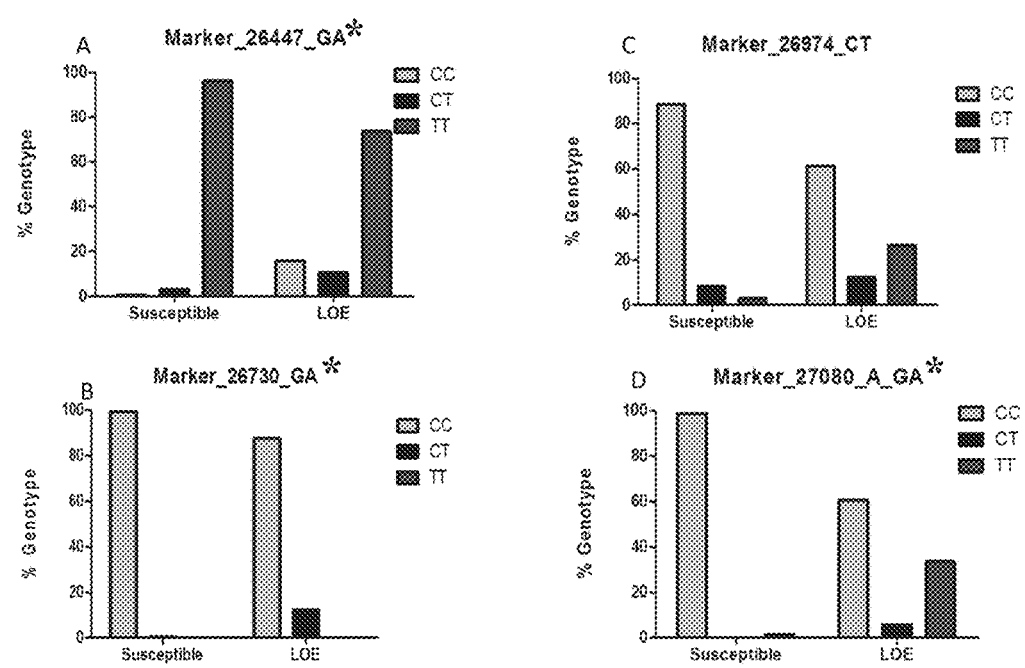
Figure 13:
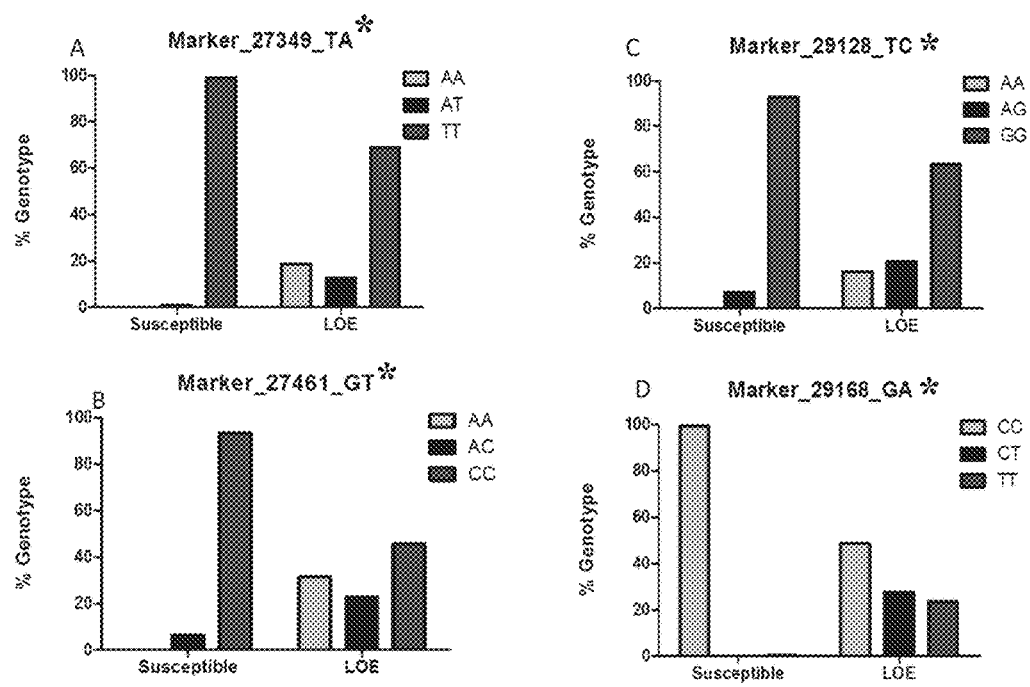
Figure 14:
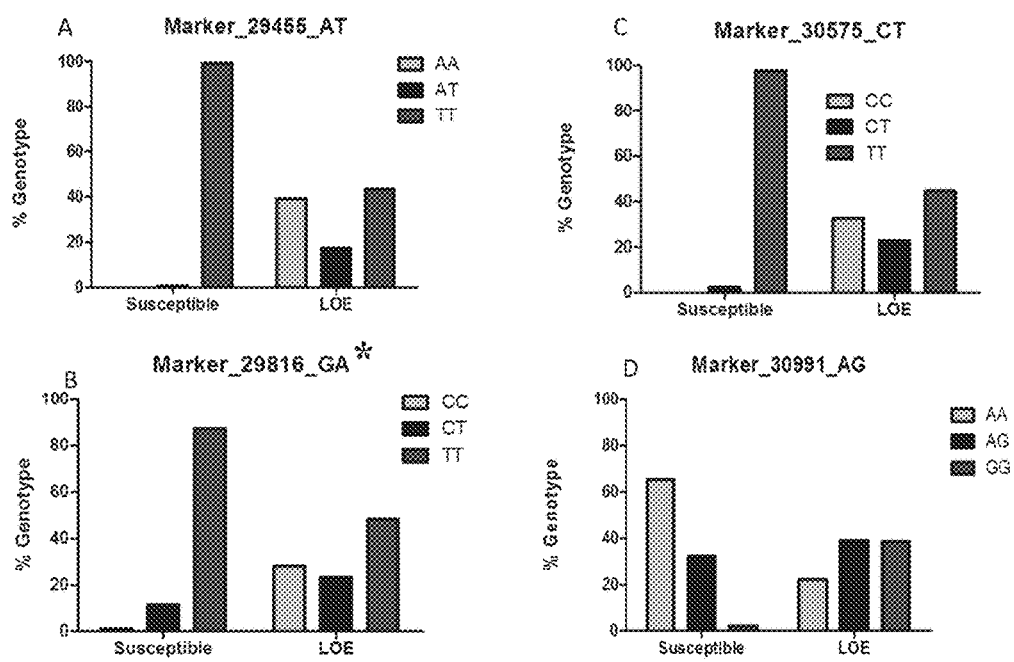
Figure 15:
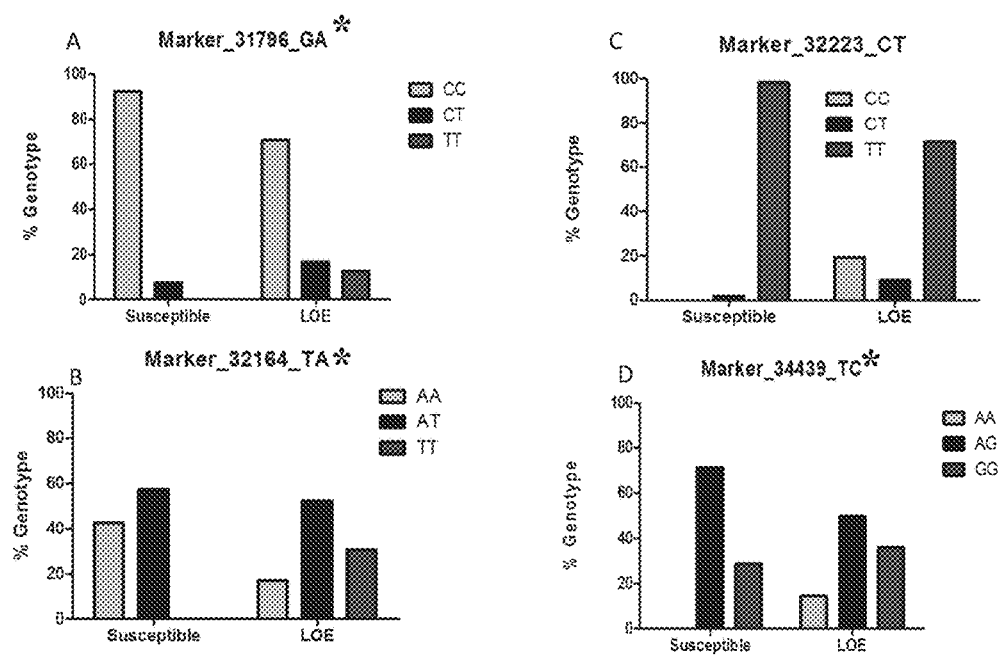
Figure 16:
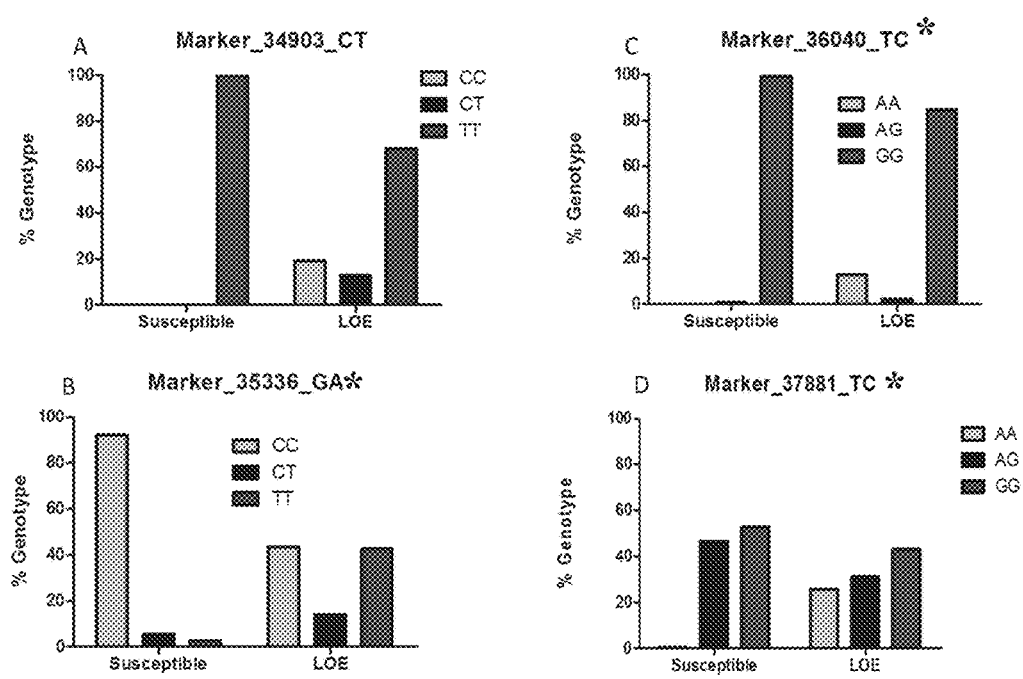
Figure 17:
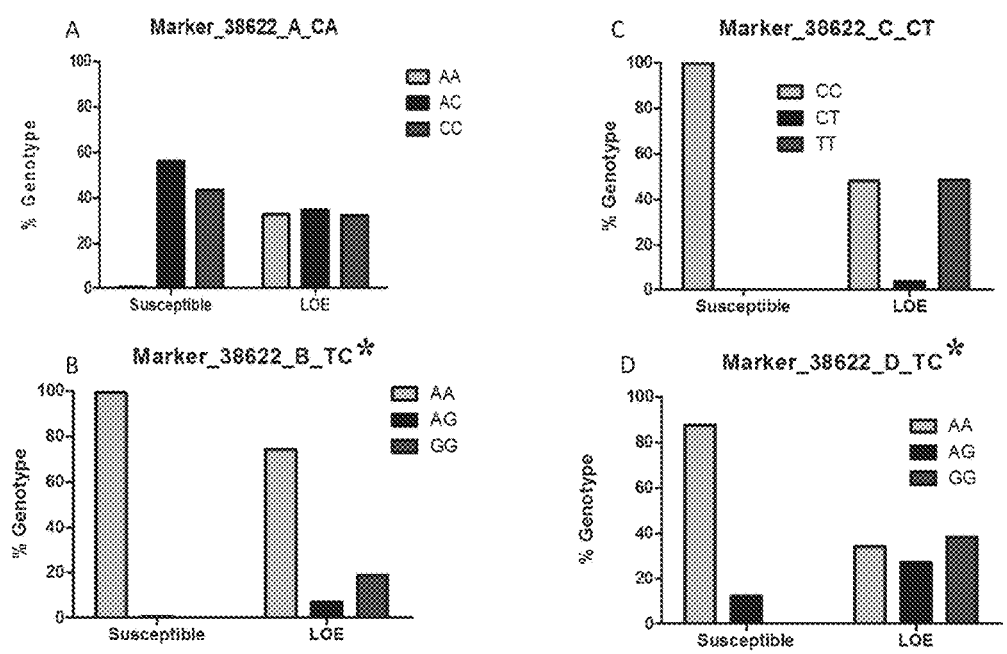
Figure 18:
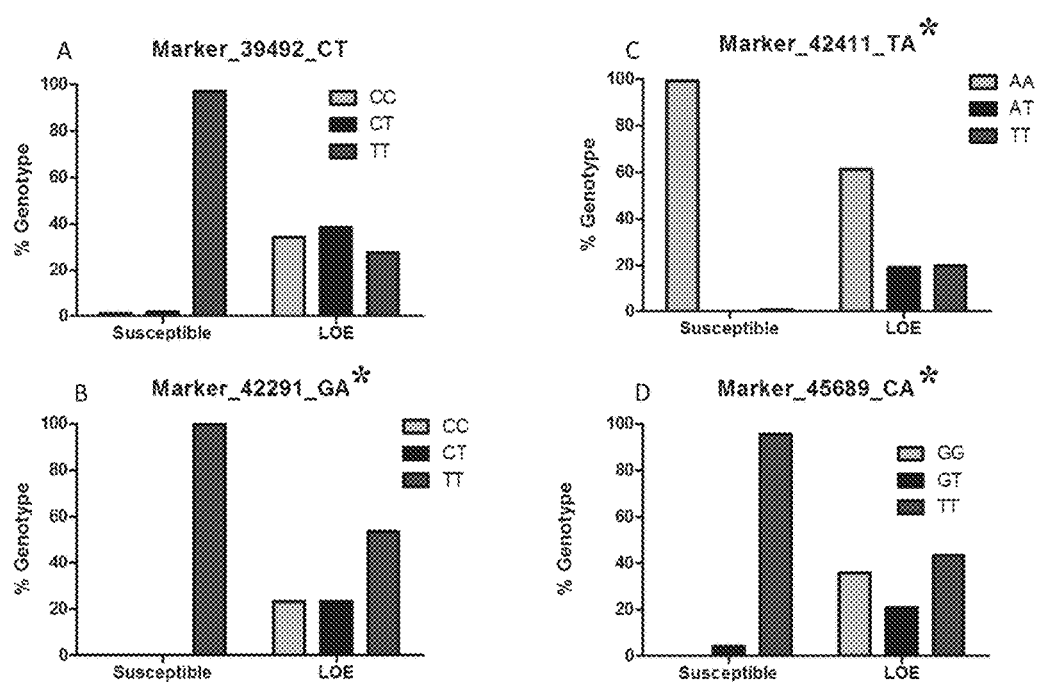
Figure 19:
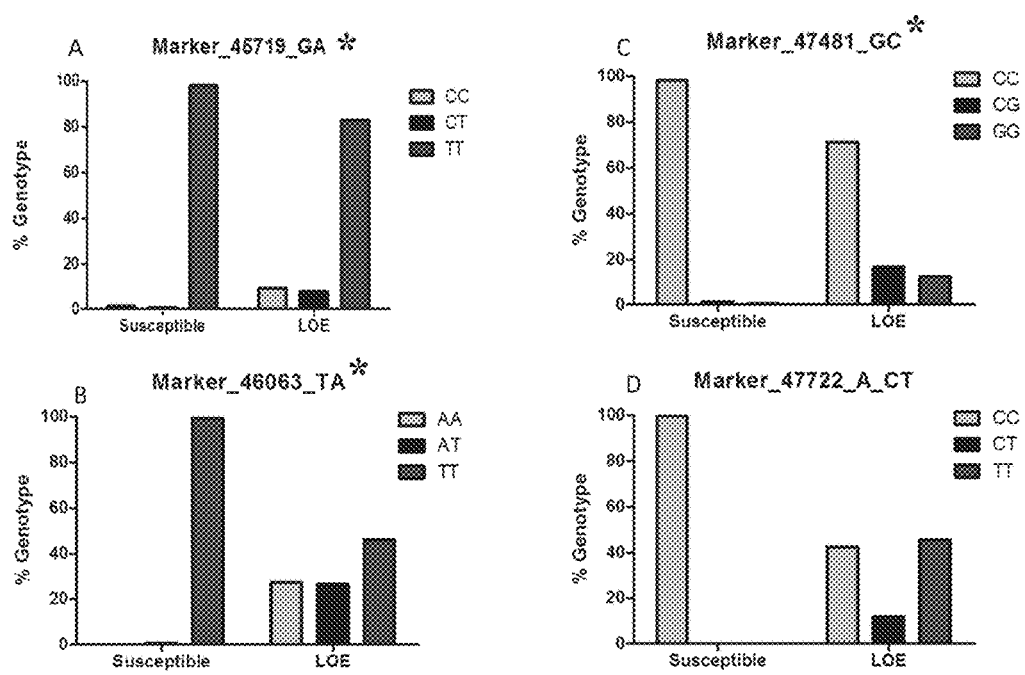

In one aspect, the invention relates to isolated nucleic acid molecules possessing at least 80% sequence identity to SEQ ID NOs: 1-127, over their entire length, and comprising the alternative nucleotides at the location of the SNP (i.e., polymorphic site), the alternative nucleotides indicated by the underlined nucleotide in SEQ ID NOs: 1-127, as disclosed in this application. The alternative nucleotides generally have a lower frequency of occurrence at the indicated positions within the sequences, as shown in FIG. 1 and in Table 1. In one embodiment of the invention, the genome of a nematode parasite, or a population of parasites, may contain one or more of the alternative nucleotides at the polymorphic sites shown in SEQ ID NOs: 1-127. The presence of these alternative nucleotides generally correlates with reduced sensitivity of the parasites to MLs as compared to parasites that do not contain the alternative nucleotides.

In another aspect, the invention relates to isolated nucleic acid molecules comprising, consisting of, or consisting essentially of the sequence depicted in SEQ ID NOs: 1-127.

A nucleic acid molecule of the invention may comprise a sequence corresponding to that of SEQ ID NOs: 1-127 over their length, and containing the alternative nucleotide at the SNP site (i.e., polymorphic site). In embodiments of the invention, the nucleic acid sequence may be at least about 80%, at least about 81%, at least about 82%, at least about 83%, at least about 84%, at least about 85%, at least about 86%, at least about 87%, at least about 88%, at least about 89%, at least about 90%, at least about 91%, at least about 91%, at least about 92%, at least about 93%, at least about 94%, at least about 95%, at least about 96%, at least about 97%, at least about 98%, at least about 99% or 100% identical to SEQ ID NOs: 1-127, but that was isolated from a nematode having the alternative nucleotide at the position in each sequence shown by the underlined nucleotide as disclosed in this application.

In other embodiments, the nucleic acid molecule of the invention may comprise a part of, or fragment of, SEQ ID NOs: 1-127 that also contains the polymorphic site and the alternative nucleotide at the polymorphic site. In various examples, the fragment of SEQ ID NOs: 1-127 may be 5, 20, 15, 20, 25, 30, 35, 40, 45, 50, 60, 70, 80, 90, 100, 120, 140, 160, 180, 200, 220, 240, 260, 280, 300 or more nucleotides in length.

A nucleic acid molecule of the invention may be derived from a *D. immitis* nematode containing one or more of SEQ ID NOs: 1-127 as disclosed in this application. As used herein, "derived from" may refer to a nucleic acid molecule that was isolated from a natural source, e.g. a *Dirofilaria immitis* nematode. It may also refer to a nucleic acid molecule that is man-made, e.g. recombinantly or synthesized on the basis of a nucleic acid molecule isolated from a *D. immitis* nematode.

Detection of SNPs

SNPs may be detected by any method that can determine the identity of a nucleotide at a specific position in a genome (e.g., polymorphic site) and that allows for comparison of the identities of nucleotides at the specific genome position between individuals or populations of individuals. Differences in the identities of nucleotides at a specific position may be indicative of a SNP.

A variety of methods may be used to detect SNPs. In one example, hybridization-based methods can be used. Hybridization-based methods generally rely on hybridizing complementary DNA probes to the site containing the SNP. In one method, dynamic allele-specific hybridization (DASH) relies on differences in melting temperatures resulting from mismatched base pairing. By designing probes that differentially hybridize based on nucleotide changes in target genomes, SNPs can be detected.

In one example of a hybridization-based method, molecular beacons can be used. Molecular beacons are single-stranded nucleotide probes, with a fluorochrome at one end and a fluorochrome quenching molecule at the other end, that can form a stem-loop structure and place the fluorochrome and quenching molecule in close proximity to one another. In absence of hybridization of a molecular beacon to a genome region, the fluorochrome will be quenched, due to its close proximity to the quenching molecule. When the molecular beacon hybridizes to a genome region, the fluorochrome generally will not form a stem-loop structure. Under these conditions, the fluorochrome will fluoresce, due to the increased distance to the fluorochrome from the quenching molecule.

In one example of a hybridization-based method, oligonucleotide microarrays, which are high-density arrays containing hundreds of thousands of probes, are used for hybridization to SNPs. By comparing differential hybridization to redundant probes, it is possible to detect SNPs.

In one example of detecting SNPs, enzyme-based methods may be used. In one example of an enzyme-based method for detecting SNPs, restriction endonucleases are used to digest a genomic DNA. By determining the fragment lengths that result from the digest, it can be determined whether certain sites within a genome fail to be cleaved by the endonuclease due to a nucleotide change (e.g., alternative nucleotide) in the sequence recognized by the endonuclease.

In one example of an enzyme-based method for detecting SNPs, PCR (polymerase chain reaction)-based methods are used. In one example of this, two primer pairs are designed such that only one of them will function to amplify a site containing a SNP, depending on whether the SNP is present. The sizes of the amplified products are distinguishable, therefore informing which primer pair functions, and whether the SNP is present.

In one example of an enzyme-based method for detecting SNPs, nucleotide probes are designed to hybridize to a genomic site and produce a mismatch, whether or not a SNP is present at the specific genomic site. An endonuclease (e.g., Flap endonuclease) that cleaves one of the probes, depending on whether a mismatch exists, is used. Using fluorochromes and quenching molecules, attached to one or more of the probes, SNPs can be detected.

In one example of an enzyme-based method for detecting SNPs, primer extension is used. In this method, primers are hybridized to genome DNA immediately upstream of the SNP. DNA polymerase is then used to extend the primer in a mini-sequencing reaction. The sequencing reaction determines the presence of a SNP.

In one example of an enzyme-based method for detecting SNPs, the 5'-nuclease activity of Taq DNA polymerase is used. A TaqMan assay is performed concurrently with a PCR reaction. The method is set up so the PCR reaction will extend through a site containing a SNP, and release a fluorochrome from a probe hybridizing to the SNP region, depending on whether the probe contains a mismatch due to presence of the SNP.

In one example of an enzyme-based method for detecting SNPs, DNA ligase is used to ligate two probes, one hybridizing to a SNP site in a genome, depending on whether the SNP is present, and a second probe hybridizing adjacent to the SNP site. If both probes hybridize to the genome without mismatches, ligase will connect the two probes, which can be measured.

Other methods of detecting SNPs exist, including for example, detection of single-stranded conformation polymorphisms, temperature gradient gel electrophoresis to detect duplex mismatches due to SNPs, denaturing high performance liquid chromatography to detect mismatched duplexes, high resolution melting analysis, use of mismatch-binding proteins, and others.

In one example of detecting SNPs, a biological sample comprising a *D. immitis* nematode may be obtained from a subject. The subject may be, without limitation, a dog, fox, wolf, coyote or cat. In the context of the invention, a biological sample may be any sample (e.g. bodily fluid, excrement, organ, tissue, etc) from a subject. The biological sample may be from a subject that is known to have, or is suspected of having, a *D. immitis* nematode infection. The *D. immitis* nematode may be isolated from the biological sample with standard separation methods and techniques.

A nucleic acid sample may be isolated or obtained from a *D. immitis* nematode prior to use. Methods of isolating nucleic acids from organisms and tissues are known. Such methods may include, but are not limited to, traditional DNA extraction, with proteinase K digestion followed by phenol chloroform extraction, sodium hydroxide extraction, and physical disruption, followed by purification, e.g. by cesium chloride centrifugation or high performance liquid chromatography (HPLC); or the use of commercial kits. A skilled person would appreciate that different approaches may be used to isolate a nucleic acid sample from an adult *D. immitis* nematode in comparison to a microfilaria. In an embodiment of the invention, the nucleic acid sample comprises genomic DNA.

The nucleic acid sequences of the nucleic acids from the parasite may be determined using any one of numerous methods known in the art. In some techniques, sequences of separate pieces of the genome are assembled into linear whole genome representations of the parasite using computer-based methods. In one example, massive parallel sequencing may be used. Massive parallel sequencing (also called "next-generation sequencing") may encompass various high-throughput DNA sequencing methods. One such method is the HiSeq2000 system from ILLUMINA®.

Through comparison of sequences from separate parasites or parasite populations (e.g., comparison of a consensus or reference genome obtained from parasites sensitive to MLs with a consensus or reference genome obtained from parasites resistant to MLs), presumptive SNPs can be identified.

The presumptive SNPs can be analyzed further. In one example, high-throughput SNP analysis using multiplex PCR and MALDI-TOF mass spectrometry (SEQUENOM® analysis) was used. Generally, this system uses extension of an oligonucleotide primer or probe using chain terminating nucleotides to product different sized PCR products for each allele of a SNP. The different sized PCR products are analyzed using MALDI-TOF mass spectrometry.

Disclosed SNPs

In one example, genetic markers from *D. immitis* include the sequences below (SEQ ID NOs: 1-109), where the underlined nucleotides (i.e., the polymorphic sites) indicate the nucleotide position within the fragment that correlates with resistance to MLs (i.e., the alternative nucleotide). In these sequences, the nucleotide at the underlined position is generally different than the nucleotide found at this position in organisms that are not resistant to MLs (wild-type). In the sequences below, the nucleotide underlined in the indicated sequence is the alternative nucleotide which correlates with resistance to MLs. In the heading for each sequence, the nucleotide change from wild-type to the alternative nucleotide (alternative correlates with ML resistance) at the polymorphic site is shown (e.g., C in wild-type and A in the alternative sequence is designated as C→A). The genotype frequencies for each SNP at the polymorphic sites are shown in FIGS. 1-28. In FIGS. 1-28, for markers designated with an asterisk (*), the graph presents the genotypes of the reverse complement sequence, as compared to the nucleotide sequence presented in SEQ ID NOs: 1-109.

```
MARKER 617 (SEQ ID NO: 1); C→A
AACATAAACATATTGAACTGAATCCTGCAAACAGTTCTCTTATAACGTGAACCATAACT

AAATTTAGAGAAAATATGAAAAGAAAAATAAGTTGCTTTTGCTCGTGCACCAACTCTA

ATACCCAGGAAATCAAGAAGTGATAATGAGTAATGTCATCATTAGATTCAGTAATTGG

TGACACTATCAATATTATTATTATTATACTTAAAAATACGACGACCACTTATCGTAACTT

AAAGCATGCATAATACGACTGTCATCATATTACATTTCTTCAAGTTCGTATTGGACAAG

TGATT

MARKER 714 (SEQ ID NO: 2); C→T
GACAAGCGTTGACGGGAGAGACGATATAATAATAAAGAAGGCATTGGGTATCAGAAG

GCACAATCCAATTATAAATGCCAAGGCAAAATGAATAAAATTTATGCTGACGATTTGA

TCAATTACGAAGAATTTCCGATCGGCTCGAATCTTTGTTTGTATGTGCACTACTGTTA

ACTTAATCTTTGTTTTATATACTTTTGCGTGTCATATATAATATATTCATGTCAACTGAT

ACGTTATGATGTTTTTTTGTAAATTAAGTTGATCGGAAACCTGAAGTCTATTTCAAATT

TAAGAAAT

MARKER 814 (SEQ ID NO: 3); T→C
TTTTAGGAAAATGGTGACTGTAGAGAGATATTATCGGAACGACAAGGTCCACTTCGA

ACGGGTCTTTTATTGTCGACGGATTGTGAACCAAGTTTTGGCATTCATAATGACAGGT
```

AGCTATTTTTCCATCATCCCATTTTTGTATTAGTGCAAGCAAGTCATGAGTCGAAAGA

AAATCTCAAAAGAAAAAAATGAAATTTCAGGTTCAAAGGACTGCGTCCATTATTCGCA

CTGGTTGATGAGAACGTACAGATTCCAGAGCGGCAATGCTGCACAGTATCTTTTGTT

TCACTTCTGAAT

MARKER 887 (SEQ ID NO: 4); C→T
TCGATTAAAAATTATCATCGATAAAATTCTAAAATTTATTTTAGTAAAATTATTATTATTT

TGATGAATAAGTTAACAAAAAAATTTTAATAACTTTTTGATTCGCCAAAAATCTAATTCG

TTAAAAAGTCGTTCCAAACAGATATCGCTTGTTCGATGAAAATGTCCGGTTGTTAGAA

AATCATAAATTGGTTCAATAATTTTCCAGAACGTTCGAAAAAATATTCCCTTGTATCG

GATAAATAACCATTACAATTTTCCACTCGTGTTGCATGTGTTTCTCGACAAAAATCAGC

TAA

MARKER 1514 (SEQ ID NO: 5); T→C
TCAACAGAAATCGAGATTCCAAAAAGTTTCCTACAAATACTTAATTATCAATGGATATT

TAGTTTTGTTATCTGTTATCATAAGTTCTGCTTCTTACACGATTAAAAATGTCCAAGAA

TTTTTTACTATTCAAATGAGGGAAATAAAAAACCAATGCCAATAATATCCAGAAACTAC

ATACATCTTTCTTTTTTCGAAGCTCATCTATTCCGGCCGAAAACAATGAAGAACATTAA

AATTCTTAAAAGATAGTCTTAGCCTTTTCCTTGACCACTATCTTAACTGTCAGCGCTAA

AATGT

MARKER 2557 (SEQ ID NO: 6); T→C
AATAGTCGTCTCATTACTTTTTGACTTTTATAATTCGAGAATCTTATGTAGTCCTTCACT

TTACCCTTCTTCTGTCGAACTAAGAATTACAGCATTATTTTCGAATTTAATGTGTAAAA

GACAATAGCAGATTTTGTAATTTTGTGTTAACCTCACTTTATATTTCGCTTCATATCGT

GACAGAGAATTACTATTTCAGAGAGTATTACTTGTCACCAGAGAATCTCCAGAAAGAT

TTTTATTTACGTCGGAAAATGGACAAAAATGGTTTCTTATCATTAGCACTGATAGCTAG

TTTCC

MARKER 3367 (SEQ ID NO: 7); G→A
TATCTCTTGTTGTGTGTTCTGCATTGTATCAAAGTGGGTAAATTTTGCTTTAGACGTTG

ACTTATTGTCTTTTTTAAGTTATATTCTAGTCCATGTTTTTCTCTTTGCAAATATTTTTTT

CCGCCGCCTATGATTCATTGTTTTGTTTGTAACTCTCTATTAAGTTGCTTTTAGTTTGA

ATTGTATCAAAATTTCAAACATTTAAAATACGCACTAGCACTATTTTTTCTTATCTCAAT

TAAGCGAATCCCGGAACAAGATTTAATCGATTTCCGAATCACAATTAAATCACTGGAA

AAC

MARKER 3488 (SEQ ID NO: 8); T→C
ATTTTCCTTAACAAATCATTTTCAAACGAAAAAACATTAAAAAGTGTTAAAATAAAATG

GTGATATTGATAAGAAATTAATTCAACCTGCATATCAATTCTTGTAGCGGCCATTTTCT

TAGCAAGTTCTATAGCAGCTCGATCCATATCACCTTCTTGCTCTAATGTCAATTCCGG

TTCCGGAATTTTTTTTATTTTGCCATTCTTCATCTTTTTTTATTTTTTACTGATATAGCT

ATAGACCCTTTCTCCCGTGCATGCCTGTAGGCCTGTTCTGATATACAGGCTTGTGAA

CCACTG

MARKER 4553 (SEQ ID NO: 9); C→T
TTCTGGGGTAGTTATACGGAAAATTAGACAATGAAGAGAATCAAAAAACATGCGATTT

TCAAACAGAGGAACTTTGGTACTTTTGCCTCGACTTACTTTATTTTAAAACCCATACAA

AATAAATGTTTCATTTGATTGATATTGTCGTACTAATAATTAGAGCTTCAACATTAGGA

TTTTAATAACCTTCAATTTATTTCAGAATTTAAGAAACTTACGTATGGATGGAGAAAAT

ATAAAGAATGGCGATGACAAATAAGATTTGCTATGAAAAAACTAATGCCACAAGATCC

GAATGCA

MARKER 5266 (SEQ ID NO: 10); C→T
TTTATGAACAAAATAATAAAAATTAGGATAACAGATATCAATTTCTTTTAGCTATAAAT

ATACGCTTCGATTGAAAAAAGCTTTCAAATTATAATTAAGGCATACGTTACGATATAGA

CAATTAAGTCGACATTAATTATTTGAAATAT<u>T</u>TTAAATTTTTTCTCTTTCTTTTTTCTA

TTCTCTTCCAAAGTGTCAAATAGTTATGAAATTGTCAGAAGCTAAAATGATAATATTAT

TCAAGTTTATTACCTAATCTTTTATCACCTCATTTCTTATCATTTATCTGAAAATCTAATC

MARKER 5365 (SEQ ID NO: 11); G→A
ATGTTGAATTTTTAATGAAACTTTTTCGGTGCATAAGCATTACAGATCTGTAAGCTGTG

CAAACCCTGTTTCTTTGTAAATTGAAACAAAGATCATTTATTGTTTCCAGCGTCGATTT

GACCTGGATAAATGTGGTACCAAAAGTAGATG<u>A</u>CGAGAGGTAAGTGCAAACAAAATG

CACAAAAATGATTTTGATGCACTCAAATCATTTTTAAGTTTTGTGCAATTTTCCATTTTA

TAGTTTCGTGATCGGTTGTTATTCATCAACTTGATTTTGTTTGTTTTTTGTGACTTATAT

TTCAT

MARKER 5667 (SEQ ID NO: 12); G→A
TTTGACACTTTCAGATACCTTACAAACTCATCTCCAGCACCCAATTTACAATATCGCTG

CCTAAATAAAGAATTTATTCGGATATGAGACTGTAGTTTTCATTCCGTACCAATCATAG

TAGAACAGATCTATAGCATGGTGTCCTACTAA<u>A</u>GTTGTGACTGGCTATTAAGTATGTG

GGTGTTTTACGTGTGCGTGGGTGTTTGTGCGTGTGTGCGTGTGCGTTTCTGCACAT

ATTTTCGTGCGCGGTGTCTGTGTGTGTCCGTTTGTATATGCCGAGTGTAGCTGTGTG

TATGTTCTTG

MARKER 6568 A (SEQ ID NO: 13); G→C
CACTCATAATATACCTGTCAACAAACTCAGAAATCTGAATAAAATGACGCAAAAATGA

CAAAAACATTTTATCAACCTTTTCTTCATCACTCCCCCGCATTTCCAATTTTCTTCCAA

ACTGTTTTTGTCGTGCTACAAAGTCATCAGCCA<u>C</u>TTCATTTTCTTCAAGATGGTTCGA

GACGCCATTCTTGGATTCACCCCTTATTTCAACTGTTTCCGAAGTCCCAGCAGTTGAA

GCTGAACCTAGCATTTATATCACCACCCGATGTCAAAAAATGACAGCGGTCAGAGAA

TACGACTTCC

MARKER 6568 B (SEQ ID NO: 14); G→A
GCTAGGTCAACAGTTGGTTTATTTGGACTTATACGATATTAAACATAATATCGCCTCAT

ATACACAGAAATATCAAAAAAACGAACACAGCTAAATCGAAGAATACGAACAAATGTT

TTAAAAATTATATTAAATCTTTTAATGCTCTCT<u>A</u>CAATGTCGTATCTTCCCTTTTGTCTG

TATTTCTCCTTTCGTTCCACCACTGCTATTTCTCATGCCTTTGAACTATGGTTCTCGTT

GCGTCGAATTGTCCTCGAAACTGTTGTTTCTGTCGAATTACGTCGAACTGCTGGACTT

TGTCGG

MARKER 7633 (SEQ ID NO: 15); T→C
ATATCTCACTTCTGACATAAATTGAAGTGGCACTGATTTGAATGAAATGATAAATAAAA

TAAAGACGACAAGGTAGTGGAAAAAAAAAGAGGAGAAAACACCGTTTAGTTTTGGAT

GCAAGCTCGAATCTGAGTTTTCTTGCAAACCGTA<u>C</u>ACTGATCAATTTTCTTACACAAA

CATAAGAAAAAAGAAGTGATTTTACTGTAGCTGTATCGTATAATTCAAATCATATATA

TATATGTTTCAATAATCTATACATTTATGTATATTTTTTTTGAATGGAACAGTGAATGA

TTTTAAA

MARKER 9400 (SEQ ID NO: 16); T→C
ACAAATGCCATCGGGAGAGAAATATCGTTGGCGTACTGATCACATTGGCGGTATCAC

TTCTTTGAAAACTCCAGCTGGTATTGTGTATCATTTCATGCAATACGCTATTTTTGATC

GAATATGTCGACGGCGTAGTGTTTCATTTTCCAACGCATCTTACGTTGCGTGTATGGA

TGATGACGGACAATTATTGGAATATCAAACACCGGATCGATTGCATTCCGTAACCTTG

AAACGTGACATATATGGGAGAGTAGTGCAAATAACTTCAGATGGCGAAAATATTTTCT

TCGAATATGG

MARKER 9473 (SEQ ID NO: 17); C→G
ATAATATATATTTCCATTGATAATATTTTTCATATTATGTGATGTTTGAAATTTTCTGCA

ATTGCTACATTCCGATTAAAAACTTTTATTATCCGTACTGGAGAATTTTGCTTTTTTTG

ACGGTTTGTTCAATAAGTTGTCAATATATTGTCTGCCTTAGTAAAACCTTTCTAATCTA

TCCGTTCGAATTGGAAGTTGAAAGTTCAGCATCATTCTTTTAGTGAGGTGTTTAAGTT

GTTCAATAGATATTATTTAGAACGATCTCAATTAAAATCTTCTGAATGATTTTATGTTTT

TAT

MARKER 9858 (SEQ ID NO: 18); A→G
GCAGCACATTGCACACAGTAAACTGCAAACTGAATTAAGAGATATTGGGTTGAATTAT

TTCTAATTTAAAAGGATATAATAAATGACTTTGATGATTGTTGATTTTAAGGTATCTCG

GAAGACTCCATCAGTCTCAGTGCTCTAGCAATCGCTATAGGTACTAAAAGAAAAGAAA

AGATGTCTCGTTATTCACTTTGAAATGTACATATCAAATCATTTTGTCGTATGAAATTA

AGTATATTATGTCTAATCGTATCATTCGAAATGAATTTACTGTCACTGTTAGAACTATT

TAGGCAG

MARKER 10349 (SEQ ID NO: 19); A→G
AGAGTTCAATCGCCAAGTTGTTCTTTTTCTCGCTCGCAGAGATCAAAACGGTGTTGG

CTATACACTCATTCATCAGGCTGTGATAGACATCTCTTAGAATTTCAGTGCTTTTCTG

GATGAAAACATTATTTCTCAAACATGACACTTAAGGACAATAGTGCGTGACTTCTTTG

TTAACGTACACGAGAAAACAAAACAGATGATGCTTGTTATCTTGGTGATAAATGTGTA

TTCAGAATAATGTTATATATCTTTGCGTGACAAATATCATTTCGTTATACTTCGGATAC

GCCTTTTTAT

MARKER 10520 (SEQ ID NO: 20); A→G
AACTTTACTTGAACTTTTTTGGTGTTCAATTTTGAATATTATACCAACCATTCAGAAGA

CTGTATATAGAAATGAACCTTCAAGAATTAATCGAAATTTTTATTAAAATCTTTTATTTG

AATATTTCATTATTTAAACTCATTACTATTTGCAGTATATTATTAGATCTAATGTAGAAA

AAAAAATCAGATGGCAAAAATAATATCATAGGTTTGTTTTTAAAATTCATTGCAAAATT

CAGTGCGCCGTTCCAGTCGCTCGTAATTACCCTATCCCTGAGCTTTACAAAAAGAAT

GCTTT

MARKER 10678 (SEQ ID NO: 21); A→T
AGGTATCTAGATAGCATAATAAATTACTACACAAACCGATGGAAACGCAAGTTTGGCG

TTGCGTGTTGATACAAAATATTAGAGCCAAGGATGGTATCACATGTAAAACTGCAATT

TTGCTATTTGTTTAAAGCAAATAAGAAATAAATATTTCGTTCTTATTCTTTAATTTATTTC

ATCAGATGGCTTTGTTATACCATAATTGTAAATCTGTCATATCTTAATTGCGCAATAGC

CCAAGATTCTTGTATATTCTTACATTTCACAATTTATTTTCTTATTTCTAGTTTTAGAATT

ATA

-continued

MARKER 11676 (SEQ ID NO: 22); A→G
AATAGCTACTCACAGCTTAAGTTAACTAATGGATTCTTGAATTTATTTAAGCGTGTAGT

TAAGCGATTAATATGATGGATGCCCAGAATCGCTTTGTCTTATAGTTTTGTCTCGACA

GAAAGGATGCATTGTTGTCTTGAATTTGTTCAAGGGAAAATTAAATAGGTTTCTTTCAA

TGACTCCTATTAAATTTTTTTGAATTTAGGCTTGCATTGCGTGTTCTGATCCACTATTA

GCACGTACGGGTATCGCAGTGCCATGTGATGCAGCACTATGCAAAAACCACCTCCAT

GTCACTTG

MARKER 11933 A (SEQ ID NO: 23); A→G
TCTGTTGTAAGTTTCACAATCCAGTTAATTTAAGCTCAGCTTATTTGAAATTTTCAACA

AAATTACGAAAATTACTTTCTCGGTTCATTTTTTTCAACCACCAAATATTTAGCATAATT

GGCCTGAAATCGTCAAAGTTTACAAACTTTTGTTCAGCAATCTTCTCTTACTCTTACAA

TAAACATGATTAACTTGTCGTCATACCAATCTCGTTTATAGCAAATTCTTTTCAAAAAA

ACATTGCTACAAATTTTATATCGCATCATTTCAACACGCATAATTATTTTTCATATATGA

AAA

MARKER 11933 B (SEQ ID NO: 24); T→C
TTCACAATCCAGTTAATTTAAGCTCAGCTTATTTGAAATTTTCAACAAAATTACGAAAA

TTACTTTCTCGGTTCATTTTTTTCAACCACCAAATATTTAGCATAATTGGCCTGAAATC

GTCAAAGTTTACAAACTTTTATTCAGCAATCTCCTCTTACTCTTACAATAAACATGATT

AACTTGTCGTCATACCAATCTCGTTTATAGCAAATTCTTTTCAAAAAAACATTGCTACA

AATTTTATATCGCATCATTTCAACACGCATAATTATTTTTCATATATGAAAAACCATATT

ATAA

MARKER 12716 (SEQ ID NO: 25); A→G
ATTAACTCTGAACCCAAAGACTGTTGGTTAAAATAAAGATCTATTTTAGTTATACATCT

AACATTAAAGGTTTTCGTACGGAAACAAGTAGGTTTGATAATTTTCATGTAACTGTAAA

GAACACCTGTGAAAGGGATCAGTAAAATTTGGGGGATGTAGCACGGAAATATGAAGC

TGAGTGTTTTGTACCCAAAAGTTTTTCAAATCTGCGAAATAACGAGAGGTGTAATGAT

CGTTTTTAACCAAATTTTTTGATTCTAATCCTTCCCACAGTTTTGAAATTCAGTAAGCA

TTTCTTTT

MARKER 12925 (SEQ ID NO: 26); T→C
TTGCAACAAATCAATAATAAAAGACTTGCGGCTAACAATATATTTGATTCTTTTTTACC

GTTATTATTATGACAGGTAATAATAGTATTACAAGCATATTTGTAGGTGTCAATTTTTT

CAATTCAAATTTTCTTAATTCATTATTTCTTCCTTTCCTTAATAAATAGTCTTTCCATTTA

AGAATTAACTTTTTGAAATCTTTAATGAGAAGACACAAAAGATTCCGGATAATTTTGCA

TCATCTTTTCTATTTCGCGTTAGTATTTTATGTTTTCAACAGATTTTTATGATTTAACTA

TA

MARKER 13063 (SEQ ID NO: 27); C→T
GATAAAATGGGTTCTTGTCAAGCTCATTTGGCATATCTTCGTCTTCTATATTTATATCC

TTTAATATCTTCTCTTTTTTCAAATTTTCCTTCCCGACGTTTTCCATATCGACCTCTTTC

TTCATAAATTTATCTTCCTCATTTGCCTCATTTTTTGACTTTTCATCCGTTTCATCCTTA

TTTTTCTTTTTTTCATCTCCTATTTTACCTTTTCCTTTATCAACTTCTATCTTAACTTTCT

CAATGTTTTTTTATTTTCTTTCATCTTTTTGTTTTCTTCTATTGACATACTATAACAAA

MARKER 15000 A (SEQ ID NO: 28); T→A
TTTTACGAACAATTATTTCATAAAAGATTCGTATTTTTGATTAGTTTTTAAGAATTTTTTT

TTATTATTTTTAGCCAACAAATATATTTTTCAAAATTGTTAAATTTGAAATTATAAATTTC

-continued

AACTAAAAAAAAGCAAAAAGCTAAGCCAATAGAAATAACATACATGTGTAATATAAAAT

ATAAAGTATTCGAAATGAAAATCAAAGTTTCATAACAAAAAACAAAAAATATTCTAACC

TTTTAGATTTCATCAAAACTTCACTAAAAAGTTAAATTTAAATTTTCAATTGTTATACA

MARKER 15000 B (SEQ ID NO: 29); A→G
CGAACAATTATTTCATAAAAGATTCGTATTTTTGATTAGTTTTTAAGAATTTTTTTTATT

ATTTTTAGCCAACAAATATATTTTTCAAATTGTTAAATTTGAAATTATAAATTTCAACTA

AAAAAAAGCAAAAAGCTAAGCCATTAGAGATAACATACATGTGTAATATAAAATATAAA

GTATTCGAAATGAAAATCAAAGTTTCATAACAAAAAACAAAAAATATTCTAACCTTTTA

GATTTCATCAAAACTTCACTAAAAAGTTAAATTTAAATTTTCAATTGTTATACAATGAT

MARKER 15709 A (SEQ ID NO: 30); T→C
TCAAAGACAAAATGAAGAACTTAACAAAAAAAAGGCCAATAAATAAAGGCTATTTCGT

GAAAAATCTAAAAAAAAAAAGATCTGTTCCTTTCGAATCAAGTGATTCTTCCTACTACA

TTCGTGTTGTAATTCTTACTTGTATACAGTCCCCAGTTTTTCGACGATAAAAAACATTT

CGATAAGTGAGTTTGAATTAATTGAATTTTAAAAGATCATAAAAATAAAATCAAAATAA

AAAGACCAAAATTAAGTCTGATAATTCCAGAAAACACAATAATAAATATACAAATAATA

AAAACT

MARKER 15709 B (SEQ ID NO: 31); T→A
AAATAATTCACTAATTTCTCATCATCAAATTATTTCGTACAATCGATAAATCAACGATTA

TAATAGCGAAGAGAATGAAAATTAATGTGGTGCACAGTATACGGACCCCATATACAAT

GTTCAACAGAGATGAACATTTTTTTTCTATTAAAGTTTTCTGTTCGGCGAAAGAAAGAC

ACTTTCTAACGATGCTTTCCTCCCAACTCCCCTTGCAATGATAGAGGATGCAGCCAA

GATTCGTCGACTCAAGCAGCATCACTCAACCGGCCATCACTTCGGGACCTTTTTCCC

TGCCTTTTA

MARKER 17333 (SEQ ID NO: 32); A→G
CATTGCGAATGACCGCTATGGAATATCAATTAGCAGATATTAATCGTGAATTAAGCAC

ATTGGTGGAATTTTTACGACCAAATCGAATTTCAAAAAATGCTACACTTGCAACATCA

GCAACCATTGCAACATATAACAGTACTTCGATGCGTAATGTAAAAAAGAAATGTAATG

CATCTGAAAGCTGAAAATTCATCTGATATATTGAAGCAAAGGTAAGATTATTTTTAAG

ATATCATTCTTGATGCTCTCATAATTTCTACATCAAATTTAATCAAACGATTCATTTATG

TTCATTT

MARKER 18110 (SEQ ID NO: 33); C→T
TTCTTGTTGTACCTATCATAGATGATAACTTAAGTACCAATAGCAATAGTGCAACGAT

GCAAGGATTCTGATTAATGATTATAAAAGTTTAACCAATCTTCTTCATTCCTTCTAATC

AAGAGAAAAAAAATGAGAACATTTTTATGACATTTGAAGAAAGGCAATTTATCGCTG

AAAATTCTACTGCGATATGGAAGTATCAGATAGAGAAATAAATATTAAAATATGGATT

TCATACGAAAAATGATAAAAGATAATAATTTACATTTTGGTGCTTTACTGATATGATTG

GAGTATT

MARKER 19999 (SEQ ID NO: 34); T→A
CGATATTTTTTGGACGAATCAAACCTTTTTGGGAAATCATTTGATGTCACAAGCATGG

TTTGAGAAATTTTTTTCCGAATTAGTTCTGCTAAAAATACTCCAAATGAGTCTAGTGGA

ATTAAGCTAAGCACCTTAAGTAAGTTGAGAAAAACGTTTCCATTTGACTAACAAGGCT

AGTATATCGACATGAGACAGAAATGGTTATTACTTCACTCACTTCATGAAGCGAATAC

GAAATATCTGTTCACTTTAGTTTCAATCTACTATTTTACCAATAAACGTGTTCTTTTCCG

GATAAAT

MARKER 20570 (SEQ ID NO: 35); T→C
TCTTAATTGATTTTCTTAACTCGAAACACTTGTCTTGATTACTGTGCTGTACTTTATCTT

ATTAAATTAAATAATTTCCATGACCACTTCATACCATTGACCATCAAACTTTGATGAAG

TTTATGTGTGAAGTGCCAAACAATCATTCAT<u>C</u>CCTTCAGTTTAACTTATTGCTGGTCAA

ATTCATAAAAATGCAAATTATCAAGCAGATAGTAATTCAGTGAACGTAGCGTATTCTC

GAAATTTCTTTCCTTGTATTTACCTTATATAGAACAACGTATATTTGTAGCATATATTCA

ATAT

MARKER 20587 (SEQ ID NO: 36); G→A
TTTCTGAGTTTGCGTTACAGCGCCAAATCTTCACGGAGATAGATAAAATACTTATCGT

GAAATTTTGGCGCCATGATTTAAAAAACACGGAGATAAAAATAAAATGCTTATCGGTG

ATAATTTAGCGCCATAATATGAATGAATTGAAAA<u>A</u>ACAATTTGAGTAGAAACATGACAT

AGAGTTTTCGTTTTCTGGCTACGAAAATGGATGAATTTTTCTGGAATCGAATTCAGTC

AAAGAAATAGGAACGTTGTTACTAAATGATCGAAAAGCTTTCTAAAATTAAATTTATGA

CGTCTAAG

MARKER 20698 (SEQ ID NO: 37); T→C
ATCTAAATCTTCGTTTTATAGTGGTAAGACTTCCATTTGCTGCATTCTTGCAAATTAAG

CTGTTGAAAATACTTTTTTTTTTTGATAGATTTCCAATTTAATCATATTATAAGAAGAATT

AATTTCGAATAGAATTTTTAAATCATTTAAA<u>C</u>TTTAAGTTTTAAAACTAATATAAGTTAT

GCAGATTTCGCGAAAAGTCTCATTTGTTAATTCAATTATTCCAAAATGTAATAATTTT

ATAAATTCAAATTTAAACTACTACTAACTTCTGAAGTCAGGAGCCAGTAGCAACAACG

TAAT

MARKER 21554 (SEQ ID NO: 38); A→G
AACTTTACATTTATATTCAATTTTTTTTATTTTGTTGTTTTAGAAATTTGAAAATGGG

TACTAATCAGTGTCATTTGCAGCCTCTTAGACCCTCTTTATAACGACCGATTCGATGA

AATACGTCATCAATATGCCAGTTTATTGTTC<u>G</u>GGTGGAGAATGTTTTCAAAAGTTGCT

GAAGTGATGAAGTATAGTGAGAATGCACCTTATTCAGCACCATTAAGAAGTAAATTTT

TGCTTTGGAATTTGACAAAGACAAAGCAGGAAGTTGACAACGATGTTCTGATGAAAC

GGTTTCGA

MARKER 22174 (SEQ ID NO: 39); A→C
GTCTATTTTGGCTGTCTTCTAATAATTCATTTTGTAACCTTTTGAAATATGATAAATGTA

GAAATTTTTCTTCCTGGTCTATAATAGTTTAATAATGTGTTGTAGTAATAGTTTTGGT

GCCGTTGAAATATTTCAATGATATGCTATCG<u>C</u>AAAATTAGGAATTCAAATCAAGGTTA

CAAGATAATTCAAAACAAACAACGTAAAAATGAAATAATTTCTTCTTCTTACTTACCA

ACAGGCATATCATCATCATCCTCAAATTCATGACTATATTTAACATTGTCATATTTGAA

TAATC

MARKER 22254 (SEQ ID NO: 40); C→A
CGACGCAAAAATCTTTCAAATTGTCACCCAGTTCTCTAAGTGATTCCAATGATGTTGG

TAAACATTCTGCATGATGTACCGGGTAATGAACTACCAAGTTGTTTTTTGCTTTTAATA

CAACTCGCAAAGATTCTGAAAACCATGAAATTA<u>A</u>GAAAGATTAAAATAATCTGAACTCT

TTTTTTCATTTTTCCTTGAACTTAGCAATATACTGAGTTGGATAAAATTTAGAAACGAA

ATTTCGCAAATTTATTCAGTAAATTCAGGAAAACTCGGTTTCGGTATTCTAAATATAAA

TAGATA

MARKER 22259 (SEQ ID NO: 41); A→G
GTTTCTTTGGTTTATCTCAGTAAGATTTGGGCGGAAATTTCAGTTATACTTTTCATTTC

CATGTGCTGTTTTAAATTTCTTCCATATTAGTATAATTTTCAAATAATTGTAGCGTCACT

GGTTTATTTAAGGATAACAGGTTGGACTGCAGTGGCTGAGAAGTGTCTTGCCGGTCA

ATTGTTTGTTGGTGATCAACTTGTACGAGTTACTGATATCGACATATATAATACACGG

CAAATTCCATTCGTTTTCAGTACTGCATCAAAAACGGGATTATCGGTACTTTGTAAATC

GCAGTAT

MARKER 24708 (SEQ ID NO: 42); C→T
GACCCCTGCTCACAAGGCAGTTCCCACAGACAATCACACATCTAATCACACACATCA

ACTCATCCGACGTAGGCTATCAATAAGGAAAATTGCATTGCTTTATCGTCTAACTGTA

ATAAACATCTACATAATGAAATTATTTCGCCACTATGACAACTAATATCGCCCAATGCA

AATATTTGTCTCAGAGTTATTCCCTTTTAACAGCTGTTGAACGAATAGATAGGACGTC

ATGTGGATGATCTACTTGTTTCAAAGGTTGAGGTAACACATGAAACACATGAAAACGG

TAATTTAAAA

MARKER 25276 A (SEQ ID NO: 43); A→G
AAAGAATGGTCAGCAAGATGTGGAAAATCGATTACTATAGTTGAAGTATGAATCGAAG

AGGTTTTTTTAAATTCTAAGAGAACGAATAATCGGCAAAGAGAAAGTTGAGTAACCTT

ATTTTGCCTTGTTTTCAGTCAATTTATAATATGCGGTTAATTGTGTTAAAGAAAGTACA

AGGTATGAAATCTAAGCCAAGAAATAAGAGAAAACAGCTAATGATTATTTCTGCATTTT

TTCTTTTTCGACACAAACTTGGAACCAGAATCAATTGAACTAGTAATCAGATTTTGATT

ATTGCTT

MARKER 25443 (SEQ ID NO: 44); T→C
TTAGATTTTGCTGAAGCATTGTTGGTTAGATCGATGAAAATATAATTATGAGAGATTTT

GTTGAAATTCAGCAACAAAATTATTATTCATGTCTTCATGCTGTCAGTTTTGTTTTTATT

TCTTCTTTGACATCGGTTATATTTTTGTCTTCCAACAATATAAAAAAAAAATTATAATCA

ATTGGTAATCAAATTAAAACTCTAATTGTTAGCTCCCTAAATCAGCTTTAAAAAAATAA

TTGCTTAATTGGTATTTGCTACTATTAGCAAACTGAAACTATCCTTTTCTCGAATGGTG

AAC

MARKER 26447 (SEQ ID NO: 45); G→A
ATGAGCTGATATTTGATATGCATATTAAAAATAGGGTAAATTACATTAAGTTAGATATC

GTTCGGATAAATTAATTAGAAAAAATGTTTACCAATTAGATCGCAATGATGTAAAATTT

CACGTATTTTTATTCTTAAGATTTATTTGCAAAATTCAAAAATATGTCTTATGAAAAATA

ATATTTCTGTGTAAGAACAAGGGACCGATTCACTTGATTTATTCGCAAACAATCGAAA

TTCAAAATTAGTAATTTTAAATATTGCTTTATTCAAACCATACCAATAATAATTTGAGAG

ATTT

MARKER 26730 (SEQ ID NO: 46); A→G
ATTGATTGATTCAAATAAGAAATTTAAATTATTTCCCCTTTTTTCAAAAGATTTAACAA

ATATTATTTATTTGATCTCCTCGTTCGTTCTTATCTTTTTGATTATCAATCCATCCTCCT

CCATCATATAGCTAATTTATTTTTTGCATCGTAAATCAATTGATGTATGATTGATTTCTT

GATTATAAAAGTTAGAAGAATTGAATTGCTTAAATTTAATTATTGATAATGAAATATTA

TTATATTTCAAAATGATACGAAGAAATATGACGATGATAAGAGAAAATATGATATTTATC

-continued

MARKER 26974 (SEQ ID NO: 47); C→T
TACGATAAGTTATTTTATTTTACACATCTCCATCCTTGACTAGTGTCCGTGCCGACTGT

CGGACTTGAACCGACAACCTACTAATTACAAGTCAGTTGCTCTACCCAATTGAGCTAA

GCCGGCCATCTAGAATGTGCGACCCCGTCGTGGTACATCTTCTATAATCGTTTGGTA

TTCAGGACTCTCTTCTTTCGTGGGTGGAGGATCTTGATACAGTTGACTATTAAAAATA

GGGCCTTTGTTAGTCTGTTACAACTCATAGACAAAGGCGACAATTTTAGCTTACATCT

TACGTTATGC

MARKER 27080 A (SEQ ID NO: 48); A→G
ATGGTAGAAAATTATATGAAAAAATATCATACTAAAAATATAACAGATTGTTATAAGGT

ATGGTTTAAGAATTTACAACAATTGATTATTTATGATAAAAAAAAAAAAGTAAATCAGT

GAATCATTAAGATAGTTATGATAAGCAGTTTGTATTCGGTAAAGCGAATGATTAGAGG

AATTATGGGACGAAACGTCTATAACCTATTCTCAAACTTTTAATGAGTATGACGTGTCT

TGCTTGCTTAAAATTATTTCAATGATCATTTCACTTTACCAGTATGATCATGATTAGAC

TTGAA

MARKER 27349 (SEQ ID NO: 49); T→A
TTAGTATCGATATTATCACAAATGATATCACTTTCATCAATACTGGATACGATTTTATTA

GTATCATAATTTTGTGGCTCGCATTCCGAAAGTTTTACACGTAGAAGATTAACCTGCA

ATATGATTTATTTTATCATTTTCGAATATCCAACTTTGAAATAATTCGAAAATGTTGAAA

AATTTTGAAAAATTGTTAACAAAATATTACAAAAATATCAAATGAAATTAAATAACTGTC

CATTTCAAAAAAGAAGAAAAATTATGAAATTACCAATTAAAAACAGGACTTATTAATT

AAA

MARKER 27461 (SEQ ID NO: 50); G→T
TGTGGAAATAAAGTACAATTAATTGCTGTTCGCTTAATAATATTATTTTCATTCTTGGC

TTTTTTTTCTTTCCCCGTGATATTATAAAATATAGTTTTTTAATTTTAACAAATCGTCAT

AATTATTTAAAAAATACTGAGGTGAGTAAATGTAATTGGTTGCTGGAAAAAAGTGGG

TGATGAGAGGTGAATGAAAGCAGAATAGTTTATGATTGCATCAAATTTCCTCCTTAAT

CTGTGATTAAAATCAAACAAAACCCGAAAAGTTTCTTCTTCGCCTTTTTCTTCTCTTTG

TTTCA

MARKER 29128 (SEQ ID NO: 51); T→C
CGAAATCCGCCGCGTGCATTACTTTGCGCTTGTTGATTACGACGCATTTGTTCGTCG

TTGATAACCTTATCAATCATCATACGTCCGTTACGTATGCAATCAACATCGCCAGTTA

GGCTGAAATCAAATGGATGGCGATGATATCAAAAACAAAAATAAGGAGTATTTGCTGA

ATCATTTCTTTTTCTGTATTATTATCAAAATTTTCTCCTTTCCATTGTTTCCTTCTTAATC

AAGTGAATGCTCATTTCATTTTGAAATAATCCAACGTAATAATTCCCCATATTCCCAAT

TACTTTC

MARKER 29168 (SEQ ID NO: 52); A→G
AGAAATATTAAACTTTGAAAAGATGTGACATGTTCTGTAACAAAAGCCCAAAATTTCGA

CTGCTGCGGCTTGAAGTAAAATTTTGGAATATGCTACATCAGTAGTGCAACAGATGGT

TCGATAAATAGTGGTAAGTGATGGGAATCCTAGGAATAGATGGGAATTGTATTTCAGA

TATAAATTTGATGCATATTTTCATAGTTGATTATATCTACGATCACACGTTGAATATTCT

AAAAGCAAACTGTAATTAACTAATTGAATTTGAAAATTTCCAAGAATTAAAATTGGTAA

CAAAAA

-continued

MARKER 29455 (SEQ ID NO: 53); T→A
ATTGTCAGGAATGAGAAGCAAGTTTTGGATACTTAAGGGATGAATGGAACACATACAT

GGCAGAAAATGTTAGTAATCAAACCATTTAAATTACTTAGCCACTATGCTAAACTTTCT

AGAAGTATGGTTGAACGTTTAAAAACCTTCGCAAAAATTGTATTAGATTATCTTAATCT

TCCCTACATCAAAACAGAGAATTTTTGTTCTACGACGTGAGTCTGCATGTATTAAGGA

AGTTCGTATCATGACGTAAATATCCTGAGTGATTATTGAATTCAGAAAATGAGCTTTTT

CATTTGG

MARKER 29816 (SEQ ID NO: 54); G→A
ATATGAGTGTTACATGTGTACGTTACATGTAAATATTATATGTTATATGTAAAAATGTC

ATGTATAGCATCTATTCACGTGTACGTACACGTGTATATACATATACATTGATACTTAA

TACGTATACGCATGAATGAACAGATATTATATATTTACGTACACTAGACTCACATGTAC

CTCTGTATACGCATACATGTACAGATATATGTTTGACATACGTAAATTCATATATGCTT

TTATTTATGCTTATATTAATTGTCACATACATGCCTTATATTTTCGTTGTTATAAACACA

TAAA

MARKER 30575 (SEQ ID NO: 55); T→C
GAAAATAAAATTAGCTGAAAATATATGCGAGGTAAAGCACACAGAAGAATTAACTTAA

GGTAATATATTGTAAGAATTTTTATATTCGGCGCACCTAATAATTTTTAGACCGCATAT

GCCCAGTATTTGAAACTGGTAGCGCTGTTCGTACTTGCTGTTGTCCATGTTATGTATA

TGATACCATTCCTAAATACTTTTGCGGCTGTGGTTTCCAGTGTTGATGTGACTGGTAT

GATGCCTAACACTGGATCCTTCCATCTGCGGCATTTTGTTGAAATTCTTATTGATGTG

AGCTGTTTA

MARKER 30991 (SEQ ID NO: 56); A→G
CAACTGTGAATCATAAACATTACTTAAATTAATGAAGCTAGTTAACGACAAATATATTT

TTTTATGTATCAGTGCTATCATATAACATAAAAACTTACTTTCATTAATAAATGAGCTCA

AATATTGACTTTTGTCCAAAATGCTCAAAATGTCGTCATAATATTTGAAATGAAGATAA

TTTCACGCTTTTCGAAGCCTCCTCTCACGTCTTTTAATCTTCTTTTCTTCTTCTTGCTC

TAATGGTTCTGCGAAAAACCACGGTGCAATAATCACTTTCCATAATTTATACAGTACAT

AAGC

MARKER 31796 (SEQ ID NO: 57); A→G
CTGCTTAACTCTTTTCATTTTTCAGAGAATCTTCTCTAAAATTGTGAATTGATCCAAAC

CAAAGAATATGGATAATGTGATTCGAATTCCTGGAATTTAGATTTTGAGAGTTTTGAA

GTTTTTAAAGAGATTGAATTTCTGTGACCTTCTGGTATATTTGATGTCATTTCGGGATG

CGTATTTTTGCCGAAAATTTTTGGCCTCACTGCAATCTTGTTAAAAGTCAAAAAAATTC

AATCGTAGAATTTCGGGTTTACCTGATATTACTGGAAATCTCTGATCTTTGTTCTAGAT

TGCTGT

MARKER 32164 (SEQ ID NO: 58); A→T
ATAAAGAATTTGCAACTCTGTATACCTTTTTGCAGTGCAAAAGCGGATGAATTCTTCA

CTGCAGTGTGACAGATTCCTTTGATAAAATTGCTTCGTTCTTATGTAAACTTGGAAATT

CTCGGTAGTTATGCTTTTGCTAGTTGAAAATGTTCTGCTCTTGTAAAACATGCAAAAA

GAGATTATCTTTGTTCTATTATGGAAAGATTCTTTTGAAATTTTGACGACTGAGAAGAC

AAATTTTATCCCAACTTGTCATCTGCAATAAAAATTTTTCCTGACCTGTTTCTTAACCTT

CCAAGT

MARKER 32223 (SEQ ID NO: 59); T→C
AAAATCAAATCAATATGATCAGATAACTCATACTTATCTTACTGAAAATTCCTCATTCA

AGGGAAATAAATAATTGCAATTCTTGATTCCGATCATGGATGATTTTCAAGCAAATTAC

CAATGATATCTATCGATAACGATTACAGCATACAGCTATAACTTATTATTGATTGAATT

GATGAAAATAATTTTACCAGAAATTTATCAATGTTTATCTCATTGCAGTATACGATGTT

TAGTGTGACAACACTTTTTCTTGGAATAATTGTGCATAAATCATTGATTGCATTTAGTA

TTGGA

MARKER 34439 (SEQ ID NO: 60); T→C
TCCTGCCCACATTCTTTCTACTTTAGATAATCAACAGGAGTTAGTTGAAAGAGAAGAC

TAGGAACAGTTGCAACTTCTGAATCTTTCTGACTTTCTTTCGTTTTGTAAATTATTTATT

TGTATAAATTTAAAATTCGAAGAGAAATAATCCAAGGTCCAACTTCTTTTTCTGTTAGT

TCTTGCGAATGCTCCATCAAAATGCAAAAATATGATTAGAATTCTGATGGAAATTAACA

AAATCGATTAGATAAGAAAAGTACAAAACAGAAACTAACTTTTTCTCCCATTTTCATAT

TATAG

MARKER 34903 (SEQ ID NO: 61); T→C
TCATTGCTTTAATACTTTTTAACGAGAATTTTCTCGATCAAAATAAGATCTGCAATTGA

TATACGTCAATAAGCGAACATTAGCTGTATTACACGCTAATATTCACATATGATGAAC

GTTGTAAGCGTCATACATCAACATATATCCATCCGATAAATAATGACCACTACACATT

GCTACCAACCATCCTATCCCGCCACTATTTGAAATGAACTGAGAAGGAGTTATCGAC

ACAGGCTTCCTAGCAACCAAACAAAAGACGAGACAGATGAATAGATAGACAGACAGA

CGAACATACAA

MARKER 35336 (SEQ ID NO: 62); A→G
AGATTCTGGTTATTATTGTATTTCTGATTTATTTAATCCCAACTTAAAGATTCATTGGCT

ATTGTTTAGCATCTATATCAATTTTATAAATAAATAGTAATACCTGATGAAAAGCAATAA

ATAATTAGATGCAAATTTTAATTAGATACAGTTTGATGGAAAACATTGAAGCCATGTAC

AACTAATTTATGCATGTTGAATTATGCATGCATAATTAATTTATGCATGACAGCAAGTT

TGGTATAAAATTAATTTTGTATGAAGATAAAATTTTATAAATAATGATAATAATGCTGGT

AA

MARKER 36040 (SEQ ID NO: 63); T→C
ATTATTGAAAAGAATAATGTAGCTAATTAGTTGAAGCTGTTAAAAGTAAAGCTAAAAAG

ATGATGGAAATTATTCGTATAAACATTCTTTGTAAACAAACAGTCATTTCTGTGAATAA

ACAATTATAATTATAAACAATACTTTTCAAGACAATAAAAAAATTAGGAAGCATTGTTG

TGATAATCAATAGTTGATAGACTGTCAATGTATTTTATCAGTCGTGCTGCTTTTTTTC

CCTTTCTTGACTCATTTATTTTATTATTTATTGATAGAATGTCAATATTCTAGTCATTTG

TTAT

MARKER 37881 (SEQ ID NO: 64); T→C
ATCTTAACTTGCTTTAAACAAATAAATTAAAACAGCCCAATGTTCCAAGAAAAAAAGAT

AAGTTAAAAGTGGGGTGTCCAAAAATTTATGAATTGAATTGGACAGTTATTCAGATCC

TGAAAATACGCTTCTCTGATCACTGCAAATATTCCCGATAAATAAGTGAACATTAGGT

TAATCTTAATTTTCCCTTAACTTTCCTTAGCCTTTTTTAAATTTTTGGATTATTCAAGCA

TTTTTATTGCGGTATCGTTTTTGTAAAAAAAAAAGTATAATTCAACATTCAGGCTCGAC

GTTATG

-continued

MARKER 38622 A (SEQ ID NO: 65); C→A
AATTAATAAAAAGAAAGGAATACGATAAAATATCTATTTTTTGAAACTAATCAAACATAT

TCCTCACTGCTCACCGGATAGTTGCTTTCTAATTTTACATTAAGAAATATATTTTTTTTT

TTCAATAAGGAAAGTTATGCAGACTAGGAGAATTCTACTCTGAAGAAGAGATAAGCAT

GTTAGAATTATTAAAATCTATGGAAATATCCTTAAAAGAATGCCTATAGTAGCTCTGAT

TTCGAAAAAAAAGCAAAAAACAAAATAACAAATTCTGCTCAATTGAAATAAAAAACTT

TCCT

MARKER 38622 B (SEQ ID NO: 66); C→T
TAAAATATCTATTTTTTGAAACTAATCAAACATATTCCTCACTGCTCACCGGATAGTTG

CTTTCTAATTTTACATTAAGAAATATATTTTTTTTTTTCAATAAGGAAAGTTATGCAGAC

TAGGAGCATTCTACTCTGAAGAAGAGATAAGTATGTTAGAATTATTAAAATCTATGGA

AATATCCTTAAAAGAATGCCTATAGTAGCTCTGATTTCGAAAAAAAAGCAAAAAACAA

AATAACAAATTCTGCTCAATTGAAATAAAAAACTTTCCTTCAACTTCCAGCATCACTGC

TGTGA

MARKER 38622 C (SEQ ID NO: 67); C→T
AACTGCTAAAAAATTGAAACTAGTGTTAGATTGATAAGTGGGCAGATTAAAACCAATT

GTGTTATTGGCCCGTTAATTAGTGACTCTGAATAGCTATGGCGAATCGTATAGTGTTG

TACCGACGACGTATCTATCAAATGTCTGCCTTGTTAAATTTCGATGATAGTTTATGTG

CCTATTATAGTTGTAACGAGTAACGGAGAATAAGGTTTCGACTCCGGAGAGGGAGCC

TGAGTTGCCACATTCAAGGAAGGAAGCAGTCGCGAAGATTACCCACTCTTAGAATGA

GGAAAGAGTGAC

MARKER 38622 D (SEQ ID NO: 68); C→T
GAAAACTAAGAAGTAAGTGAAATTTCTAAGTTCTTTCCCAGAAAGGTTAGATCCAATA

TTTGTTTTCATTTTAGCATTTTTATCCAATGAAAAATGTGCCCAATAAATACTTGTATAT

AGTATTGCATTTAAAAACTTCAGAAAGCACAATGAGATCTAAGCTCAGAAATATGACG

AATACCAATCCTTTTCCTAGTCTTACCGCTTCTTAACTTTTGTGTCGCTTTATAAAAATT

AAAAATAAAAAGTTGAACAATGGGAATTACATCATTTTCATCTGAATGGTTTATTTCCT

ATTCT

MARKER 39492 (SEQ ID NO: 69); T→C
CTTCCCTAGCTATGCCTTTTCGTCACTTAAGCTTCNNNNNNNNNNNTCTAGCTACGTAT

CGTTATCATTTATGCTTCTTTAGCTACGTTTCTCCATCATTTATGCTTCCTAAGCTACG

TATCTTCATCACTTACGCTTCCCTAGCTATGTCCTTTCGTCACTTAAGCTTCTTTGGCT

GCGTGTCTTCATCATTAATCTTCTTTAGCTACGTATCGTTATCATTTACGCTTCCTTAG

CTACGTCTTTCCATCATTTATGCTTCCCAAGCTACGTATTTTCATCATTTATGCTTCCT

TAGATA

MARKER 42291 (SEQ ID NO: 70); G→A
GATCTTAAAATTCTATGAAACTTCTTCTGCATGGTATTGTTTCCAACAGAATATAATGA

CAATAGCAACAGTATTGGTTATATAAAAATATTGACTGCAGCAGGATTATATTTCAAGT

TCTTTTAATTTCATTTATTTATTCTTTCATTTACTTTTACTGTTTTTATGTTTTTCTTCTTT

AAAAAATATGATTTCTCTCACTGTTCTCTTTCATCTATCTATATTTATTTGATAATTGCT

TATATGATAACTAGCTAAAGGGAAATAAACTTTCAGTCATCATAGCTTCATTTTAGTAAA

MARKER 42411 (SEQ ID NO: 71); A→T
CTATACTAATCAGTCCACTATCCATTTTTAGGTTGCAAAAGTTGCAATGACGGTTTGAT

TTCATCCTCCAATGCAATTTTGAGTCTCAATCTCGAGAGATAGATCGATCGCTTTTAG

-continued

CTTGATTTAGCTTGGTTAATGTTGTGAGGGATATTGGGCAGAAATTCTGTCAAGCGTT

ACTTAATGAAATAGTAAATGATCACTGATATTTATTGTTAATGATACTTGAGCTCTCTA

GATTATGAACTGGAAGGTTTTCGATAGAAATAATCGATACATATATTAGAATCGACTTC

TTTTTTC

MARKER 45689 (SEQ ID NO: 72); A→C
TCATCTTTTTCACATTTCATTTAATCATCATTTTATCAATTCCTATTTTTAAACAAATTCT

TTTCAAATATTCTCTCTTTCCTTCTCTTTTTGTTTTCCGCTTATTCATTCTAATGATGAA

CAGATGTAGAAAATTTGCATTCTATTGCTCACTACAATTTTGAGTAGAATATATTTAAT

TATTTGATTCGAGACAGATGGTTATAGCCTTTAGCTTCAGCTTCTCGTTCAAATTAAGT

ACTTGTGACCTTTCCAAGTACCATTAAAGCTTTCCTGCGTTTCCTAATTAGAAAAAAAGG

MARKER 45719 (SEQ ID NO: 73); G→A
GCATTTTAAGTTAAAAGTATCACGCTGCATGACACCTCACGTTTGCTATCTCAAATTG

AGTAGGTTAGAATCTTTTTTTGGCTACTATTCAAATATTAATAATAAATTGCTGCAAAC

AGATTTCACACCGGAAAAAAATTAAATTTTTCTAGCAATGTTTTAACTCCCTTATTAAAT

ATTTATAGAAAATCGACTACTTAAAAAGAATTGACTAACATTTCTGAATCTCTGCAGAG

ATTTATAGATGGATTAGCATCCTACAAGTTTTTATCTTTTTGCTATATTTCCATTATTTT

TTTA

MARKER 46063 (SEQ ID NO: 74); T→A
GATAAGACGTCTTATTTTGTAATAATTCAAAAATTAATTAATATAGAAGTAAGATCTTGA

TAATAATTAATATGCTCAAATTTCTTAATGAGAATATGTTCAGGATGAAGATGAAGTGA

AAGAAATTGATAGATTGAGGAAGCAATTGCTAATTGAAACAGAACAGCTCGTTTCCAA

TTCTCTTAAAGATTTACTGAAGAAAATTTATTATCCACTTGAAGAAGCTATTGATCTCA

AAATTCATCAGAAATTAATTCAACAAATTGCTGCCTTGTTGAAGTGTATTAGTATCTTG

GATAA

MARKER 47481 (SEQ ID NO: 75); C→G
ACCGCAAAATACCTAAAAATTTCTATAACAACGATTAACACGGCCTCGAACTGGAAGC

ATATTAATCCATGCGTGGCTCAAACTTCAATCATAAAGACAAGATCTAGAGATCAACA

CAAAATGGTGAATTGTTACCCTATCGTTGCTAAAGTTTGAGAGAAAAAAGTGCTAAAT

CAAGTAGTACACCAAATTTAGTTAATATTAAGAAATCAATTTAGTACTGAATTTAAACA

AATGAAATTTTACGATAAAATAAAAAAGTACCTGATCAAACAGCGTCCTCCCGTTATTC

CCATTGCT

MARKER 47722 A (SEQ ID NO: 76); C→T
TATAAGACTAGTAAACAGATCGTAATATAATAAATATCGATTTTATTTTAAATTTTCGAA

AACTTCCAAATCTATCGATATGAAATTAAAGATCAATTTTTAATTTCCATAATATATTTA

GATTCTATCCCAACATCACTCATCTTTATGTCAACTTATTTAATTCTCTTATTAACATTA

TATTTCTTGTTTACAATGATAAATTTTATCAATTTTCTAATATGATAGAACATCTTCATC

ATCTGAAGATATGCTTTTCTCATCTTTGTAACAATTCGTATCGCTTCTGATTTTACTTTC

MARKER 48750 B (SEQ ID NO: 77); G→A
GTTTTATTATTGCTTATTGAATAGTGATAATAACACTTTGATATGATATTGTTTTGTTGC

GATCATTGTATTGATTATAACCTTAATTAAACGAGGATATTATGGGAAATGTATTTATT

ACAAAATTAAATATGAAAGGTTGAAGTCTTGACGAAACTTTCAAACACATTTCTCGAAT

TTTCTCTGCAAAAATATCGTTACGATTTTTGGAAATTATGAAGTCCAAGAATTCAATCG

-continued

AGAGTTCGCCATGTCACTTTGGCTAGTTTCGTTTGTTTTAATATTTCAATCAAAAGTC

AATT

MARKER 48750 C (SEQ ID NO: 78); G→A
CCTTGGATATTGTTCTTGACATCGTTGATCAGAAGGTCACCGTAGTGTTCGGTGAGC

GAGATGGAATTGGACTCAGGTTTATTCTCCGTTTTTTTCATGTTTTTGAATTTTAGAGA

GAAAATAATGTTTGTCTGAATGGTTAGCAAACTAATTAGTTTTTAAGTTATCAGGAACT

CGAAGTATCTTCTTTTGCACTTCTTTAACCTTTTTCATCAAATTTTTTAACAGTAACAAG

ATTTTTTTGAGAATTTTCAAAATATTTTTGACTTCTGATGATATTTGATGAGAAAACCAT

CACTG

MARKER 48790 (SEQ ID NO: 79); A→C
AGAGTATTATTATACATGATGATGATGATGATGATGATGATGATGATGATGATGATAT

GATGATGATGATGATGATGATGATATGATGATGATGATGATAATGATAATGATGATGA

TGATGATTAATTGCTTATTTTAATGATTGATAACTTTAAAAGAAATCATTGAAATTTGA

TCGAATAAAAATTTTCTTAAAAAAAGCATTTGCTATTTATATAGTAAACCTATAAAAAT

TACTTATTTTTATTACTAATATTCATTTGATTGTATGAAAGAGAAGAGAAAAAAAACCTT

TGCA

MARKER 49731 (SEQ ID NO: 80); T→A
TGGTATCACAGCACTGGGTTTAATTTCAACAATCGGTTGACGATCTTTTCGGGATATG

CCTATACCCAGAAATGAACGTATGCCAAACGATGGTATGTTTGATGCAACAGACGAC

GTCAACTTAAAATGTGTTTTTTTTCAAAAATTCAATATTTTTAGTTTAAAATTGCACGT

CAGTAAAAATTAATTCATAATAAATCTCTTTGATTTCTTCGTTCTCCTTTTTTTTCAGAA

AAAATTGAAATTTTACATACCTGATTTCCAAGAGCATATAAAGCATCACTTAAAGCATT

CTGCGA

MARKER 49824 (SEQ ID NO: 81); T→C
TCCTTTTCATGATTTGTAGCTAACCAATAAGATGTGTATATGTTCATATATTTACTCTC

CCCTGACTCTTTTACACTCTCATTCTCTCATTTGTTCATTTAGATAAGTAATATGCGCC

TTTCTCTTCCTGATTCTCTCAATCTTTCATCCCTTCATCTCCTCAATCTTTCTCCCATTC

TCTCAATCTTTCCTGCATTGCATTCATTGATGAAACACGATAGTATTAATAAGCATAAT

TTGATAAATTGAAATAATTTTTTTTNNNNNNNNNNTCATTCTCTCAATCTTTCCTGCATT

GCA

MARKER 49904 A (SEQ ID NO: 82); A→G
TTTGAATTAACAAAATATTAACAATTACAACTATTTCGGAATTTAATTTAAGAATAATTT

AATTAATCAATTTCCTATTTTGTATTTTAAAAATTACCACAATAATTATGTAATTTTTGG

GATATTTGAAACTTTGAAAAAAGTGGTATTGTATTTGAGAATAAATTAATTAATGTAATT

CTTGCTGCTCATCGTTCCATAACTTACAAATATTTCTCGGTATTTTATTTGAGATAATT

CTTATCATTTCTTCCATAGCTTTCAATATATTTATAACTTATTTGTAATCACTCTTATCAC

MARKER 50378 (SEQ ID NO: 83); A→G
TTGAGATATCAAATCAAGCGTTGCATATTTATAGTACACTGGTGTAGCTGAAATCGCG

AAGAGAACACGAAAATCAGAGAAGTCAATGGTTCCTTTGTGTTGGATTTCACATGAAA

GCATCCTTATGTTGTACATGCGTGATTACAATATGATACAAGATGTAAGCTAAAAATT

GTTTTATCTTTGTCTATGAGATGTAGTTCATACTCTATAATAAAGTCCCAACCCTTAAT

TCTCATATTCACAACCGTATCAGAATCCAACACCAAACCATTATAAAGAATGTTCTTCG

TCGAGGCG

-continued

MARKER 51565 (SEQ ID NO: 84); C→T
CCACTATCGCTTACACTTTCTTTATCCTGTTCTTCTTCATCTTTCGTTTTGGACTTTATT

TTACTGTCAGGTGACAAGCAAAGTAACGATGTTGGACTTTGCGAAGATGTGGATGGT

ACGCTAGAAAAAAAATGAGGATTGGTTAATATGTCTAATTATTACATCGCTTTTTTTA

AATCTTTTCTAAAATTAAACTGAATAATCAACTTATTTGCTATTCAGTTTATCTTATTTTT

TATCAACAAAATTCGAGGAAACAAATCGCTTATCAGAATAATTGTTTTGATCAACAAAT

AAAG

MARKER 58162 A (SEQ ID NO: 85); G→A
CAATCCCACAAATTCAGTGTGTCGGCGGGTCAGCGAAGGGAAAGTTTGAACCGAGG

GTATGTACAAATTGTGATAATTTTGTGATGACGTAGTAAATTTCATAGTTTTGCATGCT

TTAATGTTGATAGTCGCACAATCCTACGTTGATTAAATTTAGCTATTAGATATCCTACT

AAATTATGTTGTTCATAATTTTTGTTTTTAAAATGCTCCACTTATATTTTCAGGTTGTGC

AGTGCTACAATAGGGGTTATGACGGCAATGATGTCCAATGGGAGTGTAAAGCGGAAA

TGAGCAATC

MARKER 58864 (SEQ ID NO: 86); T→C
TCAGATAAATTGTATTTGATGTTAATTCAAAGAAGAAAAAAATAATCAGTAGAATATGA

ATCGAATAATATTCATACAACCAGTTTATTCATTATTATTCACTTTTAACGTCTAAATGA

CGTAGCTACGCTTTTTTTCTCGCTTTCAAGCCTTTACTGACCAAGATTAATGTACATTC

TGTTGAACAAGATTAATCGACATTCTATCGATCAAGATCAAGCTTTTACTGATCAAGAT

TAATAATGACATTCTTCTGTTGATCAAGATTAATCGACATTCCATTGATCAAGATTAAT

CGAC

MARKER 62666 A (SEQ ID NO: 87); G→A
CTCTCTAAAACCTATTGGTCACTAAACTTGCACTGACTAAAAACTATTGGTCATCAGA

CTTGTGATTCATTGAAAAGACCGTTAGCCGCTAAAATTATGATTCACTAAAAAAAATCT

ATTGATCATTAAATCTGTAATCATTGAGAAACTACAATCATTGGTCATTAAGTTTGTGC

TCTCTAAAACCTATTGGTCATTAAACTGACTAAAAACTATTGGTCACTGAACCTAGAGT

CTATTAAAAAAAAAATCATTGTATCAATAAATTTATTGTTTACTATCAAATCCATTGATT

ACTGA

MARKER 62666 B (SEQ ID NO: 88); A→T
TCTAAAACCTATTGGTCACTAAACTTGCACTGACTAAAAACTATTGGTCATCAGACTT

GTGATTCATTGAAAAGACCGTTAGCCGCTAAAATTATGATTCACTAAAAAAATCTATT

GATCATTAAATCTGTAATCATTGAGAAACTGCATTCATTGGTCATTAAGTTTGTGCTCT

CTAAAACCTATTGGTCATTAAACTGACTAAAAACTATTGGTCACTGAACCTAGAGTCT

ATTAAAAAAAAAATCATTGTATCAATAAATTTATTGTTTACTATCAAATCCATTGATTAC

TGAATA

MARKER 7060 (SEQ ID NO: 89); G→A
AAAATGTATCAAATTCTTCGATGCCATAAATTATACAGACTTGATTGGCATTTTTCTA

ACTTTCATCATGAACCATTCTATTTCTAAATTGATCCATTACAAAATCAACTTTGTGATA

TCATCAATCTCAGTCATAACGAGAAATAATGATAATATAAAGCGACTATCATTTGAATT

TCCTGAATATTCAGATGTAATTACATCTTTTTTTTAATGTAATCAAATTTCTTGCCAT

CAATAATTTTTCAACATATGCTTTCATCGACTGCCTTATGCAGATCGTAATGATGACAG

CCA

-continued

MARKER 12056 (SEQ ID NO: 90); T→C
ATTGATTAAAAAGAATCAACATTAAATTTTTGATATAGTCGAGAAATCCTTCGTGATAA

TTCTTTTAGAACAATTCTTTACACTAAACTTGTATTTACTTGCTTATTATTTGTCTAAAG

ATACTAACTATTTGTCAGTGGAATTTATGATCTTGGCATTATTGCATATAACGCTTTCC

TAAAATCTGAAATTTTTCAGTATTTTAAAAACTAAGACGATTATTAAATATTACTCAAAG

CTTAGAACTTTGATTATACTAATCAAATCAAAAATTTCATCAGCGATTTTTGTTGTGTC

ATT

MARKER 16261 (SEQ ID NO: 91); T→C
ATTTTTTCCAGCAGAATTGTCATCAAAAATCCCATTTTTGATATCCTCTTCATCGAAAC

TTGCTCCTGAATCCAGAGAACAACGAAGAATGTGTAAATCTATTTCAGTAGCCTGCTC

ATTGTGCAATTCAGCGACTTTATTTCTGTGCTTCAAGCTAACTTCTTCATTATGCCACT

CCTCTTCTCTCGCTATTTTTTCGCTATCTAATTCAAAATCTTCGTCTGAAACGGAATCA

ACTCCTGACGATGTACTCGACACTGATAATATTTTCATGCCGATTTTTCTCTCAAACG

AATCTTT

MARKER 23195 (SEQ ID NO: 92); C→T
GAATGAAGAGCAAAAAAATAGTCACGACCACCTGCAATAAAAACAGCATCTCCGTAA

AAATGATTGAATTGATTCCCGAAATACGAGTTTATCAAATTGAGAATTATGCAAATTAA

TTATCAGCATGCAGATTTACTGATTTTATATCTCTCATACCGAAATTAAGGTGATGTTT

TCCATTTCTTTGTTTCCACAATGTCTTCTTTGTGAATCGTTTTGGATCAACTATTAATC

CGATCGAATCAATCCTCCAAATATGAGTTTATTCAACGTAACAAAACATTGTCCGAGA

TAATCAAA

MARKER 28579 (SEQ ID NO: 93); T→C
TGGAAATTTCGAAATCGAAAGGATGAAGAAAAAGGATCCTTGATCTATACATTAAATA

TCACCATATCAACTAGCATGGCAAGTCAAAGTAATGTTATCATTTAAATAAAAAGATG

AATAGTAGGACTACAGGTTATATTGTTAAAAGTCGACAAATTTGGAGTAATTGACAGA

GATCAACGATTAAATGTAATGGATGATCTTATCTTCTTTTTTCAACTACGCCAAAATGA

AAATAACAATTGAATTTGTCGAATAAGAAACTAACATTTTGAAAATAAGATTGAACATT

TATAAAT

MARKER 48869 (SEQ ID NO: 94); G→A
GGTTGGATCATTATCGACAGAACTTTAGAAGTTTCTTGATAAGGACGAAAAGAAGCAG

CACCATTGCTGATCTAAACAAGGAAAAAGACCTTTTTTGGAATATTGAAGTTTTTACT

GATAGGTGCGTGCTGTGTACTGTGGGCATAAGTACAAGCTTCATGCTCCGCAGCGT

GAATACGTGCTGCATGCATACTATGCAGTAAAGGTGCGTGTCGTATTGCTCAATAAG

TGTATAAATTGCTGCTTTTCTTGCATAGTTAAATATTTTGTTTTCATTTTTTCCGCTATT

CAAAATAAAT

MARKER 53021 (SEQ ID NO: 95); G→A
GTTGGGATTTCAGACTCTCACTCGGTGTCGTTTCACAGTGATATCTGAATCGAAGTCA

CAAGCAGGTATGAATGCATAACAACTAATATCCATTGCAGAAACAAGGCAAAACTGA

GAAGCTCGAGCAATATAGCTATAGAAGCTGGTACCACAGATGACATTACATGGTATTT

CCATTTCAGCTTCACAAACATTGTAAATAGCTTGCTTCGATGATTCAATATCTCGTTCT

ACGATATTCTTAAAGTAATTTTTATTTATTTGAAGTATAGATTACATCCATGTTCTATCT

ATCATTTC

MARKER 7986 (SEQ ID NO: 96); G→A
TGTTCTGAACATCTCTTTTTGATTATCTTTTTTAATTCCTCCATTATTTTCGTTTTTTTCG

TTGTGAATTAATATTGTTTGTCTTTGATTCAGATGATATTTTCGGATCGTAAATAGATG

GCATCGGCATAAGCGTATTGAGAAGCATTCAATGGTGCACTCTTGCTTCTTTTTTTTT

TGAAATCTTTCTCGATAATCAAATAAGTGCAGGATGCCAATCATTAACAATTTCGTTCC

ACTTTTTCAGTTCTTATTCTTATAACACCACATCTCATTTGCAATTTTGTCGCCAATGAT

TTT

MARKER 48094 (SEQ ID NO: 97); C→T
TTTTTTCGAGGTCACTCTGGAAAATAAATCATATTTTAAAAAGACATAAAATAAAAAA

TATGTATATATAAGAAAATTTTTACTCTGAATTTCTTAAGAAAATTCTCGATTCTGTTTT

CCATAAATTCCGGAATATGTTGTCCCTGAATTAAGAATTCGATTCCTTGCACACCATT

ATTTCGTCTAGTTCCTGTGTGAACAATGTAACCTGGAAATGAACACATAAACTGTAAT

ATTTTGAGCTTAAAATAATTATGAGGATGCGAAACTGAAGATATTCATAAATGTTTAAA

AAAAAA

MARKER 6568 (SEQ ID NO: 98); T→C
GTCCATGCATTGCTTTTCGGAAGTTAGTGTAGATTCAGTGAATATTTAATACCAGTCT

CTTTCTAATTCAAAAGAGCCTCCCATTTCTTTTTTCAGTTTCAGTCTCTGAATCAGAGC

GTGTAATCTACCACTCCATTGCCGAAAACAGCTCGATGTATTTCCTGCTACGTAGTGT

TTAGAATTGGCGTATGCCACTTGCTCATTATTCGCGCATGAAGTGTAACTGTGAATAG

AATGATACTACTGTTAGAAGAGAATGCGTTCACTTTATTTAACATTATACTGATTCATT

TCTTCTTT

MARKER 17022 (SEQ ID NO: 99); C→T
AGTGAACGAGAAAAAACAGAAGAAGAGATAGCACATCAAGATCGTGAGAAATTAATT

AGACAAGAAAAAGCTCGTCTTACACAAATATATCAGGTTTTCTTTTTCTTGCTTTCGAA

AGTTATTTGAATTATCTCATTTCTTTGAATTTTATAAGAAATAATTTAATTTTTTTTGAA

ATTTTGCCTATTGAGCTCTAAATTTTGTAAAAAGTTTTCTAGGATGATGTTAGCAAAGC

AAAAAGAAATCCAAAAGTGATGGTAACAAACAGGAAGATTTTATAGTGAGGTACGAT

AATACG

MARKER 55751 A (SEQ ID NO: 100); A→G
TAGACAATATCATCCTTCCTTTTTTTTTGCTCAATTTCTCTGCTCATTGCTTTGATGATA

ATGGTAGGTGGTATAATGAAACGAATAGATAATTGATGTTCGCAAACATTTGCTGTTA

AATTTCAGTAAAGAAATTGACCTTTTTGCTTTGTGTTGGATGTTTAGCTTCATTTTCTT

CTTGTTCATTGTCATATTCATTCTCTCAAAACTTCTTGCTTAGCGATGCTAATATAAAT

ACTGGAAGAATGCCTTTGCTTTGTTTTAGTTGTAAATCATCACCAAGGTATTTTTTTGC

AAAAT

MARKER 55751 B (SEQ ID NO: 101); A→G
AAGATGAAACTAAAAAAAATTATTTCGAAAAAAAGAAAATAAAATTAATGAAATAAAAG

CAAAAATGAACAAACCGTATTAATTTTAAACAATAAACAATATCGAAATCGAAAAATGG

ACTATTATTGATGAACTATATTTTCAAAATGTGAAAGGTCAAAGTTTGTTTCAATTATG

ATAAATACAATTTAAAATAAGATTAAGCTAACAAATAAGTTGAGCAAATTGATGAAACA

AACAAATCAGAATATATTACAGAAAATGATATAACATGAAAATATATTAGACCAATTAT

TTTTA

MARKER 15893 (SEQ ID NO: 102); T→C
TTGAAGTTTTCAGATAAACTTTGATAAAAAATTGTTCTATGAATTCTCAAATTTCAATTA

GTGATACTTATTTCGAAGGTAATTATGCCTGATTGAATCTTCAATATCAACAAAATGAA

AATTTTAGTATGATTGTTAACTCATACACCTCTAATTAAAGGTATTTTCTTTATCCCATG

AAATGAAAATTTATTAAGAACTTAGAAAGCTACGGTATGCCTTTGATGCAAAGAAAG

ATTCATTTTCATTAAATCATGTTTAAAAAAAAGAGCAAAGAGCAAAAGGTGATGAAAGT

TTTT

MARKER 25462 (SEQ ID NO: 103); C→T
TTCTATACGAAATATTTGTCTGCCATAAATCTACTCAGGAACTCGATACATCAAAACAT

AAGTACGCTTGCTCTTTATTTTTCGTTTGAAAAATAAATAGATCATTTTCGCACTTACA

TTTCAATTTCAATTGCTTTATTCATATCTTTCTGTTTTTACTTACTGGTATTTAACAGTC

GTTGTTCACAATTTAATGATCTATGAAACACCATTTAATTGTATTTGGACTAACTTTTC

GACAAGCAAAAGATTAAAATTGTCTTCAGATACAGTTATAAATTTACATTGAAGATAAA

TGAA

MARKER 33494 (SEQ ID NO: 104); A→C
TAACGATCTGTATATCAATGGAATAATATTCAGTTCATGTTGTACTCGATATGAGATAG

AATTACAATTTTGGAACAAGATAATCTCAACAGCTATTTTCAAGAATAGTTAAATTAGG

ATACCATTCAAAGAAACTTTAAAAAATGATTTCCATACATTAATGCTTTTTGTGTTTTCG

CTCTCGACCAGAATCCAGGAATTGTCCATTATCATCAATTTGATTAACTTTTATCTTTA

TTCTAATTCTTCAACATTTCTCTAATTGATATTAGTTTCAATATTTTAATAAGTAAAAATTTA

MARKER 17935 (SEQ ID NO: 105); T→C
ATAATGTGTTATTGATCAAAGGATTTTTAGTTACCTACCAGATGGAAAAAAAGCAAGTT

TACGAAAACAGAAGTTAGCATCAACTTTCATCCATGGTTACACCGTATATAATCCAAT

CGACTCATACTTTATGTTGATCTGATTTTATAGCAGATAACTAGTTACCTTGCTCAGCA

GCAGCTAAATCCTTTCTATTTGCTTAATAACAGAAATATTTTTCATTAACAAAGAAATTA

TACTCCGTGTTTGACATTTCATTTTAATTTCGTTCCAAAAATGAAAAAAGCTTCGTCCG

GAAAT

MARKER 48561 (SEQ ID NO: 106); C→T
ATTATTTTGTAGTTTTTCATTTTTTAGTTCAATTTTCCTTTGCTTATTTTAAATATGCCAT

TCTTTATTCAGACTCATAGCGAATGCATATGTTCATTAATTTTTTTAGTTACAGTTACAA

ATTCTCAATTTCTCTTTAATCATTTTTTTTTCCAAAAATAGTCTGAGCACTCAACCATTC

ATTCAACAATTGCAGCTTTTTTTATTGGAGCCTTGTCAAATTATCAATTCGTTTCCATG

TTTATTATTGAAATAATAAACGGTATTTAGGATAACGAAGTTCGCTTAGCTTCTTTGACT

MARKER 42003 (SEQ ID NO: 107); T→G
AAAAATTCAGGTAATGAGATCAGTAATTTTTTTGGTCACTTTGCTGTTTCTTATCAGC

TCATTGTTATCCATATCAAATGAGCGAAAGTGTGTATCACATATTGGCAGAGTGTAAT

CTATGAAGATTTTGCGTATCAAAGTAATTATGAGAGAACTGATAATTTTATTTTAAAGT

AGTAGAAAACTCGAATTAAGCTAATAAATAATCGGTTGATATCCATGAAATGAATTACT

AATGAAATGGATAATTGAGTAATAACAAATGATATTCATGAAGAAAGGCAGGTTTTTTT

TAATAG

MARKER 29566 (SEQ ID NO: 108); C→T
TATACTTAAAACAAGAAATACAATTAATGCCAATAGCAGAGTGAAACTTCTGAAAAATA

ATGAGTTGAAACTGGTAAAATTAACATTTTATTAGAAATTTCAGAAACTTATGACTCCT

CATGGCACTATCACAAAATGTTTGAAAAAAATTGACAGCTCGCGTCGATTGCAAAAAT

```
CATGATTCCTGATATTTAGTATCGAACATGTGACAAATAATATAAAGACCTAACCATAA

AGCACTGAAACAACTCGCGGAAACAAAAAATTAATTTGCATAAACACGGAATACGATC

AGAAAAT

MARKER 33868 (SEQ ID NO: 109); G→A
GAATTTTTTAGAAGGCTTGAAGTCGAGAATATTAGAGACTATATCGAAGACTTAAATA

ATCCTGGTAATCTTCTGTATGAATCAAAATTACCTCGAACAGAACCATTCAGCACATC

ACGAGATAATTCATGGAATGAAACTAGCCAATCAGAGCGTTGTAAAAGAAGAAAGTTA

TGAAATGACCTTAAAATCAATTTAAAGCATGTCCTCGCCATATAAGCGTTGAAAAGTT

AGGATAGAATCAATTATCAAAAAAATATGTTAACTAGATCTTATCAATCAAAACATCAG

AAGGAAAA
```

In another example, genetic markers from *D. immitis* include the sequences below (SEQ ID NOs: 110-127), where the underlined nucleotides (i.e., the polymorphic sites) indicate the SNP nucleotide position within the fragment that correlates with resistance to MLs (i.e., the alternative nucleotide). Those markers were identified after genotype frequencies comparison between susceptible individuals and confirmed ML resistant individuals. In these sequences, the underlined nucleotide at the SNP position is generally different than the nucleotide found at this position in organisms that are susceptible to MLs ( -continued MARKER 17709 (SEQ ID NO: 114); T→C
TCGTATTTGTTGTATGTAATATAGAAATATTGTTTAAATTCAATATGTAGAAAAAATTTC

TANNNNNNNNNNNAATTAATTACATATTAACTCGTATTTGTTGTATGTAATATAGAAATA

TTGTTTAAATTCAATATGTAGAAAAAATTTCCATAATAAAGACGAACAGCATTTATAATT

ATCAATGATAAGTTGAAATTAATTCATCAATGATAAGTTGAAATTAATTTATTTGAAATA

ATTTCTTTGAAATTCGAATATAGACGAGAATTTTTTTTTTTTGCTAATCGTTTATCAAAT

MARKER 47141 (SEQ ID NO: 115); T→C
TCTAGCAATATAAATTACAAGAATATGCCGTCCAAGTATTTCAGAATTTATTATTAATTT

GGATAATAATACATTGTAAATACTGCGTATTCTGGATTATTATGCACTGCATAATAACA

TGCAATTTCGTCTACATATCGCGAATAAACGCCAAAAGATTTCTCGATAAAAGAAAAT

ATAAGAATTCGTAAATGAATGTTGTGTCAGAGATATGTGTTAATTCATAAGTCAAGATG

TTGTAAATCGATCCATATTAGTAATCATATTTACGTGCTCGTAAATAAAAGCGGTGATT

CTTGT

MARKER 48750 A (SEQ ID NO: 116); A→G
ATCGAAAAAGATGATCTGATGACGGAAGGCGAAATGTCTGCAGAAGCTAAGATGAC

GGAAGAAAAAGTGAAGAAATGAAAGAAGAAGCTGGTAAAACTCAGAAGGAATGTAA

AACTGGAGAATCGAAAAAGATGATCTGATGACGGAGGGCGAAATGTCTAAAGAAGC

TAAGATGTCGGAAGAAAAAGTGAAGAAATGAAAGAAGAAGCTGATAAAACTCAGAA

GGAATGTAAAACGGAAGAATCGAAAAAGACGATCTGACGACAGAAGGCGAAAAATC

TGAAGTAGATGAGCC

MARKER 63962 (SEQ ID NO: 117); A→G
ACTAATGATAAGAAACGGAGCCGACGATTTTAGGAAATGAATAATAACGACATTGACA

ACCATTGTTAGAAAATTGATAGTACTGATAATAAAAGCTAGTTATAGAAAATTGATAAT

AATAATAAAATTGCTGGTAGCAAATGTCTAGAAGTGATAATAAAATTAATGATAGCAAA

TGGATTAGCAATGATAATTAAACTGATGATAGCGAATGGATTAGTAATGATAATAAAAT

TGATGATAGCAAATGACTAATAATGGTAATAAAAGTTAATGCTAGTGATAACTTGTATT

TTAAGT

MARKER 6372 (SEQ ID NO: 118); A→G
ACAGTTTATAGTTACAATATTCTCCGGTGACTAACTGTATTTTACAACTTATAATTATA

GATTACAAAATATATTATAGTAGTTTTATAATTACAGTATTCTTAAGTGAATAACTATAC

TTTACAGCTTACAGTTACAGTAGTTTTCTATGTTTTTGAATATTAATTTTACATGGTTTT

TCCTAGTTTCAGTTTCAAAATTTTCAGATATTTTATGTGTTAAAGCAAATTATATTCGAG

ATATAAAAAGTACTGGTCATATCTTACAATTCTCATCCTTCTATATTGGAAAGAATTGAGT

MARKER 15611 (SEQ ID NO: 119); T4C
GTATTGGGACCGCGTATCGGGAAATCTGAAAGAAGTCTTTAACAGTATTTTAAATGAA

TAATTCAAATCGTTACTTCTTAATATATTAATTTATGCGTATATATGCAGTACATAGCAT

TGCTTAAATTCTTATTTTTCCGCGGTTAAAACCCTATGTAAGATAAGGGAGGTGATTG

TATCTGCGCCGTACTCCTTGTTTTAATCTACCTGCTTGTTGTATATCCTCCACATATTG

TAACTGCAGCTTCACATTTGCATATATAGTAAGGGCATCGTTGTCTCCAGAAGAGATA

TATTATC

MARKER 46432 (SEQ ID NO: 120); T→A
GCTGCCCGAATGTTACAATTAGGACGAAAGTAAAAGTAGTTGACTGTAGGTATGACG

ATAAAGGAAAAATTTGTATCTTAAGACTTTACAATTTCTAAATATTACGTGTTTTATCGT

GCTAACATCACGAATTCCATATTCACAAAAAAAATTTTGTAGAACTCCATCTGGTTTGG

-continued

```
ATGAATTTGCTACAGTTGAACTGGATGATGGAACGAAATTGCAAACATCTCTTATTGT

TAGTATTTTCTAAATTCTGTGAAATTTTGCAACGGCATTCATGTTTAATTATTAATTTGG

AGAAAG

MARKER 29594 (SEQ ID NO: 121); T→A
AAATAAGCAAATCCGAAAGTATTACATATACGGACTAAATATTGCCATTCATTCGGGA

GTATACCATTGCAACCATTGGTATTTCATTTGATCGAGAAAACTAGTTTTTGTAGTTTG

GGATAAAGAGAAATGGAGAGAGGAACTTTCATGATCAATTTCTTTACGTACTGAAATT

CATTTCTATGGATGTTCTTTTTCTATTTCATTCTCCTCAGCAAATACAGTCCGAACAGT

CATCAAATAAGTCTAAAAGGCATGAATAATATAAACATCAGCAACTTTTTAAATGAATG

CTTATTA

MARKER 26784 (SEQ ID NO: 122); G→C
ATTTCTATAAACATCTCTTGCATTGATTAATTTAACATGTTGCAATAAATATTTCTTACT

TTTGAATGTATCATTTACTAGAAAAAACTTCAATCGAGGAAATAAGTTTTAAAATAAATT

CATATTTGAATTCATGTCAGTTCAAAAATTCTATTACTATAATACATGTCTCTTGGTTGT

ATCTTTTTTCTTTTGAAATAATACAATCAAACGGTTTCCTAAATTTTCATAGACATCAT

ATTTTAAAAAAAAATGCATTTGAAAATTTTCGAAAATCAATGAACTTAATTGATGAAAAA

MARKER 51661 (SEQ ID NO: 123); C→G
GCATGTGTATGTAGTATTTCTTTGTAAACAACATATCTAATCTGTCTGTCCCTTTAACA

TTATAGAATAGTCAGTTAGTCCGCTATTTATTTTAATAACAAAATATCTCACTTAACTTC

CATTTCTTTCCTAAATAATTTTGTTTCGCTAGATCTTTCCTATAATTTTCAAATTTTCAA

AAATGAATTAATCTTTTATTTATATATGTGTATGTATGTGTATGTATGTATGTGTACGTT

GCATATATGTATATGTATGTGTGTATGTGTGTATATGTATATGTATATGTGTGTATGTGTG

MARKER 7819 (SEQ ID NO: 124); G→C
TATGCATAATGTGCGACCAGCCAATAATGTCTTCAAACCATAATTATGCAGAAATAAA

TTTTTTCCAGAAATAATTTTTTTTTTTTACATATACTTCCGATCTGTGAGAAAATACAT

TTGAAGTGAAGTGTGAAGCAATGCTACTTTTTCAAACAACATTGTGAAAATGGATTAA

AACGCACCAATGGAGCAAGAGATCGTAAGTTTCGTTCCGCATGTCCTGTGGCAACGT

GTAAACCATCCGTTAACGATATATGATGTAAAAGCCGACACACCCAAATTAAAATCCA

TTATAAACA

MARKER 26704 (SEQ ID NO: 125); G→C
AAATGGATCGTATTCACTTCGTAAGAACTTAGTGAACGAAAAATCAAACCATCACAAT

AACTTTACTTTTTTTCTTTTTTTACTAAACACACTATCCTATGAAAACAAAATGTCCAAA

TAGATTCATATGATAATGAACTGTGAAGTTATCCAATCTATCAGTTCTCGAAGAGGGA

ATAAATAAAAACATTAAGCAACCCACCGATCTTCGCTGACCATCTCCTTCTTCATTAG

CAAGAAGCAAATCTTGTGGTGATATTTCTGCAACCATCTGCAAAATAAAGCACGAAAA

ATTAAGGA

MARKER 14329 (SEQ ID NO: 126); C→A
TTTGATATGCAATCAACTAACCAAATCAGAATTCAATGCATTCTGATAAATTTCTTCAA

TATCGTGCATCAATTCGACATCATATTTTGACAGTGATGCTACCTTTTTAGCCGTATTT

CGGAAAAATATGAATTCAACCAGCTGCGTCCCAAAATTTAAGGCTGTAGCAAGTCCA

GCAACAACCAGCCCTACAACTGAAAATTCTAAAAACTGGTTCACGTGCTTATCATTAA

TAATTTCAACACTATCACTATCTCCACATGAACTTGATCGATTATAATTTAGTAGAACT

GAAAAAAA
```

MARKER 56169 (SEQ ID NO: 127); T→G
ACAAATTCGTTTTAATATTGGATTACATTGAAATTGCTGAAATAAAGTGGAAATATTGA

AAAGCATTTTACAATATTTGTTAACAACATTATATTTAAAGAATATACACCTTGGTTTAA

ATGGTAAAATAATCTCAAGAATTTTCATTAGGTTAATTTTTTTTATTTATTTATATTCAC

AAAAAATTGTAAAAGAAAACAAAAACAACAATAATAACGGTGACAACAACAACAATAAT

AATAACAAAACTATTTGTTGTGATTTTGCAGCATTGATGTAGTGGGGATCTTTTGGAGCGA

The genotype frequencies for each SNP (SEQ ID NOs: 110-127) at the polymorphic sites are shown in FIG. 29 (Table 1). In one analysis, genotype differences of susceptible individuals were compared with confirmed resistant individuals. In a 45 second analysis, genotype differences of susceptible individuals were compared with grouped confirmed resistant and LOE individuals.

Kits and Methods

In embodiments of the invention, probes of the invention may be provided to a user as a kit. A kit of the invention may contain one or more probes of the invention. For example, a kit may comprise a probe capable of determining the genotype of a nematode at a SNP position in one of the fragments disclosed herein. The kit may further comprise one or more reagents, buffers, packaging materials, instructions for using the kit and containers for holding the components of the kit.

A probe of the invention may be one or more molecules that are capable of binding to, or associating with, the nucleic acid sample to determine the genotype of the nematode at one or more specific positions (e.g., polymorphic site) in the fragments disclosed herein. For example, probes may be used to determine whether a wild-type or alternative nucleotide is present at the SNP position of one or more of the fragments disclosed herein. An example probe may be a nucleic acid molecule or oligonucleotide. Example probes may contain a label or labels. Example labels may include radioactive labels, enzymatic labels and/or fluorescent labels.

An oligonucleotide used as a probe or primer may comprise any size, shape and composition that is suitable for use in the context of the invention. Preferably, an oligonucleotide of the invention may comprise DNA, RNA, synthetic nucleotides, non-natural nucleotides, altered nucleotides, or combinations of one or more thereof. In one embodiment, an oligonucleotide of the invention may comprise locked nucleic acids and/or peptide nucleic acids.

In embodiments of the invention, an oligonucleotide may comprise a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, or more nucleotides.

In embodiments of the invention, an oligonucleotide may encompass, without limitation, a primer or more than one primer, e.g. a primer pair, such as a forward primer and a reverse primer.

A primer may be an oligonucleotide that may be used to initiate DNA replication. Typically, a primer is a short oligonucleotide that may be about 10, about 15, about 20, about 25, about 30, about 35, about 40, about 45, about 50, about 55, about 60, about 65, about 70, about 75, about 80, about 85, about 90, about 95, about 100 or more nucleotides.

A primer may be used as part of an approach to detect the genotype of a nematode at a specific location of a gene. For example, a primer may be useful in amplifying DNA such as by PCR, RT-PCR and qRT PCR, for subsequent analysis, such as by Southern blot, sequencing, HRM (high resolution melt) or SSCP (single strand conformational polymorphism).

As used herein, an "aptamer" may be a nucleic acid or a peptide molecule that binds to a specific molecular target. For example, in solution, a chain of nucleotides may form intramolecular interactions that fold the aptamer into a complex three-dimensional shape. The shape of that aptamer allows it to bind tightly against the surface of its target molecule. Because of the diversity of molecular shapes that exists for nucleotide and amino acid sequences, aptamers may be obtained for a wide array of molecular targets, including, but not limited to, nucleic acid molecules, enzymes, membrane proteins, viral proteins, cytokines, growth factors, and immunoglobulins.

A probe of the invention may be prepared according to standard techniques known to a skilled person. For example, a probe may be produced synthetically, recombinantly or may be isolated from a natural source. In one embodiment, the source may be a biological source, for example, from a microorganism (e.g. a bacteria or a virus), an animal (e.g. a mouse, a rat, a rabbit, a goat, or a human), or a plant.

In the context of the invention, "a probe" may mean one probe or more than one probe. One or more types of probes may be simultaneously used in methods of the invention. Probe design and production are known in the art. Generally, a probe may be produced recombinantly, synthetically, or isolated from a natural source, e.g. from a cell, an animal or a plant. However, a skilled person would appreciate that probe production may depend on the type of probe at issue. A preferred probe may be a nucleic acid molecule (e.g. a primer), with or without a fluoroflor or dye. A probe may be linear or in the form of a hairpin, with a fluoroflor, with or without a quencher or another fluoroflor (e.g. for FRET analysis). It could also be an antibody that specifically recognizes the DNA (or protein) sequence. Another probe could be based on a RNA molecule. What would be preferred may depend on technical considerations, stability, cost, ease of use, etc.

In embodiments of the invention, probes of the invention may be provided to a user as a kit. A kit of the invention may contain one or more probes of the invention.

Uses of the Methods and the Kits

Methods of the invention and kits to carry out the methods may have research, medical and industrial applications. The invention finds broad application in the management of heartworms in infected animals and in detecting ML resistant *D. immitis* nematodes in an area. Representative, non-limiting applications of the invention may include the detection, quantification and/or diagnosis of the existence of individuals or populations of *D. immitis* that are not susceptible to normal doses of ML for prophylaxis or therapy. In one embodiment, the ability to detect and quantify nucleic acid molecules of the invention is valuable insofar as it will instruct a practicing veterinarian to alter chemotherapeutic regimens for animals infected with *D. immitis* nematodes that have decreased responsiveness to MLs. Identification of ML resistant *D. immitis* nematodes may instruct a veterinarian to switch from ML therapy alone to therapy that may include an alternative agent or alternative agents, such as an adulticide (e.g. arsenic based drugs), diethylcarbamazine, antibiotics such as tetracycline, and combinations of one or more thereof in order to achieve cure and/or to minimize the spread of the resistant strain. Alternatively, a veterinarian may adjust the dosage of a ML and/or treatment regimen using a ML in the treatment of an animal infected with a ML resistant nematode. Typical recommended dose rates for ML preventatives include, for example, 6 µg/kg for ivermectin; 500 mg/kg for milbemycin oxime; 3 µg/kg (monthly) moxidectin; and 6 mg/kg for selamectin. A veterinarian may also combine one or more of the treatment approaches and therapies noted above in any combination suitable to treat an animal infected with a *Dirofilaria* spp. nematode, e.g. a ML resistant *D. immitis* nematode. For example, a veterinarian may treat such an animal with an adulticide, such as an arsenic based drug, and then follow up with a microfilaricide, such as a ML or diethylcarbamazine.

In one instance, an arsenic based drug may be used to treat an animal infected with a ML resistant *D. immitis* nematode. An arsenic based drug may include, but is not limited to, melarsomine dihydrochloride. Melarsomine dihydrochloride may be used, for example, at a dose of 2.5 mg/kg, twice, 24 hours apart. This may be repeated in 4 months depending on the response to the first treatment and the condition, age, and use of the animal. However, a skilled person would understand that the dosage may vary depending on the severity of the infection. For example, an infected animal such as a dog with severe (class 3) disease may receive one dose and allowed to recover for a few months before receiving the complete set of 2 doses.

In another instance, diethylcarbamazine may be used to treat an animal infected with a ML resistant *D. immitis* nematode. Diethylcarbamazine may be used, for example, at a dose of 25 to 50 mg per pound of an animal. The duration of administration may depend on the condition being treated, response to the medication and the development of any adverse effects.

In another instance, an antibiotic may be used to treat an animal infected with a ML resistant *D. immitis* nematode. Said antibiotic may include, but is not limited to, tetracycline. A tetracycline, such as doxycycline, which targets the *Wolbachia* endosymbionts in *D. immitis* may be used, for example, at a dose of 10 mg/kg/day for 40 days.

In a further instance, another anthelminthic agent may be used. Such other anthelminthic agent may include, but is not limited to, acaciasides. An acaciaside may be used, for example, at a dose of 10 mg/kg/day for 7 days.

In another embodiment, the detection of *D. immitis* nematode populations with the above mentioned genotypes may instruct the use of alternative agents, such as diethylcarbamazine as a prophylactic to protect susceptible animals, e.g. dogs.

In one instance, diethylcarbamazine may be used to prevent an animal from becoming infected with a ML resistant *D. immitis* nematode. In this regard, diethylcarbamazine may be used, for example, at a dose of 3 mg per pound of an animal once daily.

In another embodiment, a kit of the invention may be useful in as a commercial product in the detection of ML resistant *D. immitis* nematodes. Such a product may be suitable for use by, without limitation, a veterinarian, a physician, a pet owner, a farmer, a zoo keeper, an epidemiologist, or another consumer in need thereof.

EXAMPLES

The examples are for the purpose of illustrating an example and are not to be construed as illustrating limitations.

Example 1—Susceptible and LOE Populations of *D. immitis* Parasites Used in the Studies The various susceptible and LOE populations of *D. immitis* used in these studies are described below.

a. Susceptible isolates from Missouri, USA. Thirty five (35) *D. immitis* adult specimens were obtained from two dogs originating from an animal pound in Missouri. The history of the dogs prior to the animal pound is not known. The dogs were not subsequently treated. The *D. immitis* isolates were believed to be susceptible to ML heartworm preventatives.

b. Susceptible isolates from Grand Canary, Spain. Seventy-one (71) *D. immitis* adult specimens were obtained from 12 dogs originating from a shelter on Grand Canary. The dogs were never exposed to ML heartworm preventatives and heartworm prevention is not practiced in this region of Grand Canary.

c. Susceptible isolates from Grenada, Wis. Ten (10) *D. immitis* adult specimens were obtained from 2 dogs originating from Grenada. The dogs were recruited from poor, remote areas of the island where ML heartworm prevention is not practiced.

d. Susceptible isolates from Italy. Six (6) *D. immitis* adult specimens were obtained from the Po Basin in northern Italy. *D. immitis* seroprevalence in dogs from this area is reported to be approximately 60-70%. ML heartworm preventatives are commonly given to dogs in this area. But, there are no reports of LOE (loss of efficacy) in Italy.

e. Loss of efficacy (LOE) isolate case 1. Microfilariae (mf) were isolated from a dog that was previously described (see Bourguinat et al.; WO2011/120165). The dog was a male neutered Labrador mix, born in February, 2006, that weighed approximately 31 kg. He was a rescue dog from New Orleans, La., U.S.A., collected by the Boudreaux Rescue Crew, New Orleans, and subsequently transferred to Canada where he was adopted in January, 2008.

The dog was brought to the Main West Animal Hospital (MWAH) in Welland, Ontario on Jun. 6, 2008 (day 1) for a check-up. Blood collected from the dog tested positive with a heartworm antigen test (PETCHEK® PF; IDEXX Laboratories, Westbrook, Me.) and contained microfilariae of *D. immitis*. On Jun. 11, 2008 (day 6), initial work-up (bloodwork, thoracic radiographs, physical exam, urinalysis) was performed. Auscultation revealed a mild increase in bronchovesicular sounds in the lungs and a grade III-IV/VI heart murmur. The remainder of the physical exam was unremarkable. Thoracic radiography revealed moderate right-sided heart enlargement and an interstitial lung pattern in the caudodorsal lung field. These examinations indicated a diagnosis of class 2 heartworm disease.

Adulticide treatment was initiated on Jun. 11, 2008 (day 6) with 2.5 mg/kg intramuscular melarsomine dihydrochloride (IMMITICIDE®; Merial Inc.). The treatment was followed by two intramuscular treatments with 2.5 mg/kg melarsomine dihydrochloride on July 9 and July 10 (days 34, 35). Over the following 90 days, in order to eliminate circulating mf, the dog was treated on one occasion with milbemycin oxime (MO) and on two occasions with IVM (see Table 2). On days 159 and 160, four months after the last dose of adulticide, the dog was again treated with 2.5 mg/kg melarsomine dihydrochloride intramuscularly. The subsequent diagnostic testing and microfilaricidal treatments are summarized in Table 2. During the treatment of the dog, several heartworm antigen tests were conducted, including DIROCHEK® (Synbiotics Corporation, San Diego, Calif.) and PETCHEK® PF (IDEXX Laboratories, Westbrook, Me.), which are microwell ELISA tests, and SNAP® PF (IDEXX Laboratories, Westbrook, Me., a membrane format test designed for rapid in-clinic use (see Table 2).

To perform the Knott's test, 9 ml of 2% formalin and 1 ml blood (collected in EDTA) were mixed in a centrifuge tube. Centrifugation was performed in a LW Scientific EZ Swing SK centrifuge at 3000 rpm (604 m/s$^2$) for 5 min. The supernatant fluid was discarded. A drop of 0.1% methylene blue solution was added to the pellet at the bottom of the centrifuge tube, mixed, and a drop of stained mixture examined under the microscope for *D. immitis* microfilariae. Table 2 indicates when this test was carried out and, when determined, the level of microfilaremia.

The dog was treated as follows. Two days after the last of three doses of melarsomine dihydrochloride in July 2008 (i.e., on day 37), the dog showed transitory signs consistent with death of adult heartworms (elevated rectal temperature, lethargy, cough, increased lung sounds). Beginning on day 41, these signs were managed with prednisone (Apo-Prednisone; Apotex, Toronto, ON, Canada), 1.3 mg/kg bid for 6 days. Following the administration of milbemycin oxime (MO) per os at 0.74 mg/kg on day 74, IVM per os at 50 ug/kg on day 95, and IVM per os at 200 ug/kg (4× the normal microfilaricidal dose rate) on day 125, the dog remained continually microfilaremic. On day 207, six weeks after the second treatment regimen of melarsomine dihydrochloride, on days 159 and 160, a Knott's test was still positive, so the dog was again treated with 200µ/kg IVM per os. One month later, on day 242, a *D. immitis* antigen test was negative, which confirmed that the dog was free of adult worms. However, the dog was still microfilaremic. Thus, beginning on day 243, the dog was given MO per os at 0.74 mg/kg every 2 weeks on four occasions (see Table 2). Despite this, the dog remained microfilaremic on day 298. It was therefore administered MO per os at 1.1 mg/kg on days 298, 312, 326, 340 and 354. On day 356, blood was collected from the dog and examined: microfilariae were still present, and a *D. immitis* antigen test was still negative. On day 375, a blood sample was sent to Animal Health Laboratory, University of Guelph (AHLUG): microfilaremia was 6530 mf/ml, and an antigen test was still negative (see Table 2). As a result, beginning on day 384, the dog was administered MO per os at 2.0 mg/kg once daily for 7 days. On day 420, the dog had a microfilaraemia of 355 mf/ml. On day 420, the dog was again treated with MO per os at 2.0 mg/kg, and this was continued once daily for 8 days. Despite this second high-dose regimen, on day 480, while still testing negative with a heartworm antigen test, the dog had a microfilaremia of 1810 mf/ml.

Blood was collected from the dog on day 706 and DNA was isolated from pooled microfilariae.

TABLE 2

Diagnostic testing and treatment history for dog between 2008 and 2009

| Date (day) | Antigen test Name-result (+ve or −ve) | Adulticide (melarsomine)* dosage | Microfilariae concentration in blood (mf/ml) | Microfilaricide drug dosage (PO) | Comments |
| --- | --- | --- | --- | --- | --- |
| 2008 | | | | | |
| June 6 (1) | PetChek +ve$^a$ | | Knott's test +ve$^a$ | | |
| June 11 (6) | | 2.5 mg/kg | | | Classified as Class 2 heartworm disease |
| July 9 (34) | | 2.5 mg/kg | | | |
| July 10 (35) | | 2.5 mg/kg | | | |
| August 18 (74) | | | | MO, 0.74 mg/kg | |
| September 3 (90) | | | Knott's test +ve$^a$ | | |
| September 8 (95) | | | | IVM, 50 µg/kg | |
| October 6 (123) | | | Knott's test +ve$^a$ | | |
| October 8 (125) | | | | IVM, 200 µg/kg | |
| November 10 (158) | | | Knott's test +ve$^a$ | | |
| November 11 (159) | | 2.5 mg/kg | | | |
| November 12 (160) | | 2.5 mg/kg | | | |
| December 12 (190) | | | | MO, 0.74 mg/kg | |
| December 29 (207) | | | Knott's test +ve$^a$ | | |
| December 30 (208) | | | | IVM, 200 µg/kg | |

TABLE 2-continued

Diagnostic testing and treatment history for dog between 2008 and 2009

| Date (day) | Antigen test Name-result (+ve or −ve) | Adulticide (melarsomine)* dosage | Microfilariae concentration in blood (mf/ml) | Microfilaricide drug dosage (PO) | Comments |
|---|---|---|---|---|---|
| 2009 | | | | | |
| February 2 (242) | SNAP −ve[a] | | Knott's test +ve[a] ≥100[b] | | Interpretation: no adult heartworms |
| February 3 (243) | | | | MO, 0.74 mg/kg | |
| February 17 (257) | | | | MO, 0.74 mg/kg | |
| March 3 (271) | | | Knott's test +ve[a] ≥100[b] | MO, 0.74 mg/kg | |
| March 17 (285) | | | | MO, 0.74 mg/kg | |
| March 30 (298) | | | Knott's test +ve[a] ≥100[b] | MO, 1.1 mg/kg | |
| April 13 (312) | | | | MO, 1.1 mg/kg | |
| April 27 (326) | | | | MO, 1.1 mg/kg | |
| April 28 (327) | | | Knott's test +ve[a] | | |
| May 11 (340) | | | | MO, 1.1 mg/kg | |
| May 25 (354) | | | | MO, 1.1 mg/kg | |
| May 27 (356) | SNAP −ve[a] | | Knott's test +ve[a] | | No adult heartworm |
| June 8 (368) | | | | MO, 1.1 mg/kg | |
| June 15 (375) | DiroChek −ve[c] | | Knott's test +ve[c] 6530 | | No adult heartworm |
| June 24 (384) | | | | MO, 2.0 mg/kg daily for 7 days | |
| July 30 (420) | | | Knott's test +ve[c] 355 | MO, 2.0 mg/kg daily for 8 days | |
| September 28 (480) | PetChek −ve[a] | | Knott's test +ve[c] 1810 | | |
| 2010 | | | | | |
| May 12 (706) | | | | | Microfilariae collected for DNA isolation |

MO = milbemycin oxime (Interceptor ®);
IVM = ivermectin (Ivomec ® Injection for cattle, sheep and swine, Merial Inc.);
*Adulticide = Immiticide ®;
[a] = Main West Animal Hospital (i.e. test carried out in house);
[b] = Idexx Laboratories;
[c] = Animal Health Laboratory, University of Guelph.

f. LOE isolate case 2. Approximately 9000 pooled mf were obtained from a dog from Mechanicsville, Va., that had been treated with INTERCEPTOR® from 2004 to 2008. In May 2008, the dog was heartworm antigen positive and was placed on Heartgard Plus (IVM/PYR) for slow kill treatment. In 2008, the dog was still positive for heartworm antigen and was still microfilaremic. From Dr Blagburn's (Auburn University) in vitro assay: $LD_{95}$ concentration for susceptible mf produced only a 10.5% kill, and $2×LD_{95}$ produced a 13.6% kill of mf.

g. LOE isolate case 3. Pooled mf were obtained from low responder mf from an in vitro ivermectin susceptibility assay. The dog was a naturally infected client-owned animal, from Monroe, La., selected because it had been on ML heartworm preventative treatment. The veterinarian was convinced that compliance was not an issue. Patient records indicated that proper amounts of product had been provided to the client, based on numbers and weights of target animals in the household. The dog was microfilaremic despite the fact that it had been under ML heartworm prophylaxis.

h. LOE isolate case 4. Pooled mf were obtained from a dog that had the history as described below. This stray dog originated from Haywood County, Tenn., USA, and presented as heartworm antigen positive to a local clinic on Jan. 21, 2011. The dog was neutered on Jan. 26, 2011. On Feb. 1, 2011, doxycycline (200 mg orally twice per day) and prednisone (1 5 mg tablet orally every other day) therapy was initiated and continued for 30 days. On February 2, March 3 and Mar. 4, 2011, an injection of melarsomine dihydrochloride (IMMITICIDE®) (2.5 mg/kg) were given. On February 2, March 3 and Apr. 1, 2011, an oral dose of milbemycin oxime (INTERCEPTOR®) (11.5 mg/tablet) was given. On Apr. 5, 2011, a Knott's test was performed and was positive; ivermectin was administered subcutaneously at a dose of 0.26 mg/kg. On Apr. 11, 2011, Knott's test was again positive; ivermectin was administered subcutaneously at a dose of 0.39 mg/kg. Knott's tests were again performed on both April 19 and 26, 2011 and were both positive. On May 2, 2011, Knott's test was again positive and a blood smear showed microfilariae; Advantage MULTI® (2.5% imidacloprid, 10% moxidectin) was administered to the dog. On May 5, 2011, a blood smear was positive for microfilariae; at this time, microfilariae were collected. The repeated adulticide treatment led to the assumption they the dog was free of adult parasites. On Jun. 11, 2011, 200 mg of diethylcarbamazine was administered to the dog. No side effects of the treatment were noted. Within 7 days, the blood smear showed no mf. The dog was adopted on Aug. 18, 2011 and moved to Massachusetts.

i. LOE isolate case 5. Pooled mf were obtained from a dog originating from West Monroe, La., USA. This was a veterinarian's dog. The medical history implied compliant use of milbemycin oxime and there were several negative heartworm antigen tests at annual check-ups, until a positive heartworm antigen test and presence of mf in the blood on Sep. 25, 2008. An in vitro microfilaria sensitivity assay was performed (B. Blagburn laboratory, Auburn University, Alabama) on Nov. 19, 2008. The results of the assay indicated drug-resistant organisms. Mosquitoes were fed on infected blood samples from this original dog. L3 larvae were used to infect a second dog. At the time of infection, the second dog had been under treatment with ivermectin. Thereafter, at weekly intervals, the second dog received 1 dose of 3 µg ivermectin/kg, followed by 11 doses of 6 µg ivermectin/kg, followed by 4 doses of 12 µg ivermectin/kg, followed by 8 doses of 24 µg ivermectin/kg (interrupted for one week after the 4th dose). During the entire period of weekly dosing with ivermectin, the dog was remained positive for mf. Microfilariae were collected at 1 and 2 weeks after the last treatment were used in the analysis.

j. LOE isolate case 6. The samples correspond to the second passage of parasite that came from a dog originally from Earle, Ark., USA. The original isolate LOE-6 dog received milbemycin oxime in 2004 and 2005, ivermectin/pyrantel in 2006 and 2007, and ivermectin/praziquantel/pyrantel (IVERHART MAX™) in January 2008 and at the beginning of July 2008. The owner stated that she had been consistent with prophylaxis. This dog tested negative for heartworm antigen at annual check-ups in 2005, 2006 and 2007. This dog was positive for heartworm antigen and microfilaremic at the annual exam on Nov. 4, 2008. Results of the in vitro microfilaria assay (B. Blagburn laboratory, Auburn University, AL) on this dog suggested resistance. Dog-LOE-6, was experimentally infected on Nov. 16, 2009 with L3 larvae derived from mosquitoes fed with blood from the first passage. The first passage dog was experimentally infected on Feb. 24, 2009 with L3 larvae derived from mosquitos fed with blood from a naturally infected dog (the original isolate LOE-6 dog).

Example 2—DNA Isolation from Parasites Used in the Studies

Genomic DNA for the individual adult worms was extracted with DNeasy DNEASY™ kit from Qiagen (Qiagen Inc, Mississauga, Canada). The genomic DNA extraction of individual mf was extracted using QIAAMP® DNA Micro kit from Qiagen. To obtain enough DNA for analysis, the mf DNA was amplified using a REPLI-G® kit from Qiagen which allow amplifying the full genome from a very small amount of DNA. Mf were isolated by filtration through polycarbonate membrane filters from freshly drawn blood.

Example 3—DNA Sequencing, Analysis and Identification of SNPs

The goal was to identify genetic changes (e.g., nucleotide variations) present in LOE heartworm populations that were not present in the susceptible heartworm populations. Nucleotide variations in any of the LOE populations, as compared to a reference genome obtained from the susceptible isolates, would indicate potential SNP markers.

Initially, the genomes from the heartworm populations identified in lettered paragraphs a-h of Example 2 above (susceptible isolates from Missouri, Grand Canary Island, Grenada and Italy; LOE isolates cases 1-4) were sequenced using the HiSeq2000 system from ILLUMINA®. Table 3 shows the number of reads and the number of bases that were sequenced for each population. Not included in Table 3 is information from heartworm populations identified in paragraphs I and j (resistant isolates from LOE cases 5 and 6).

TABLE 3

Read information on isolates used for whole genome sequencing

| Isolates | Number of reads | Number of bases |
| --- | --- | --- |
| 1 - susceptible | 85,097,000 | 17,019,400,000 |
| 2 - susceptible | 78,242,862 | 15,648,572,400 |
| 3 - susceptible | 80,687,895 | 16,137,579,000 |
| 4 - susceptible | 75,515,617 | 15,103,123,400 |
| 5 - LOE-1 | 82,417,743 | 16,483,548,600 |
| 6 - LOE-2 | 74,261,369 | 14,852,273,800 |
| 7 - LOE-3 | 79,894,844 | 15,978,968,800 |
| 8 - LOE-4 | 75,477,318 | 15,095,463,600 |

The data generated from the ML susceptible samples (susceptible isolates from Missouri, Grand Canary Island, Grenada and Italy) were used to assemble the genome which was then used as the reference genome for the project. All of the individual fragments from the 4 susceptible populations were pooled together. Velvet aligner software (http://www.molecularevolution.org/software/genomics/velvet) was used to assemble the genome. Reads were filtered by having the adaptor sequences removed/clipped, if found. Reads were trimmed at Q30 length 32 base pairs. A length of 32 base pairs is the Aligner seed default value and the number of reads was consistent with the default value. Table 4 describes the assembly of the reference genome used for the study.

TABLE 4

Information about the D. immitis genome assembly

| | |
| --- | --- |
| Number of contigs | 22966 |
| 50% of the contigs are longer than | 28928 bp |
| Length of longest contig | 250211 bp |
| Total bases in contigs | 94611006 (94 Mb) |
| Number of contigs >1 kb | 6654 |
| Total bases in contigs >1 kb | 90045376 bp (90 Mb) |

Once the reference heartworm genome was obtained from sequences of the susceptible isolates/populations, then the genomes from the LOE populations were compared to the reference genome, to identify differences and possible SNPs. As part of this analysis, genetic loci containing the potential SNPs were shown not to be significantly different between the individual susceptible populations (i.e., between the susceptible isolates from Missouri, Grand Canary Island, Grenada and Italy), as well as not to be significantly different between the individual LOE populations (LOE 1-4), but were significantly different between the susceptible populations and the LOE populations. To perform this analysis, the software program called PoPoolation2 (Kofler et al. Bioinformatics 27:3435-3436, 2011; http://bioinformatics.oxfordjournals.org/content/27/24/3435) was used. The program required the use of other programs, such as Perl (http://www.perl.org/), R (http://www.r-project.org/), bwa, and Samtools. First, a synchronized file was generated, which contained the nucleotide frequencies for every population at every base in the reference genome, after filtering for base quality, in a concise format. The synchronized file generated with the PoPoolation2 program contained detailed nucleotide count information on loci for each of the populations. P-values were generated with Fisher's exact test for all the possible comparisons between populations. To identify loci associated with ML resistance, p-values needed to be simultaneously not statistically significant (>0.05) within all susceptible samples and within all the LOE samples, and statistically significant (<0.05) between all susceptible versus all LOE samples. Three hundred thirty eight loci met these criteria, including 12 that had a p-value of $10^{-5}$. Flanking regions of 1000 bp including each locus that was statistically different between the susceptible and LOE samples were analyzed by Blast (BlastN and BlastX) in NCBI (http://blast.ncbi.nlm.nih.gov/Blast.cgi) and in the Broad Institute filarial genome database (http://www.broadinstitute.org/annotation/genome/filarial_worms/Blast.html) to remove loci located in mitochondrial, *Wolbachia* or *C. lupus familiaris* DNA. Loci located in reads with very high polymorphism (>2 nucleotides and/or indels) or low coverage (<10x) were removed from further analysis. Nucleotide counts for each locus of interest were analyzed individually for the pooled populations to ensure that the increase or decrease in nucleotide frequency was in the same direction for all the susceptible samples or for all the LOE samples. The loci that best met the criteria were retained for further genotype analysis on individual parasites to assess actual allele frequencies in populations that had been characterized in terms of ML response.

From these analyses, 186 loci were found to be significantly different between the susceptible and LOE samples. As this approach was based on reads and nucleotide frequencies of pooled samples, these loci were further studied (SNP genotyping) using individual (not pooled) populations. For this purpose, SEQUENOM® SNP frequency analysis was used. Table 5, below, shows the origins of the DNA used in this analysis.

TABLE 5

Description of isolates used for Sequenom analysis

|  | State and/or country of origin | # Individual adult worm | # Individual microfilaria | From # dogs |
|---|---|---|---|---|
| Susceptible samples = 181 isolates |  |  |  |  |
| Sus1-Missouri | Missouri isolate, USA |  | 49 | 1 |
| Sus2-Missouri | Missouri isolate, USA |  | 45 | 1 |
| Grand Canary | Grand Canary, Spain | 71 |  | 11 |
| Grenada | Grenada, WI | 10 |  | 2 |
| Italy | Northern Italy | 6 |  |  |
| Low responder samples = 244 Isolates |  |  |  |  |
| LOE-1 | New Orleans, LA, USA, moved to Ontario, Canada |  | 56 | 1 |
| LOE-2 | Mechanicsville, VA, USA |  | 35 | 1 |

TABLE 5-continued

Description of isolates used for Sequenom analysis

|  | State and/or country of origin | # Individual adult worm | # Individual microfilaria | From # dogs |
|---|---|---|---|---|
| LOE-3 | Monroe, LA, USA |  | 51 | 1 |
| LOE-5 | West Monroe, LA, USA |  | 54 | 1 |
| LOE-6 | Earle, AR, USA |  | 48 | 1 |

SEQUENOM® analysis is based on multiplex PCR and MALDI-TOF mass spectrometry. The SEQUENOM® analysis was used to evaluate the 186 loci using 425 individual samples (5 panels with 36-38 SNPs in each panel). Primer design for each SNP marker was based on a requirement that elongation primers be located in a non-polymorphic region 15 base pairs before or after the SNP of interest. All the genome calls were performed blinded (i.e., the sample origin and dog treatment history was not known during the analysis). A total of 79050 genotypes were analyzed. From the 186 potential loci, 109 were observed to have technical advantages to predict for ML loss of efficacy. The susceptible population carried more than 90% of the wild-type genotype while the LOE population had a significant lower genotype frequency of the wild-type genotype. These 109 loci are disclosed herein as SEQ ID NOs: 1-109.

Example 4—Additional SNPs from Confirmed Resistant Organisms

LOE samples, as described in Example 1, were presumed to be resistant to MLs because of the history of treatment of the dogs with MLs and the continued presence of heartworm organisms. However, despite the history of treatment, an alternative explanation to true ML-resistance of the parasites is owner non-compliance of ML treatment. Therefore, a study was performed under controlled ML treatment conditions, to eliminate the possibility of owner non-compliance in ML treatment, as a possible reason for presence of heartworm organisms in dogs.

Heartworm organisms used in the efficacy studies were derived from one identified as Jd2009 from Earle, Ark., USA. Jd2009 received monthly MO in 2004 and 2005, IVM/pyrantel in 2006 and 2007, and IVM/praziquantel/pyrantel in January 2008 until early July 2008. Jd2009 tested negative for HW antigen in 2005, 2006, and 2007. This dog was heartworm antigen positive and microfilaremic on Apr. 11, 2008 despite a history of compliance with HW preventatives. Mf were obtained from the dog at this time with the consent of the owner and were sent to Auburn University, where the mf were examined for sensitivity to IVM in an in vitro concentration-response assay measuring migration (Blagburn, B., American Heartworm Society-13th Triennial State of the Heartworm Symposium, 2010). These mf were significantly less sensitive to IVM than mf obtained from a dog infected with a laboratory strain of *D. immitis* that was fully susceptible to the drug. The mf were used at Auburn University to infect mosquitoes to produce L3 that were used to infect dog Jd2009-1, which developed a patent infection. Mf from this dog were shown to be as resistant to ML as mf from Jd2009 in the in vitro migration assay.

L3s derived from mf harvested from Jd2009-1 were used at Auburn University to infect a second dog, Jd2009-2 and the dog was treated monthly with HEARTGARD PLUS® (0.006-0.013 mg/kg IVM) 9 consecutive times. Adult worms were recovered indicating that the Jd2009-2 isolate was resistant to IVM prophylaxis. In a second study, dogs were challenged with Jd2009-2 L3 on day 0 and treated monthly for 5 consecutive months with HEARTGARD PLUS® (0.007-0.009 mg/kg IVM; Study 1b). At necropsy on day 188, efficacy was 71.3%, confirming resistance to IVM prophylaxis in the Jd2009-2 isolate.

In another study, dogs were challenged with L3 on day 180 after PROHEART6® injection. At necropsy on day 150 after infection, efficacy was 21.6%, indicating that the Jd2009-2 was also resistant to the PROHEART6® long acting formulation of MOX, which has a claim for 100% protection for 180 days after treatment.

In another study, the confirmed IVM-resistant isolate Jd2009-2 was used to determine whether the resistance extended to other ML heartworm preventatives. None of the other ML heartworm preventatives (MOX, MO and SEL), given as monthly chemoprophylaxis as recommended, was fully effective, i.e., at least one dog in groups of four to six dogs on these heartworm preventatives became infected with *D. immitis* following treatment with each of these MLs used as recommended.

DNA from individual organisms from two Jd2009 isolates were used. DNA from individuals from one group, called RES-1, came from 4 dogs from the PROHEART6® study, described above. DNA from individuals from another group, called RES-2, came from 6 dogs from the HEARTGARD PLUS® study, described above.

DNA was isolated from 115 adult worms and 79 mf from the RES-1 and RES-2 populations, as described in Example 2, and were analyzed using SEQUENOM® SNP frequency analysis, as described in Example 3. From this analysis, 18 additional loci (out of the initial 186 loci) were significantly different between the susceptible and RES samples. These loci are disclosed herein as SEQ ID NOs: 110-127.

While example compositions, methods, and so on have been illustrated by description, and while the descriptions are in considerable detail, it is not the intention of the applicants to restrict or in any way limit the scope of the application. It is, of course, not possible to describe every conceivable combination of components or methodologies for purposes of describing the compositions, methods, and so on described herein. Additional advantages and modifications will readily appear to those skilled in the art. Therefore, the disclosure is not limited to the specific details, the representative apparatus, and illustrative examples shown and described. Thus, this application is intended to embrace alterations, modifications, and variations that fall within the scope of the application. Furthermore, the preceding description is not meant to limit the scope of the invention. Rather, the scope of the invention is to be determined by the appended claims and their equivalents.

---

The invention claimed is:

1. A method for determining the genotype of a *Dirofilaria immitis* nematode, the method comprising:
   a) contacting a *Dirofilaria immitis* nucleic acid molecule with at least one oligonucleotide having a length of 15-300 nucleotides of SEQ ID NO: 118, or a reverse complement thereof;
      wherein the at least one oligonucleotide comprises a G nucleotide at position 151 of SEQ ID NO: 118;
      wherein the at least one oligonucleotide further includes a detectable label; and
   b) detecting a G nucleotide at position 151 of SEQ ID NO: 118 in the *Dirofilaria immitis* nematode nucleic acid molecule.

2. The method of claim 1, wherein the at least one oligonucleotide has a length of 15-100 nucleotides.

3. The method of claim 1, wherein the at least one oligonucleotide has a length of 20-30 nucleotides.

4. The method of claim 1, wherein the detection of the G nucleotide at position 151 of SEQ ID NO: 118 in the *Dirofilaria immitis* nucleic acid molecule with the at least one oligonucleotide is detected by DNA sequencing, hybridization-based methods including with allele specific oligonucleotides, microarray analysis, enzyme-based methods, single strand conformational polymorphism (SSCP), high resolution melt (HRM) or approaches based on PCR, RT-PCR, or qRT-PCR.

5. The method of claim 1, further comprising:
   a) contacting the *Dirofilaria immitis* nucleic acid molecule with at least a second oligonucleotide consisting of 15-300 nucleotides of a sequence selected from the group consisting of SEQ ID NOs: 1-113, 115-117, and 119-127, or a reverse complement thereof;
      wherein the at least a second oligonucleotide comprises position 151 of the sequence selected from the group consisting of SEQ ID NOs: 1-113, 115-117, and 119-127;
      wherein the at least a second oligonucleotide further comprises a detectable label, and
   b) detecting the nucleotide at position 151 of the sequence selected from the group consisting of SEQ ID NOs: 1-113, 115-117, and 119-127 in the *Dirofilaria immitis* nematode nucleic acid molecule.

* * * * *

UNITED STATES PATENT AND TRADEMARK OFFICE
CERTIFICATE OF CORRECTION

| | | |
|---|---|---|
| PATENT NO. | : 10,000,811 B2 | Page 1 of 1 |
| APPLICATION NO. | : 14/896736 | |
| DATED | : June 19, 2018 | |
| INVENTOR(S) | : Roger K. Prichard et al. | |

It is certified that error appears in the above-identified patent and that said Letters Patent is hereby corrected as shown below:

On the Title Page

Column 2 (Other Publications) Line 17: Delete "tom" and insert -- from --, therefor.

In the Specification

Column 1 Line 8: Delete "published." and insert -- published --, therefor.

Column 1 Line 9: Delete "Patent." and insert -- Patent --, therefor.

Signed and Sealed this
Twenty-eighth Day of August, 2018

Andrei Iancu
*Director of the United States Patent and Trademark Office*